United States Patent
Gupta et al.

(10) Patent No.: US 6,348,591 B1
(45) Date of Patent: Feb. 19, 2002

(54) RED-SHIFTED TRISARYL-1,3,5-TRIAZINE ULTRAVIOLET LIGHT ABSORBERS

(75) Inventors: Ram Baboo Gupta, Stamford; Dennis John Jakiela, Orange, both of CT (US)

(73) Assignee: Cytec Technology Corp., Wilmington, DE (US)

(*) Notice: Subject to any disclaimer, the term of this patent is extended or adjusted under 35 U.S.C. 154(b) by 0 days.

(21) Appl. No.: 09/335,883

(22) Filed: Jun. 18, 1999

Related U.S. Application Data

(60) Provisional application No. 60/090,261, filed on Jun. 22, 1998.

(51) Int. Cl.$^7$ .................. C07D 251/02; C07D 403/02; C07D 403/14
(52) U.S. Cl. .................. 544/215; 544/216; 524/100; 430/507; 430/512; 252/301.23
(58) Field of Search .................. 544/215, 216

(56) References Cited

U.S. PATENT DOCUMENTS

| | | | |
|---|---|---|---|
| 3,043,709 A | 7/1962 | Amborski | 117/7 |
| 3,244,708 A | 4/1966 | Duennenberger et al. | 260/248 |
| 3,249,608 A | 5/1966 | Biland et al. | 260/248 |
| 3,309,220 A | 3/1967 | Osteen | 117/33.3 |
| 3,423,360 A | 1/1969 | Huber et al. | 260/47 |
| 3,487,505 A | 1/1970 | Chisholm et al. | 18/13 |
| 3,557,265 A | 1/1971 | Chisholm et al. | 264/47 |
| 3,723,427 A | 3/1973 | Susi | 260/248 |
| 3,843,371 A | 10/1974 | Piller et al. | 96/84 |
| 3,862,053 A | 1/1975 | Susi | 252/403 |
| 3,896,125 A | 7/1975 | Helmo et al. | 260/249.5 |
| 3,923,869 A | 12/1975 | Song et al. | 260/469 |
| 4,226,999 A | 10/1980 | Malherbe et al. | 546/222 |
| 4,284,790 A | 8/1981 | Hinsken et al. | 560/15 |
| 4,314,933 A | 2/1982 | Berner | 260/45.75 N |
| 4,325,863 A | 4/1982 | Hinsken et al. | 624/111 |
| 4,331,586 A | 5/1982 | Hardy | 525/186 |
| 4,338,244 A | 7/1982 | Hinsken et al. | 524/109 |
| 4,344,876 A | 8/1982 | Berner | 524/91 |
| 4,353,965 A | 10/1982 | Olson et al. | 428/412 |
| 4,426,471 A | 1/1984 | Berner | 524/91 |
| 4,426,472 A | 1/1984 | Berner | 524/99 |
| 4,439,615 A | 3/1984 | Rosenberger et al. | 560/15 |
| 4,518,686 A | 5/1985 | Sasaki et al. | 430/512 |
| 4,540,623 A | 9/1985 | Im et al. | 428/220 |
| 4,613,642 A | 9/1986 | Burton | 524/349 |
| 4,619,956 A | 10/1986 | Susi | 524/87 |
| 4,668,588 A | 5/1987 | Kishima | 428/412 |
| 4,721,792 A | 1/1988 | Sasaki et al. | 548/304 |
| 4,740,542 A | 4/1988 | Susi | 524/87 |
| 4,775,707 A | 10/1988 | Slongo et al. | 524/91 |
| 4,826,978 A | 5/1989 | Migdal et al. | 544/216 |
| 4,853,471 A | 8/1989 | Rody et al. | 548/261 |
| 4,921,966 A | 5/1990 | Stegmann et al. | 548/260 |
| 4,937,026 A | 6/1990 | Goossens et al. | 264/129 |
| 4,948,666 A | 8/1990 | Paul et al. | 428/334 |
| 4,960,863 A | 10/1990 | Rosenquist | 528/480 |
| 4,962,142 A | 10/1990 | Migdal et al. | 524/100 |
| 4,973,701 A | 11/1990 | Winter et al. | 548/260 |
| 4,973,702 A | 11/1990 | Rody et al. | 548/261 |
| 4,992,322 A | 2/1991 | Curry et al. | 428/215 |
| 5,004,770 A | 4/1991 | Cortolano et al. | 524/99 |
| 5,006,577 A | 4/1991 | Behrens et al. | 524/95 |
| 5,030,731 A | 7/1991 | Slongo et al. | 548/260 |
| 5,064,883 A | 11/1991 | Behrens et al. | 524/95 |
| 5,071,981 A | 12/1991 | Son et al. | 544/198 |
| 5,106,891 A | 4/1992 | Valet | 524/91 |
| 5,112,890 A | 5/1992 | Behrens et al. | 524/95 |
| 5,124,378 A | 6/1992 | Behrens et al. | 524/95 |
| 5,175,312 A | 12/1992 | Dubs et al. | 549/307 |
| 5,189,084 A | 2/1993 | Birbaum et al. | 524/100 |
| 5,198,498 A | 3/1993 | Valet et al. | 525/125 |
| 5,204,473 A | 4/1993 | Winter et al. | 546/188 |
| 5,216,052 A | 6/1993 | Nesvadba et al. | 524/108 |
| 5,252,643 A | 10/1993 | Nesvadba | 524/111 |
| 5,288,778 A | 2/1994 | Schmitter et al. | 524/100 |

(List continued on next page.)

FOREIGN PATENT DOCUMENTS

| | | | |
|---|---|---|---|
| CA | 2162645 | * | 5/1996 |
| DE | 3922496 | | 1/1991 |
| EP | 309400 | | 3/1989 |
| EP | 309401 | | 3/1989 |
| EP | 434608 | | 6/1991 |
| EP | 444323 | | 9/1991 |
| GB | 2269819 A | | 9/1994 |
| GB | 2290745 A0 | | 1/1996 |
| WO | WO 94/04515 | | 3/1994 |

OTHER PUBLICATIONS

Diffey, J. Soc. Cosmet. 40, 127–133, 1989.

Ullmann's Encyclopedia of Industrial Chemistry, 5$^{th}$ Edition, vol. A18, pp. 368–426, 429–471, 491–500, VCH, Weinheim 1991.

*Primary Examiner*—Richard L. Raymond
*Assistant Examiner*—Venkataraman Balasubramanian
(74) *Attorney, Agent, or Firm*—Pennie & Edmonds LLP

(57) ABSTRACT

This invention relates generally to red-shifted trisaryl-1,3,5-triazines and the use thereof to protect against degradation by environmental forces, inclusive of ultraviolet light, actinic radiation, oxidation, moisture, atmospheric pollutants and combinations thereof. The new class of trisaryl-1,3,5-triazines comprises an aryl ring attached to the triazine ring [and preferably an aryl ring containing a hydroxyl group, either free or blocked to form a latent stabilizer, ortho- to the point of attachment to the triazine ring (2-position) and a hydroxyl group or a moiety joined by an ether linkage para- to the point of attachment to the triazine ring (4-position)] substituted at the 3-position or disubstituted at the 3- and 5-positions with a group comprising an amide and/or an amine. These materials may be incorporated into formulations comprising coatings, polymers, resins, organic compounds and the like. A method for stabilizing a material by incorporating such red-shifted trisaryl-1,3,5-triazines is also disclosed.

18 Claims, No Drawings

U.S. PATENT DOCUMENTS

| | | | |
|---|---|---|---|
| 5,298,067 A | 3/1994 | Valet et al. | 106/506 |
| 5,300,414 A | 4/1994 | Leppard et al. | 430/507 |
| 5,322,868 A | 6/1994 | Valet et al. | 524/89 |
| 5,354,794 A | 10/1994 | Stevenson et al. | 524/100 |
| 5,356,966 A | 10/1994 | Nesvadba | 524/111 |
| 5,364,749 A | 11/1994 | Leppard et al. | 403/507 |
| 5,367,008 A | 11/1994 | Nesvadba | 524/111 |
| 5,369,140 A | 11/1994 | Valet et al. | 522/75 |
| 5,369,159 A | 11/1994 | Nesvadba | 524/111 |
| 5,376,710 A | 12/1994 | Slongo et al. | 524/87 |
| 5,420,204 A | 5/1995 | Valet et al. | 525/125 |
| 5,428,162 A | 6/1995 | Nesvadba | 544/221 |
| 5,428,177 A | 6/1995 | Nesvadba | 549/304 |
| 5,445,872 A | 8/1995 | Suhadolnik et al. | 428/215 |
| 5,459,222 A | 10/1995 | Rodgers et al. | 528/73 |
| 5,461,151 A | 10/1995 | Waterman | 544/216 |
| 5,476,937 A | 12/1995 | Stevenson et al. | 544/216 |
| 5,556,973 A * | 9/1996 | Stevenson et al. | 544/216 |
| 5,585,422 A | 12/1996 | Falk et al. | 524/100 |

* cited by examiner

RED-SHIFTED TRISARYL-1,3,5-TRIAZINE ULTRAVIOLET LIGHT ABSORBERS

This application claims benefit of U.S. Provisional Application No. 60/090,261, filed Jun. 22, 1998.

BACKGROUND OF THE INVENTION

1. Field of the Invention

This invention relates generally to novel red-shifted trisaryl-1,3,5-triazines and the use thereof to protect against degradation by environmental forces, inclusive of actinic radiation, oxidation, moisture, atmospheric pollutants and combinations thereof.

2. Description of Related Art

Exposure to sunlight and other sources of ultraviolet radiation are known to cause degradation of a variety of materials, especially a polymeric materials. For example, polymeric materials such as plastics often discolor and/or become brittle as a result of prolonged exposure to ultraviolet light. Accordingly, a large body of art has been developed directed towards materials such as ultraviolet light absorbers and stabilizers which are capable of inhibiting such degradation.

A class of materials known to be ultraviolet light absorbers are trisaryl-1,3,5-triazines, in which at least one of the aryl rings has a hydroxyl group ortho to the point of attachment to the triazine ring. In general this class of materials is well known in the art. Disclosures of a number of such trisaryl-1,3,5-triazines can be found in the patent literature. For example, U.S. Pat. No. 3,843,371 discloses hydroxyphenyltrizines for use in photographic materials. The triazines in this patent, however, show poor solubilities and poor stabilities.

U.S. Pat. No. 3,896,125 discloses hydroxyphenyl triazines, but these, too are poorly soluble and discolor with time.

Typically, the aforementioned aryl ring with the hydroxyl group ortho to the point of attachment to the triazine ring is based on resorcinol and, consequently, this aryl ring also contains a second substituent (either a hydroxyl group or a derivative thereof) para- to the point of attachment to the triazine ring. For example, U.S. Pat. Nos. 3,118,887 and 3,244,708 disclose p-alkoxy-o-hydroxyphenyl triazines with improved UV protection, but such triazines also exhibit poor solubility and poor long-term stabilities.

Typically, the aforementioned aryl ring with the hydroxyl group ortho to the point of attachment to the triazine ring, i.e., a 2-position hydroxyl group, is based on resorcinol and, consequently, this aryl ring also contains a second substituent (either a hydroxyl group or a derivative thereof) para- to the point of attachment to the triazine ring, i.e., in the 4-position. This second substituent can be "non-reactive," as in the case of an alkyloxy group, or "reactive" as in the case of a hydroxyalkyloxy (active hydrogen reactive site) or (meth)acryloyl (ethylenic unsaturation reactive site) group.

A general disadvantage of trisaryl-1,3,5-triazines containing one resorcinol group is that they absorb less in the 360–400 nm region than other commercially available UV absorbers, e.g., hydroxyphenylbenzotriazoles. The spectral region from about 400 nm to about 360 nm is commonly known as upper wavelength UV light. Therefore, it is desirable to provide trisaryl-1,3,5-triazines with significant UV absorbance extending from the UV region (below about 360 nm in wavelength) into the upper UV region from about 360 nm to about 400 nm. Thus, trisaryl-1,3,5-triazines that have a maximum UV absorbance which is shifted toward the upper UV region are known as often referred to as red-shifted. This invention discloses novel red-shifted trisaryl-1,3,5-triazines, i.e., those comprising resorcinol-derived structures that have significant UV absorbance in the upper UV region.

U.S. Pat. Nos. 4,950,304 and 5,096,489 disclose sulfonated trisaryl-1,3,5-triazines comprising resorcinol optionally substituted at the resorcinol 3-position or 5-position, or which may be 3,5-disubstituted.

U.S. Pat. Nos. 5,543,518 and 5,637,706 both generically disclose tris-aryl-1,3,5-triazines comprising resorcinol further substituted at the 5-position with an alkyl group which may be substituted by an amine. Such a compound, 2-(2,4-dihydroxy-5-(1-isobutylamino)propylphenyl)-4,6-bis-(2,4-dimethylphenyl)-1,3 5-triazine is given in Example 14 of both patents. This compound is made by a Friedel-Crafts acylation with propionyl chloride, reaction of the resulting ketone with isobutylamine, and reduction of the resulting imine.

U.S. Pat. No. 5,726,309 discloses 3,3', 3,5' and 5,5' methylene—bridged dimers of triazines (Example 2) and 3,5' and 5,5 benzylidene—bridged dimers of triazines.

In U.S. Pat. No. 5,585,422, dipiperidinomethane is used as the reagent and sodium hydroxide is used as a catalyst for introducing the piperidinomethyl group to 2-(2-hydroxy-4-hexyloxyphenyl)-4,6-bis-(2,4-dimethylphenyl)-1,3,5-triazine. The dipiperidinomethane compound is prepared in a separate step. Similar 2-(2-hydroxy-4-alkyloxyphenyl) derivatives have been found to fail to react with dialkyl amines and formaldehyde.

U.S. Pat. No. 5,585,422 discloses in Example 3 a mixture of 3-piperidinomethyl and 5-piperidinomethyl triazines, 2,4-diphenyl-6-(2-hydroxy-5-piperidinomethyl-4-hexyloxyphenyl)-1,3,5-triazine. These compounds are only used as intermediates for the preparation of stabilizers.

Normally, red-shifted triazine UV absorbers are yellow compounds. It is desirable to add a red-shifted UV absorber to the pigmented base-coat of a multi-layer clear coat/base coat system. The yellow color can then be masked or compensated for by adjustment of the pigment formulation. However migration of the red-shifted UV absorber out of the base-coat and into the clear coat may be adversely affect the overall appearance of the final cured multi-layer coating film.

Stabilizers with a reactive site, i.e., bondable stabilizers, have a potential advantage in this respect in that, depending on the bondable functionality and the particular polymer system to be stabilized, they can be chemically incorporated into a polymer structure via reaction of the bondable functionality either during polymer formation (such as in the case of a crosslinking polymer system) or subsequently with a preformed polymer having appropriate reactive functionality. Accordingly, due to such bonding, migration of these UV absorbers between layers of multi-layer coatings and into polymer substrates is greatly reduced.

Several of the previously incorporated references disclose bondable trisaryl-1,3,5-triazines. For example, U.S. Pat. No. 5,189,084 discloses various bondable triazines and the incorporation of these compounds into polymers by chemical bonding.

Additionally, U.S. Pat. No. 5,354,794 discloses generically triazines with one or more carbonyl and/or ester groups.

There remains a need for triazine UV absorbers having improved compatibility with the polymer systems to which they are added, as well as for triazine UV absorbers which provided improved absorbance.

SUMMARY OF THE INVENTION

The bondable red-shifted containing trisaryl-1,3,5-triazines of the present invention satisfy this need.

The present invention provides a new class of red-shifted trisaryl-1,3,5-triazines in which at least one aryl ring, attached at the 1 position to the triazine ring, is substituted with a group comprising an amine and/or an amide at the 3 position or which is disubstituted with groups comprising an amine and/or an amide at the 3 and 5 positions. Optionally, two red-shifted trisaryl-1,3,5-triazines, each containing at least one aryl ring attached at the 1 position to the triazine ring with each aryl ring comprising a 3 position substituent comprising an amide and/or an amine, may be dimerized to form a 5,5'-bridged red-shifted triazine of the present invention. Preferably, the at least one 3-substituted or 3,5-disubstituted aryl ring contains a 2 position hydroxyl group and either a 4 position hydroxyl group or a moiety joined to the aryl ring 4 position by an ether linkage. More specifically, the new trisaryl-1,3,5-triazines of the present invention have the following general formulas (I), (II) and (III):

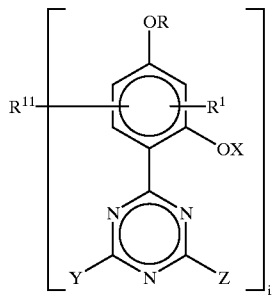
(I)

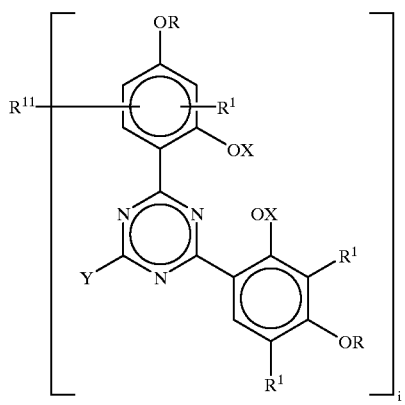
(II)

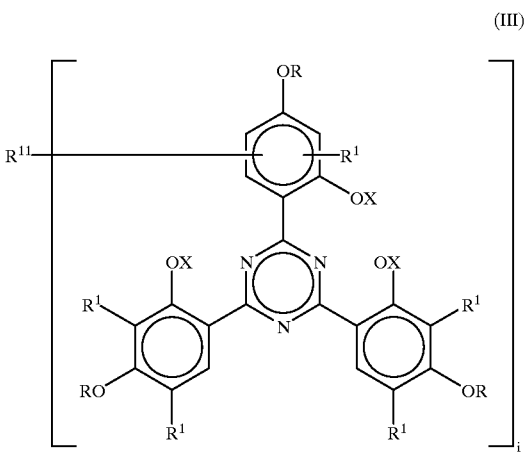
(III)

wherein
i is 1 or 2;
each X is independently selected from hydrogen, $C_1$–$C_8$ alkyl, halogen-substituted $C_1$–$C_8$ alkyl, allyl, —$COR^a$, —$SO_2R^b$, —$SiR^cR^dR^e$, —$PR^fR^g$ and —$POR^fR^g$;
each of Y and Z is independently selected from an aryl ring of the general formula (IV)

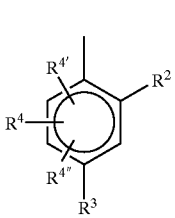
(IV)

each R is independently selected from a hydrogen, a hydrocarbyl group and a functional hydrocarbyl group;
each $R^a$ is independently selected from $C_1$–$C_8$ alkyl, halogen-substituted $C_1$–$C_8$ alkyl, $C_5$–$C_{12}$ cycloalkyl, $C_2$–$C_8$ alkenyl, —$CH_2$—CO—$CH_3$, $C_7$–$C_{12}$ aralkyl, $C_1$–$C_{12}$ alkoxy, or phenyl which is unsubstituted or substituted by $C_1$–$C_{12}$ alkyl, $C_1$–$C_4$ alkoxy, halogen and benzyl;
each $R^b$ is independently selected from $C_1$–$C_{12}$ alkyl, $C_6$–$C_{10}$ aryl and $C_7$–$C_{18}$ alkylaryl;
each $R^c$, $R^d$ and $R^e$ is independently selected from $C_1$–$C_{18}$ alkyl, cyclohexyl, phenyl and $C_1$–$C_{18}$ alkoxy;
each $R^f$ and $R^g$ is independently selected from $C_1$–$C_{12}$ alkoxy, phenoxy, $C_1$–$C_{12}$ alkyl, $C_5$–$C_{12}$ cycloalkyl, benzyl, tolyl and phenyl;
when i is 1, $R^1$ is attached to the 3-position of the ring bearing —OX and $R^{11}$ is attached to the 5-position of the ring bearing —OX and is $R^1$, and, when i is 2, $R^1$ is attached, independently, to either the 3-position or the 5-position of a ring bearing —OX and $R^{11}$ is attached to the position of the same ring bearing —OX not occupied by $R^1$ and $R^{11}$ is a hydrocarbylene group of 1 to 24 carbon atoms;
each $R^1$, $R^2$, $R^4$, $R^{4'}$ and $R^{4''}$ is independently selected from hydrogen, hydrocarbyl, functional hydrocarbyl, —O(hydrocarbyl), —O(functional hydrocarbyl), —SR, halogen, —$SO_2R$, —$SO_3R$, —COOR, —COR, —OCOR, —NRR and cyano; and each $R^3$ is independently selected from R, —OR, —SR, halogen, —SO$_2$R, —SO$_3$R, —COOR, —COR, —NRR and cyano.

The structures of formulas (I), (II) and (III) are further characterized in that at least one 3-position or 5-position $R^1$ group is independently selected from a group of the general formulas (V) ("amino group") and (VI) ("amido group")

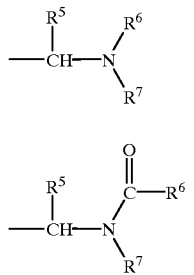

wherein
- $R^5$ is independently selected from hydrogen, linear or branched hydrocarbyl group of 1 to 24 carbon atoms, phenyl, and aralkyl of 7 to 24 carbon atoms; and
- each $R^6$ and $R^7$ is independently selected from hydrogen, a hydrocarbyl group and a functional hydrocarbyl group.

In an alternate embodiment, the structures of formulas (I), (II) and (III) are further characterized in that at least one 3-position $R^1$ group and at least one 5-position $R^1$ group attached to the same aryl ring as the 3-position $R^1$ group are independently selected from a group of the general formulas (V) and (VI) wherein
- $R^5$ is independently selected from hydrogen, linear or branched hydrocarbyl group of 1 to 24 carbon atoms, phenyl, and aralkyl of 7 to 24 carbon atoms; and
- each $R^6$ and $R^7$ is independently selected from hydrogen, a hydrocarbyl group and a functional hydrocarbyl group.

Preferably, $R^5$ is independently selected from hydrogen, linear or branched alkyl group of 1 to 24 carbon atoms, phenyl, and aralkyl of 7 to 24 carbon atoms.

Preferably, at least one of $R^6$ and $R^7$ is a functional hydrocarbyl group or is a hydrocarbyl group which contains ethylenic unsaturation or another bondable functionality in the hydrocarbyl chain or ring.

The red-shifted tris-aryl-1,3,5-triazines of the present invention have the added benefit of being capable of forming dimers by linking the 4-position hydroxyl groups on two triazine molecules by a bridge member. In particular, polyoxyalkylene bridge members are preferred. Such polyoxyalkylene bridge members include but are not limited to:

a polyoxyalkylene bridge member of the formula (i)

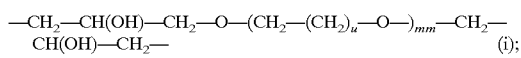

a polyoxyalkylene bridge member of the formula (ii)

a polyoxyalkylene bridge member of the formula (iii)

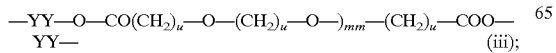

a polyoxyalkylene bridge member of the formula (iv)

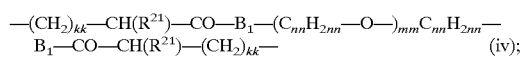

a polyoxyalkylene bridge member of the formula (v)

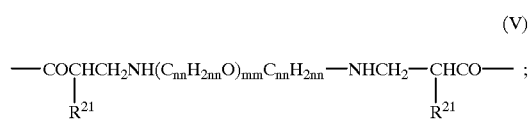

a polyoxyalkylene bridge member of the formula (vi)

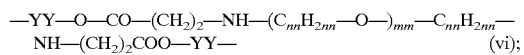

a polyoxyalkylene bridge member of the formula (vii)

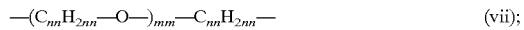

and a polyoxyalkylene bridge member of the formula (viii)

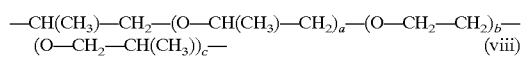

wherein a+c=2.5 and b=8.5 to 40.5 or a+c=2 to 33 and b=0;
wherein $R^{21}$ is hydrogen or $C_1$–$C_{16}$ alkyl;
YY is unsubstituted or substituted $C_2$–$C_{20}$ alkyl;
$B_1$ is —NH— or —O—;
kk is zero or an integer from 1–16;
mm is an integer from 2 to 60;
nn is an integer from 2 to 6; and
u is an integer from 1 to 4.

Furthermore, dimers may be formed from bridging two group (V) containing red-shifted triazines. The bridge may be formed between two such group (V)s in the 3,3'-position, in the 5,5'-position, in the 5,3'-position, or in the 3,5'-position of the respective triazines, as is discussed in detail below. For example, such bridges can take the form of the following structure:

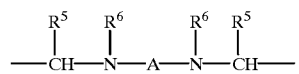

wherein A is hydrocarbylene and, preferably, such bridges are selected from at least one of:

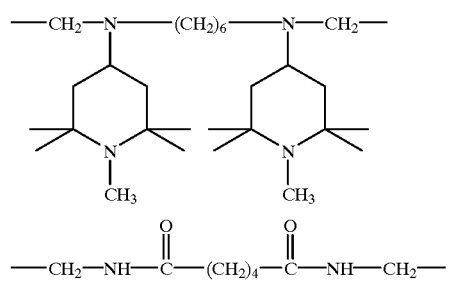

-continued

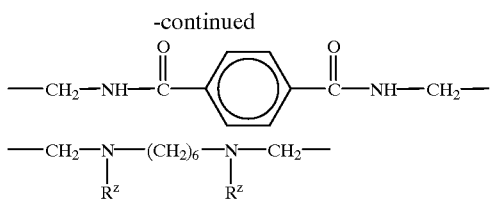

wherein $R^z$ is linear or branched alkyl of 1 to 4 carbon atoms. Additionally, such bridges may be formed from, e.g., a polyamine or polyamide end-capped with amino groups, amido groups or mixtures thereof.

Additionally, the monomeric and/or dimeric red-shifted triazines described herein may be formed into oligomers in the manner disclosed in U.S. Pat. No. 5,585,422, the methods of which can be readily adapted by routine experimentation for use with the red-shifted tris-aryl-1,3,5-triazines of the present invention.

Moreover, the red-shifted tris-aryl-1,3,5-triazines of the present invention have the added benefit of being capable of being chemically bound to polymer systems via functionality, e.g., a pendant vinyl or hydroxyl group, attached to (1) a 3-position amino or amido $R^1$ group, (2) a 5-position amino or amido $R^1$ group, (3) a 4-position R group, or (4) any combination of (1) through (3) inclusive. For example, copolymers of a red-shifted triazine and a polymer may be formed from a triazine substituted with a diethanol amino methyl group (V), i.e., wherein $R^5$ is $CH_2$ and $R^6$ and $R^7$ are $CH_2$—$CH_2$—OH. Such a group (V) comprising triazine may be condensation copolymerized with polymers such as polyamides, polyesters and polyurethanes as described in EP 627452 A1.

These trisaryl-1,3,5-triazines may in general be prepared by reacting a trisaryl-1,3,5-triazine precursor, having at least one aryl ring with hydroxyl groups at both the 2- and 4-positions with an appropriate compound or compounds to functionalize the 3-position or both the 3- and 5-positions with a group of the above formula (V) or (VI). Bridged red-shifted trisaryl-1,3,5-triazine dimers may also be prepared. Further preferred process details are disclosed below.

The novel red-shifted trisaryl-1,3,5-triazines of the present invention are particularly useful as ultraviolet light absorber additives for stabilizing a wide variety of materials including, for example, organic compounds, oils, fats, waxes, cosmetics, dyes and biocides, and particularly various organic polymers (both crosslinked and non-crosslinked) used in applications such as photographic materials, plastics, rubbers, paints and other coatings, and adhesives, such as disclosed in a number of the previously incorporated references. The present invention, consequently, also relates to a method for stabilizing a material by incorporating into such material, e.g., organic material, the inventive red-shifted trisaryl-1,3,5-triazine in an amount effective to stabilize the material against the effects of actinic radiation, and the material so stabilized.

The novel red-shifted trisaryl-1,3,5-triazines of the present invention are also effective as ultraviolet light screening agents in applications such as sunscreens and other cosmetic preparations, capstock layers for extruded polymers and laminated UV-screening window films, among others. The present invention, consequently, also relates to a method for screening ultraviolet light from a substrate by applying to such substrate a layer of a composition comprising the novel red-shifted containing trisaryl-1,3,5-triazines, and the substrate so screened.

These and other features and advantages of the present invention will be more readily understood by those of ordinary skill in the art from a reading of the following detailed description.

DETAILED DESCRIPTION OF THE PREFERRED EMBODIMENTS

The Red-Shifted Trisaryl-1,3,5-Triazines

As indicated above, the trisaryl-1,3,5-triazines in accordance with the present invention are compounds of the general formulas (I), (II) and (III).

As used herein, the term "red-shifted trisaryl-1,3,5-triazine" broadly refers to any compound of formulas (I), (II) or (III) wherein at least one 3-position or 5-position $R^1$ group comprises an amido or amido group.

The term "hydrocarbyl" in the context of the present invention, and in the above formulas, broadly refers to a monovalent hydrocarbon group in which the valency is derived by abstraction of a hydrogen from a carbon atom. Hydrocarbyl includes, for example, aliphatics (straight and branched chain), cycloaliphatics, aromatics and mixed character groups (e.g., aralkyl, alkylaryl, alkynyl, cycloalkynyl). More specifically, hydrocarbyl includes (but is not limited to) such groups as alkyl, cycloalkyl, aryl, aralkyl, alkylaryl, alkenyl and cycloalkenyl, preferably having up to 24 carbon atoms. A hydrocarbyl may optionally contain a carbonyl group or groups (which is/are included in the carbon count) and/or a heteroatom or heteroatoms (such as at least one oxygen, sulfur, nitrogen or silicon), in the chain or ring.

The term "functional hydrocarbyl" in the context of the present invention, and in the above formulas, broadly refers to a hydrocarbyl possessing pendant and/or terminal "reactive" and/or "latent reactive" functionality and/or leaving groups. Reactive functionality refers to functionality which is reactive with common monomer/polymer functionality under normal conditions well understood by those persons of ordinary skill in the relevant art. As examples of reactive functionality may be mentioned active hydrogen containing groups such as hydroxyl, amino, carboxyl, thio, amido and activated methylene; isocyanato; cyano; epoxy; and ethylenically unsaturated groups such as allyl, acryloyl and methacryloyl, and maleate and maleimido. Latent reactive functionality refers to reactive functionality which is blocked or masked to prevent premature reaction. As examples of latent reactive functionality may be mentioned ketimines and aldimines (amines blocked, respectively, with ketones and aldehydes); amine-carboxylate salts; and blocked isocyanates such as alcohol (carbamates), oxime and caprolactam blocked variations. A "leaving" group within the meaning of the present invention and, as would clearly be understood by those persons of ordinary skill in the relevant art, is a substituent attached to the hydrocarbyl chain or ring which during reaction is displaced to create a valency on a carbon atom in the hydrocarbyl chain or ring. As examples of leaving groups may be mentioned halogen atoms such as chlorine, bromine and iodine; hydroxyl groups; quaternary ammonium salts ($NT_4^+$); sulfonium salts ($ST_3^+$); and sulfonates (—$OSO_3T$); where T is, e.g., methyl or para-tolyl. Preferred functionality includes hydroxyl, —$COOR^8$, —$CR^9$=$CH_2$, —CO—$CR^9$=$CH_2$, Cl, an isocyanate group, a blocked isocyanate group and —$NHR^8$,

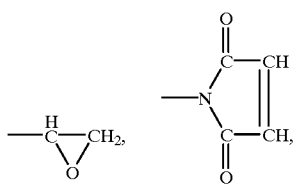

wherein

R⁸ is selected from hydrogen and a hydrocarbyl (preferably of up to 24 carbon atoms); and R⁹ is selected from hydrogen and an alkyl of 1 to 4 carbon atoms.

The term "hydrocarbylene" in the context of the present invention is a divalent hydrocarbon group in which both valencies derive by abstraction of hydrogens from carbon atoms. Included within the definition of hydrocarbylene are the same groups as indicated above for hydrocarbyl and functional hydrocarbyl with, of course, the extra valency (for example, alkylene, alkenylene, arylene, alkylarylene, etc.)

The trisaryl-1,3,5-triazines in accordance with the present invention also relate to latent stabilizing compounds against actinic radiation of the general formulas (I), (II) and (III) wherein at least one X is other than hydrogen. Such latent stabilizing compounds liberate the effective stabilizers by cleavage of the O—X bond, e.g., by heating or by exposure to UV radiation. Latent stabilizing compounds are desirable because they have many favorable properties, i.e., good substrate compatibility, good color properties, a high cleavage rate of the O—X bond and a long shelf life. The use of latent stabilizing compounds is further described in U.S. Pat. No. 4,775,707, U.S. Pat. No. 5,030,731 and CA A1-2162645.

Latent stabilizing compounds comprising the red-shifted trisaryl-1,3,5-triazines in accordance with the present invention can be prepared from compounds of the general formulas (I), (II) and (III) wherein at least one X is hydrogen by subjecting said compounds to a further reaction to form latent stabilizing compounds, as described in U.S. Pat. No. 4,775,707 and U.S. Pat. No. 5,030,731. For example, acylation can be carried out according to the process described in U.S. Pat. No. 3,249,608, except that excess acylating reagent is preferably employed, to give compounds in which X is —COR$^a$.

The reaction to give the latent stabilizing compounds of the present invention of the general formulas (I), (II) and (III) in which X is allyl, —COR$^a$, —SO₂R$^b$, SiR$^c$R$^d$R$^e$, —PR$^f$R$^g$, or —POR$^f$R$^g$ can be carried out, for example, by reaction of the compounds of the general formulas (I), (II) and (III) wherein at least one X is hydrogen with the corresponding chlorides: allyl chloride, Cl—COR$^a$, Cl—SO₂R$^b$, Cl—SiR$^c$R$^d$R$^e$, Cl—PR$^f$R$^g$, or Cl—POR$^f$R$^g$. Furthermore, acylated compounds can be obtained by reaction with anhydrides, ketenes or esters, such as lower alkyl esters, as is well known to one skilled in the art. The above-described reagents may be used in approximately equimolar amounts or in excess, for example, from 2 to 20 mol with respect to the hydroxyl groups desired to be made latent in the starting compound of the general formula (I), (II) or (III).

Catalysts customarily used for acylation, sulfonylation, phosphonylation or silylation reactions may be used in forming the latent stabilizing red-shifted trisaryl-1,3,5-triazines of the present invention. For example, acylation and sulfonylation reaction catalysts such as tertiary or quaternary amines, such as triethylamine, dimethylaminopyridine or tetrabutylammonium salts, may be used for forming these latent stabilizing compounds.

The reaction may be carried out in the presence of a solvent, such as relatively inert organics, e.g., hydrocarbons such as toluene and xylene, chlorinated hydrocarbons such as carbon tetrachloride or chloroform, or ethers such as tetrahydrofuran or dibutyl ether, or without a solvent. Alternatively, the reagent(s) may be employed as the solvent. The reaction temperature is usually between room temperature and about 150° C., for example, up to the boiling point of the solvent when a solvent is used.

In preferred embodiments, each X is hydrogen.

In preferred embodiments, each R group is independently selected from hydrogen, an alkyl of 1 to 24 carbon atoms (which may optionally be substituted by one or more hydroxyl, carboxyl, carboalkoxy (ester), sulfone, epoxy and/or amino groups and/or contain one or more carbonyl groups, oxygen atoms and/or nitrogen atoms in the chain); an alkenyl of 2 to 24 carbon atoms (which may optionally be substituted by hydroxyl, carboxyl, epoxy and/or amino group(s) and/or contain carbonyl, oxygen and/or nitrogen in the chain), a cycloalkyl of 5 to 24 carbon atoms (which may optionally be substituted by hydroxyl, carboxyl and/or amino group(s) and/or contain carbonyl, oxygen and/or nitrogen in the ring), and an aralkyl of 7 to 24 carbon atoms (which may optionally be substituted by hydroxyl, carboxyl and/or amino group(s) and/or contain carbonyl, oxygen and/or nitrogen in the ring).

More preferably, each R group is independently selected from hydrogen, an alkyl of 1 to 24 carbon atoms optionally containing an oxygen atom in the chain, and a hydroxyalkyl of 1 to 24 carbon atoms group optionally containing an oxygen atom in the chain. Still more preferably, each R is independently selected from the group consisting of hydrogen, C₁–C₂₄ alkyl or mixtures thereof; C₁–C₂₄ branched alkyl or mixtures thereof; C₃–C₆ alkenyl; —COR¹²; —COOR¹²; —NHCOR¹²; —SO₂R¹³; C₁–C₁₈ alkyl which is substituted with one or more of the groups hydroxy, C₁–C₁₈ alkoxy, C₃–C₁₈ alkenoxy, halogen, phenoxy, C₁–C₁₈ alkyl-substituted phenoxy, C₁–C₁₈ alkoxy-substituted phenoxy, halogen-substituted phenoxy, —COOH, —COOR⁸, CONH₂, —CONHR⁹, —CON(R⁹)(R¹⁰), —NH₂, —NHR⁹, —N(R⁹)(R¹⁰), —NHCOR¹¹, —CN, —OCOR¹¹, C₂–C₅₀ alkyl which is interrupted by one or more oxygen atoms or carbonyl groups and optionally substituted by one or more substituents selected from the group consisting of hydroxy, C₁–C₁₂ alkoxy, and glycidyloxy; glycidyl; and cyclohexyl optionally substituted with hydroxyl or —OCOR¹¹; wherein R¹² is C₁–C₁₈ alkyl, C₂–C₁₈ alkenyl, phenyl, C₁–C₁₂ alkoxy, phenoxy, C₁–C₁₂ alkylamino; phenylamino, tolylamino or naphthylamino and R¹³ is C₁–C₁₂ alkyl, phenyl, naphthyl or C₇–C₁₄ alkylphenyl. Some of these, as well as substituted HALS, are described in U.S. Pat. No. 5,376,710, which is incorporated herein by reference for all purposes as if fully set forth.

Alternately and more preferably, each R group is independently selected from a polyoxyalkylene radical of the formula XIX

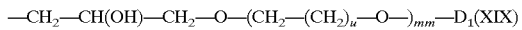

wherein D₁ is hydrogen,

—CH$_2$—CH$_2$—CH$_2$
    \\ /
     O or R$^{25}$;
a polyoxyalkylene radical of the formula XX $$\text{—CO—(CH}_2)_u\text{—O—(CH}_2\text{—(CH}_2)_u\text{—O—)}_{mm}\text{—D}_2 \quad (XX)$$

wherein D$_2$ is —(CH$_2$)$_u$—CO—R$^{22}$ or R$^{25}$;
a polyoxyalkylene radical of the formula XXI $$\text{—YY—O—CO—(CH}_2)_u\text{—O—(CH}_2\text{—(CH}_2)_u\text{—O—)}_{mm}\text{—D}_3 \quad (XXI)$$

wherein D$_3$ is —(CH$_2$)$_u$—CO—R$^{22}$ or R$^{25}$;
a polyoxyalkylene radical of the formula XXII $$\text{—(CH}_2)_{kk}\text{—CH(R}^{21})\text{—CO—B}_1\text{—(C}_{nn}\text{H}_{2nn}\text{—O—)}_{mm}\text{—C}_{nn}\text{H}_{2nn}\text{—}$$
$$\text{B}_1\text{—D}_4 \quad (XXII)$$

wherein D$_4$ is hydrogen of R$^{25}$;
a polyoxyalkylene radical of the formula XXIII $$\text{—CO—CH}_2\text{—CH}_2\text{—NH—(C}_{nn}\text{H}_{2nn}\text{—O—)}_{mm}\text{—C}_{nn}\text{H}_{2nn}$$
$$\text{—D}_5 \quad (XXIII)$$

wherein D$_5$ is —NH$_2$, —NH—(CH$_2$)$_2$—COO—R$^{23}$ or —O—R$^{25}$;
a polyoxyalkylene radical of the formula XXIV $$\text{—YY—O—CO—CH}_2\text{—CH}_2\text{—NH—(C}_{nn}\text{H}_{2nn}\text{—O—)}_{mm}\text{—}$$
$$\text{C}_{nn}\text{H}_{2nn}\text{—D}_5 \quad (XXIV)$$

wherein D$_5$ is as defined under formula (XXIII);
a polyoxyalkylene radical of the formula XXV $$\text{—(C}_{nn}\text{H}_{2nn}\text{—O—)}_{mm}\text{—C}_{nn}\text{H}_{2nn}\text{—D}_6 \quad (XXV)$$

wherein D$_6$ is —NH—CO—R$^{24}$, —OR$^{25}$, OH or H;
a polyoxyalkylene radical of the formula XXVI $$\text{—CH—CH}_2\text{—(OCH—CH}_2)_{\overline{m}}\text{—D}_7 \quad (XXVI)$$
$$\quad | \qquad \qquad | $$
$$\quad \text{R}^{17} \qquad \quad \text{R}^{17}$$

wherein D$_7$ is —OR$^{25}$, —NHCOR$^{24}$ or —OCH$_2$CH$_2$OR$^{25}$;
R$^{17}$ is C$_2$-C$_{10}$ alkyl, phenyl, naphthyl, diphenyl, or C$_2$-C$_6$ alkenyl,
methylenediphenylene, or C$_4$-C$_{15}$ alkylphenyl;
R$^{22}$ is halogen or —O—R$^{23}$;
R$^{24}$ is hydrogen, C$_1$-C$_{12}$ alkyl or aryl;
R$^{25}$ is C$_1$-C$_{16}$ alkyl, C$_5$-C$_{12}$ cycloalkyl, C$_3$-C$_6$ alkenyl, C$_1$-C$_{12}$ alkylaryl or aryl-C$_1$-C$_4$ alkyl;
m is an integer from 1 to 6; and
R$^{21}$, YY, B$_1$, kk, mm, nn and u are as defined above.

In preferred embodiments, those R$^1$ groups which are not either a group of the formula (V) or (VI) are independently selected from hydrogen, hydrocarbyl, functional hydrocarbyl, halogen, hydroxyl, —O(hydrocarbyl), —O(functional hydrocarbyl), —S(hydrocarbyl), —SO$_2$(hydrocarbyl), —SO$_3$(hydrocarbyl), —COO(hydrocarbyl), —CO(hydrocarbyl), —OCO(hydrocarbyl), —N(hydrocarbyl)(hydrocarbyl), —S(functional hydrocarbyl), —SO(functional hydrocarbyl), —SO$_3$(functional hydrocarbyl), —COO(functional hydrocarbyl), —CO(functional hydrocarbyl), —OCO(functional hydrocarbyl), —N(functional hydrocarbyl)(functional hydrocarbyl) or cyano, with the proviso that at least one such 3-position or 5-position R$^1$ group is a group of the formula (V) or (VI).

More preferably, each R$^1$ group is independently selected from hydrogen, a hydrocarbyl group of 1 to 24 carbon atoms, and a functional hydrocarbyl group of 1 to 24 carbon atoms, with the proviso that at least one such 3-position or 5-position R$^1$ group is a group of the formula (V) or (VI).

Even more preferably, each Such R$^1$ group is independently selected from hydrogen, an alkyl of 1 to 24 carbon atoms (which may optionally be substituted by one or more hydroxyl, carboxyl, carboalkoxy (ester), epoxy and/or amino groups and/or contain one or more carbonyl groups, oxygen atoms and/or nitrogen atoms in the chain); an alkenyl of 2 to 24 carbon atoms (which may optionally be substituted on a non-α-carbon by hydroxyl, carboxyl, epoxy and/or amino group(s) and/or contain carbonyl, oxygen and/or nitrogen in the chain), a cycloalkyl of 5 to 24 carbon atoms (which may optionally be substituted on a non-α-carbon by hydroxyl, carboxyl and/or amino group(s) and/or contain carbonyl, oxygen and/or nitrogen in the ring), and an aralkyl of 7 to 24 carbon atoms (which may optionally be substituted on a non-α-carbon by hydroxyl, carboxyl and/or amino group(s) and/or contain carbonyl, oxygen and/or nitrogen in the ring), with the proviso that at least one such 3-position or 5-position R$^1$ group is a group of the formula (V) or (VI).

Still more preferably, each R$^1$ group is independently selected from hydrogen, an alkyl of 1 to 24 carbon atoms optionally containing an oxygen atom in the chain, a hydroxyalkyl of 1 to 24 carbon atoms group optionally containing an oxygen atom in the chain, a group of the formula (V) and a group of the formula (VI), with the proviso that at least one such 3-position or 5-position R$^1$ group is a group of the formula (V) or (VI).

In preferred embodiments, each R$^2$ is independently selected from hydrogen, a hydrocarbyl group of 1 to 24 carbon atoms, a hydrocarbyloxy group of 1 to 24 carbon atoms and an acyloxy group of 1 to 24 carbon atoms. More preferably, each R$^2$ is independently selected from hydrogen, an alkyl of 1 to 24 carbon atoms optionally containing an oxygen atom in the chain; an alkyloxy of 1 to 24 carbon atoms optionally containing an oxygen atom in the chain; an alkenyl of 2 to 24 carbon atoms optionally containing an oxygen atom in the chain; an alkenyloxy of 2 to 24 carbon atoms optionally containing an oxygen atom in the chain; and an acyloxy group of 2 to 12 carbon atoms. Still more preferably, each R$^2$ is independently selected from hydrogen, an alkyl of 1 to 8 carbon atoms, an alkyloxy of 1 to 8 carbon atoms optionally containing an oxygen atom in the chain, a hydroxyalkyl of 1 to 8 carbon atoms group optionally containing an oxygen atom in the chain, a hydroxyalkyloxy of 1 to 8 carbon atoms group optionally containing an oxygen atom in the chain and an acyloxy of 2 to 12 carbon atoms. Especially preferred is when each R$^2$ is independently selected from hydrogen, an alkoxy of 1 to 4 carbon atoms and an alkyl of 1 to 4 carbon atoms and particularly hydrogen, methoxy and methyl.

In preferred embodiments, each $R^3$ is independently selected from hydrogen, a hydrocarbyl group of 1 to 24 carbon atoms, a functional hydrocarbyl group of 1 to 24 carbon atoms and —OR. More preferably, each $R^3$ is independently selected from hydrogen, an alkyl of 1 to 24 carbon atoms (which may optionally be substituted by hydroxyl, carboxyl and/or amino group(s) and/or contain carbonyl, oxygen and/or nitrogen in the chain); an alkenyl of 2 to 24 carbon atoms (which may optionally be substituted by hydroxyl, carboxyl and/or amino group(s) and/or contain carbonyl, oxygen and/or nitrogen in the chain); a cycloalkyl of 5 to 12 carbon atoms (which may optionally be substituted by hydroxyl, carboxyl and/or amino group(s) and/or contain carbonyl, oxygen and/or nitrogen in the ring); and —OR. Still more preferably, each $R^3$ is independently selected from hydrogen, an alkyl of 1 to 24 carbon atoms optionally containing an oxygen atom in the chain, a hydroxyalkyl of 1 to 24 carbon atoms group optionally containing an oxygen atom in the chain and —OR. Especially preferred is when each $R^3$ is independently selected from hydrogen, an alkyl of 1 to 4 carbon atoms and —OR; and particularly hydrogen, methyl and —OR.

In preferred embodiments, each $R^4$, $R^{4'}$ and $R^{4''}$ group is independently selected from hydrogen, a hydrocarbyl group of 1 to 24 carbon atoms, and a functional hydrocarbyl group of 1 to 24 carbon atoms. More preferably, each $R^4$, $R^{4'}$ and $R^{4''}$ is independently selected from hydrogen, an acyl of 2 to 12 carbon atoms, an acyloxy of 2 to 12 carbon atoms and a hydrocarbyl having from 1 to 12 carbon atoms. Still more preferably, each $R^4$, $R^{4'}$ and $R^{4''}$ is independently selected from hydrogen and an alkyl of 1 to 4 carbon atoms; and especially hydrogen.

In preferred embodiments, each of $R^5$ is independently hydrogen, a hydrocarbyl group of 1 to 24 carbon atoms. More preferably, each of $R^5$ is independently selected from hydrogen, an alkyl of 1 to 24 carbon atoms (which may optionally contain carbonyl and/or oxygen in the chain); an alkenyl of 2 to 24 carbon atoms (which may optionally contain carbonyl and/or oxygen in the chain); and a cycloalkyl of 5 to 12 carbon atoms (which may optionally contain carbonyl and/or oxygen in the ring), phenyl, aryl of 6 to 24 carbon atoms and aralkyl of 7 to 24 carbon atoms. Still more preferably, each of $R^5$ is independently hydrogen, an alkyl of 1 to 24 carbon atoms in the chain and especially an alkyl of 2 to 18 carbon atoms.

In certain preferred embodiments, each of $R^6$ and $R^7$ is independently selected from a hydrocarbyl group of 1 to 24 carbon atoms (which may optionally contain carbonyl and/or one or more oxygen atoms in the chain), with at least one of the hydrocarbyl groups being substituted by at least one of a hydroxyl, epoxy, glycidyloxy, —COOH, —COOR⁸, —O—COR⁸, —CR⁹=CH₂, —CO—CR⁹=CH₂, —NHR⁸ and a blocked isocyanate group. More preferably, each of $R^6$ and $R^7$ is independently selected from an alkyl group of 1 to 24 carbon atoms (which may optionally contain carbonyl and/or one or more oxygen atoms in the chain); an alkenyl group of 2 to 24 carbon atoms (which may optionally contain carbonyl and/or one or more oxygen atoms in the chain); a cycloalkyl group of 5 to 12 carbon atoms (which may optionally contain carbonyl and/or one or more oxygen atoms in the ring); an aryl group of 6 to 24 carbon atoms; and an aralkyl group of 7 to 24 carbon atoms, at least one of which groups is substituted as described above. Still more preferably, each of $R^6$ and $R^7$ is independently selected from an alkyl group of 1 to 24 carbon atoms (which may optionally contain carbonyl and/or one or more oxygen atoms in the chain), and an aralkyl group of 7 to 24 carbon atoms, and at least one of which is substituted by a hydroxyl, —CR⁹=CHR¹⁰ or —CO—CR⁹=CHR¹⁰. Alternately preferred is when each of $R^6$ and $R^7$ is independently selected from hydrogen, an alkyl group of 1 to 24 carbon atoms (which may optionally be substituted by hydroxyl), phenyl, and an aralkyl of 7 to 24 carbon atoms optionally substituted with —CR⁹=CH₂.

In preferred embodiments, $R^8$ is selected from: hydrogen and hydrocarbyl of 1 to 24 carbon atoms which may optionally be substituted by hydroxyl or alkoxy of 1 to 4 carbon atoms and/or contain one or more oxygen and/or nitrogen atoms in the chain. More preferably, $R^8$ is selected from: hydrogen and hydrocarbyl of 1 to 24 carbon atoms which may optionally be substituted by hydroxyl or alkoxy of 1 to 4 carbon atoms.

In preferred embodiments, $R^9$ is selected from: hydrogen and an alkyl of 1 to 4 carbon atoms. More preferably, $R^9$ is selected from: hydrogen and a methyl group.

In preferred embodiments, $R^{10}$ is selected from: hydrogen, a hydrocarbyl group of 1 to 8 carbon atoms, or phenyl. More preferably, $R^{10}$ is hydrogen or methyl.

$R^{11}$, when i is 1, is $R^1$.

When i is 2, $R^{11}$ is preferably a hydrocarbylene group of 1 to 24 carbon atoms. More preferably, $R^{11}$ is an alkylene of 1 to 24 carbon atoms (which may optionally be substituted by one or more hydroxyl, carboxyl, carboalkoxy (ester), epoxy and/or amino groups and/or contain one or more carbonyl groups, oxygen atoms and/or nitrogen atoms in the chain), an alkenylene of 2 to 24 carbon atoms (which may optionally be substituted by hydroxyl, carboxyl, epoxy and/or amino group(s) and/or contain carbonyl, oxygen and/or nitrogen in the chain), a cycloalkylene of 5 to 24 carbon atoms (which may optionally be substituted by hydroxyl, carboxyl and/or amino group(s) and/or contain carbonyl, oxygen and/or nitrogen in the ring), and an aralkylene of 7 to 24 carbon atoms (which may optionally be substituted by hydroxyl, carboxyl and/or amino group(s) and/or contain carbonyl, oxygen and/or nitrogen in the ring). Even more preferably, $R^{11}$ is selected from an alkylene of 1 to 24 carbon atoms optionally containing an oxygen atom in the chain, and a hydroxyalkylene of 1 to 24 carbon atoms optionally containing an oxygen atom in the chain. Still more preferably, $R^{11}$ is selected from methylene, i.e., (—CH₂—), alkylidene, i.e., (—CH(R$_i$)—), wherein R$_i$ is a linear or branched hydrocarbyl group of 1 to 24 carbon atoms, or mixtures thereof. Most preferably, $R^{11}$ is methylene.

Particularly preferred embodiments of the trisaryl-1,3,5-triazines of the general formula (I) are exemplified by the following structures (VII) through (XII):

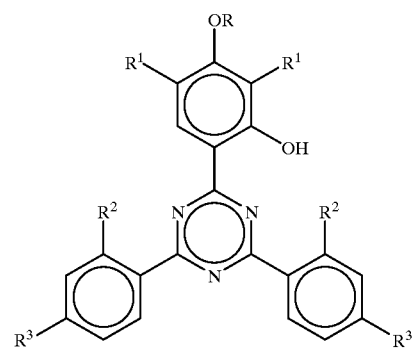

(VII)

(VIII)
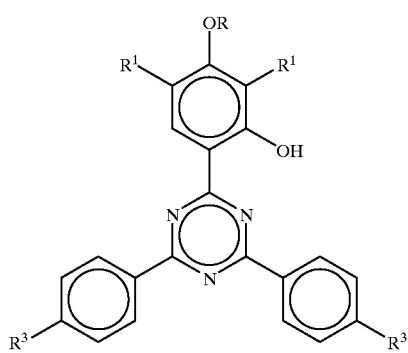
(IX)
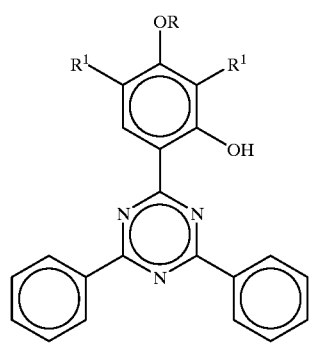
(XA)
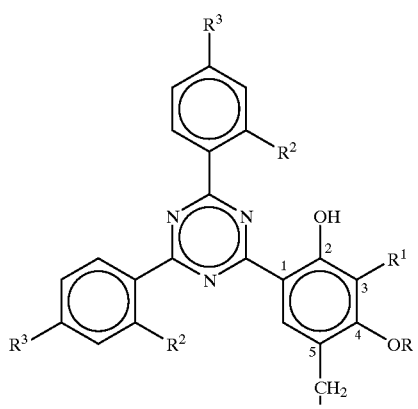
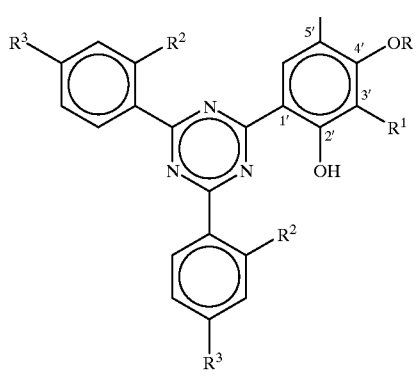
(XB)
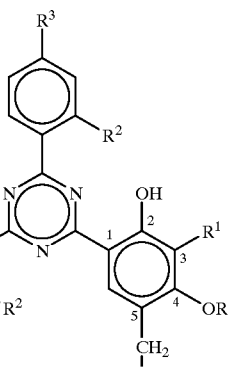
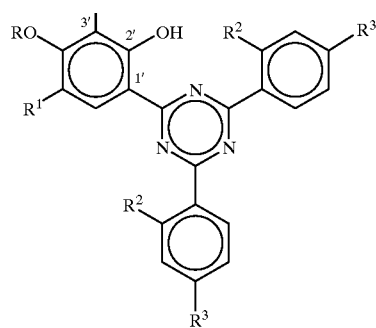
(XC)
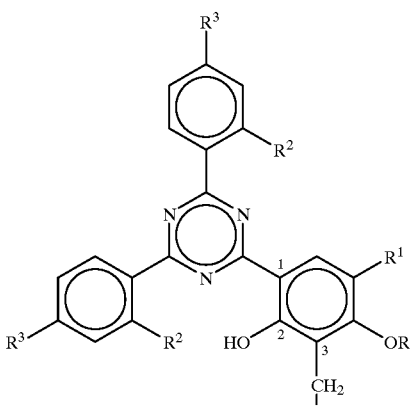
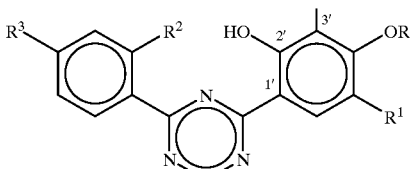
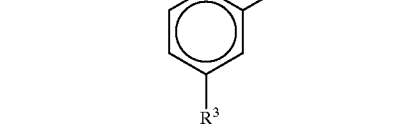

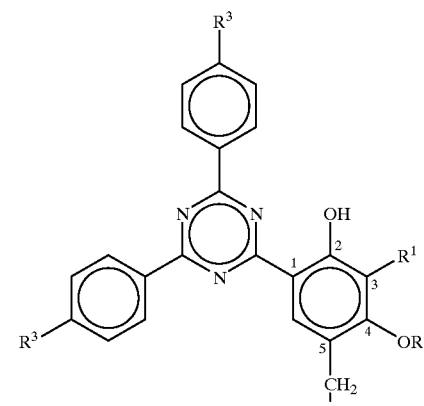
(XIA)
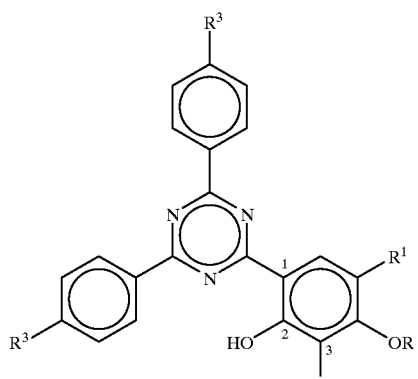
(XIC)
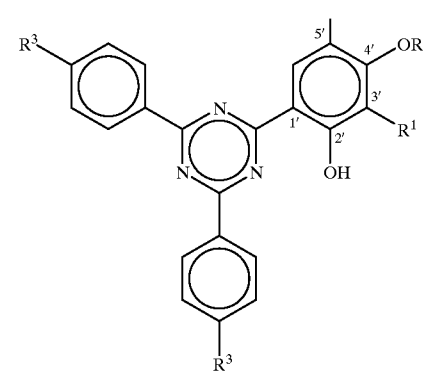
(XIB)
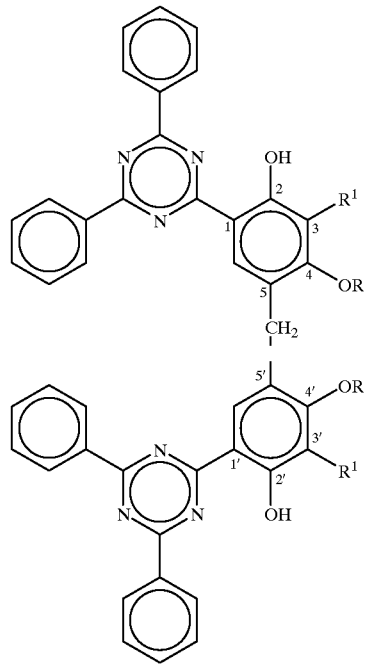
(XIIA)
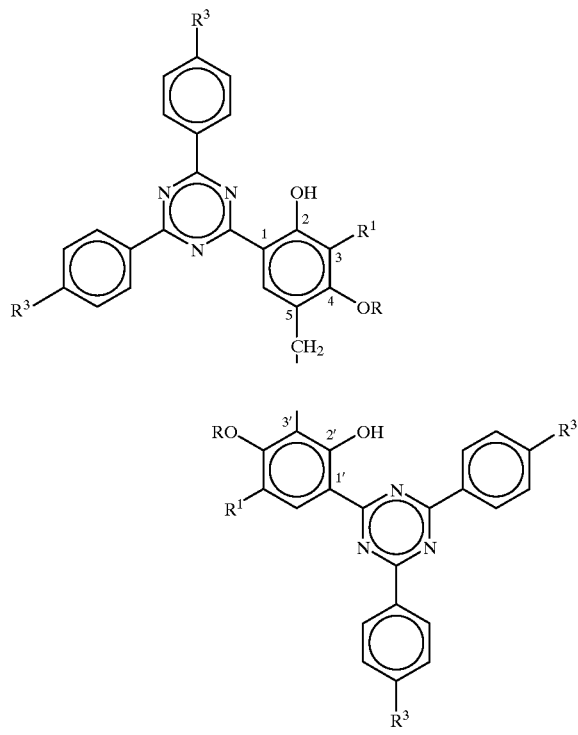
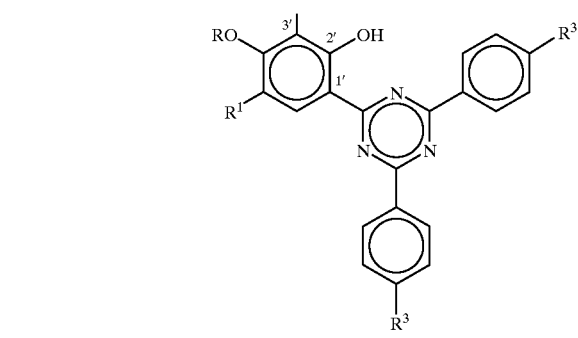

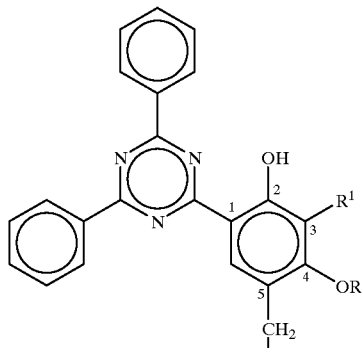
(XIIB)

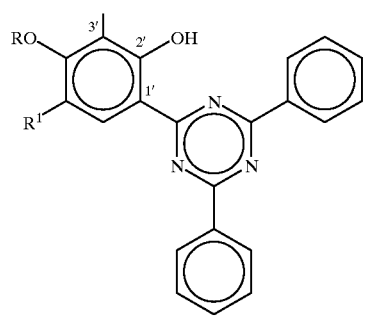

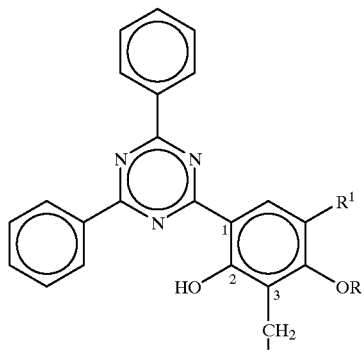
(XIIC)

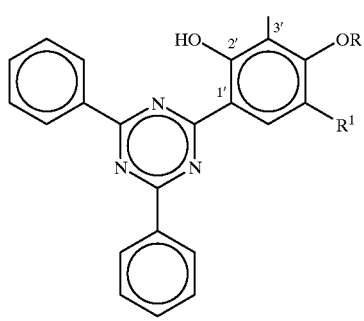

Structures (XA), (XIA) and (XIIA) are dimers formed by connecting two of structure (I) with an $R^{11}$ bridging group attached to the 5-position of each —OH/—OX bearing ring. Structures (XB), (XIB) and (XIIB) are dimers formed by connecting two of structure (I) with an $R^{11}$ bridging group attached to the 5-position of one —OH/—OX bearing ring and to the 3-position of one —OH/—OX bearing ring. Structures (XC), (XIC) and (XIIC) are dimers formed by connecting two of structure (I) with an $R^{11}$ bridging group attached to the 3-position of each —OH/—OX bearing ring.

Particularly preferred embodiments of the trisaryl-1,3,5-triazines of the general formula (II) are exemplified by the following structures (XIII), (XIV) and (XV):

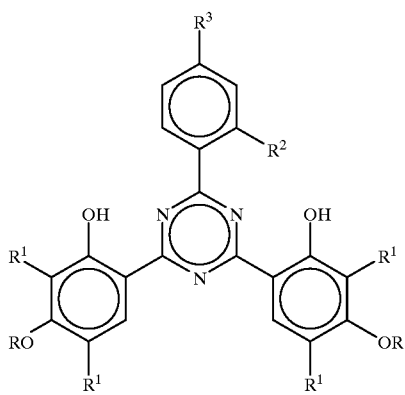
(XIII)

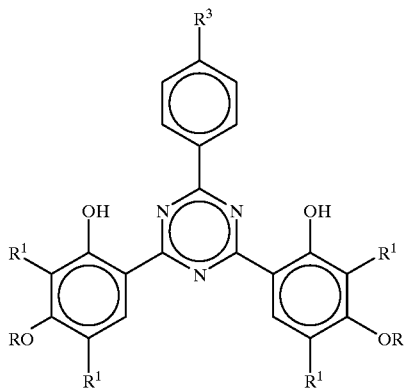
(XIV)

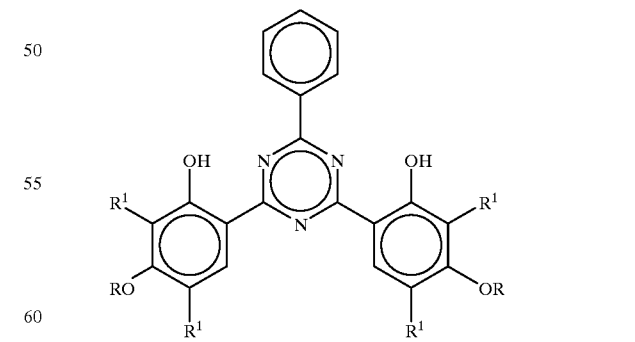
(XV)

Particularly preferred embodiments of the trisaryl-1,3,5-triazines of the general formula (III) are exemplified by the following structure (XVI):

(XVI)
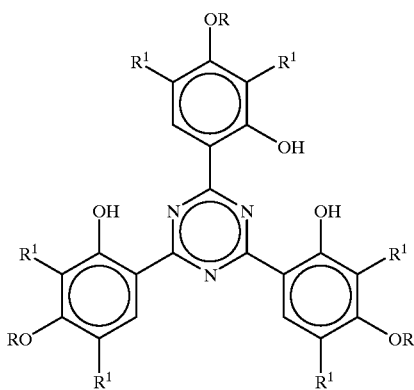
Particularly preferred embodiments of groups of the general formula (V) include the following:
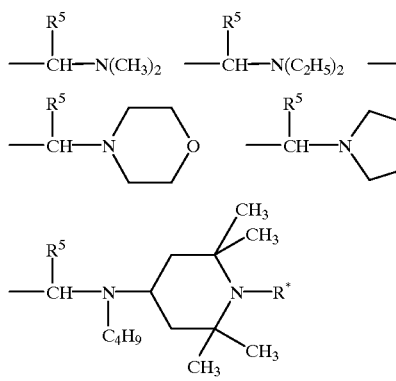
wherein R* is H, CH$_3$,
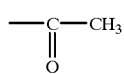
or
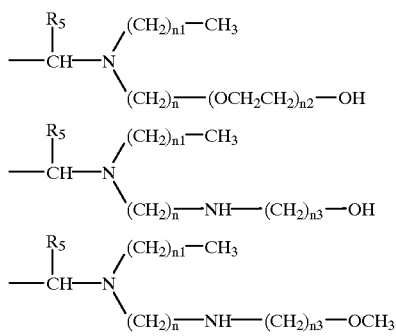
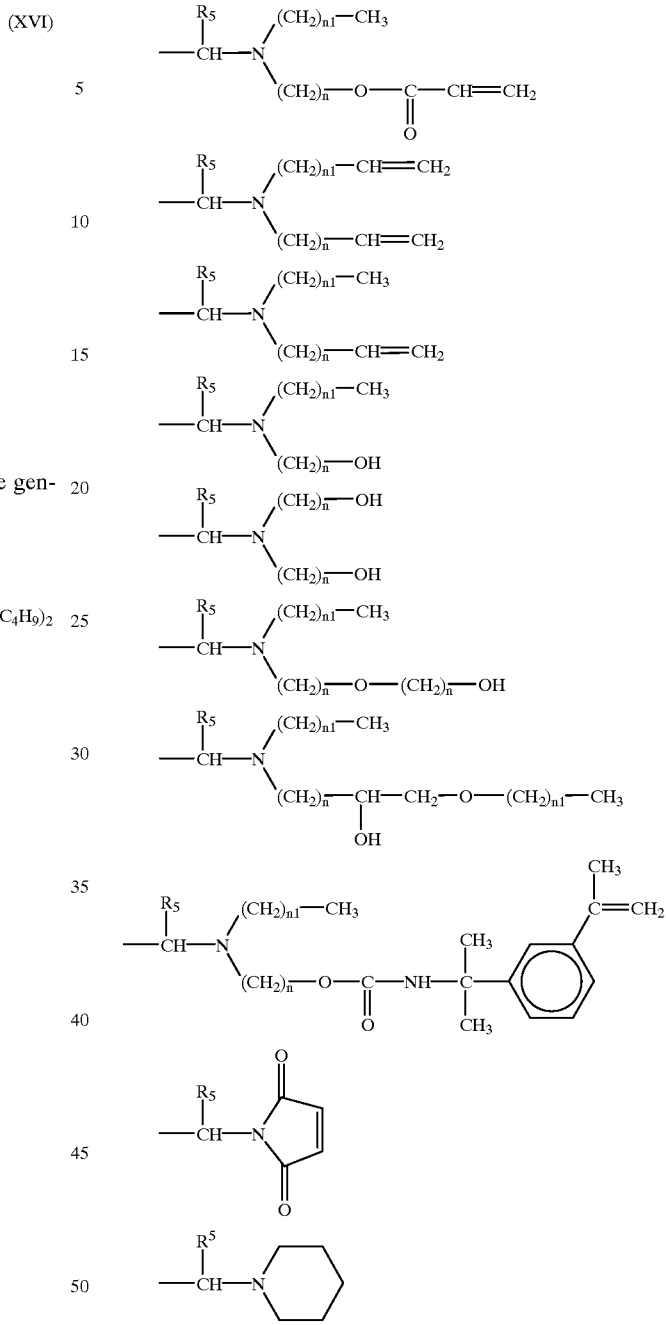
wherein n is 1–24 (preferably 1–8), n1 is 0–23 (preferably 0 to 17), n2 is 1–50 (preferably 1–10) and n3 is 1–24 (preferably 1 to 8).
Most preferred embodiments of groups of the general formula (V) include the following:
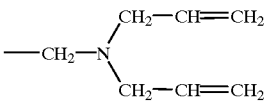

-continued

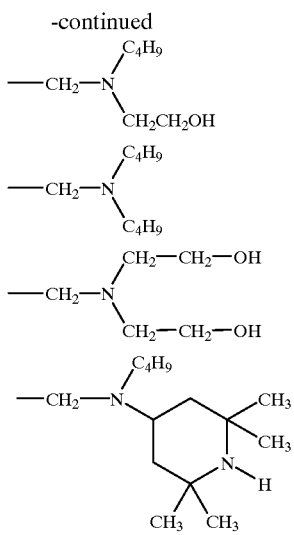

Particularly preferred embodiments of groups of the general formula (VI) include the following:

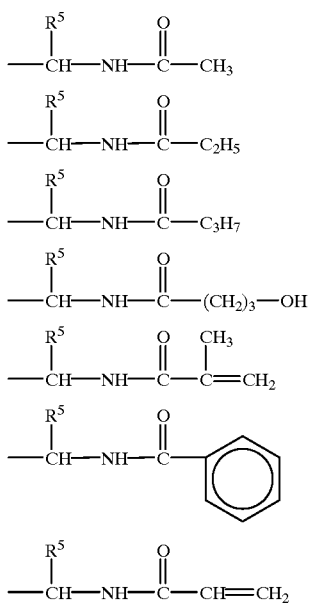

Most preferred embodiments of groups of the general formula (VI) include the following:

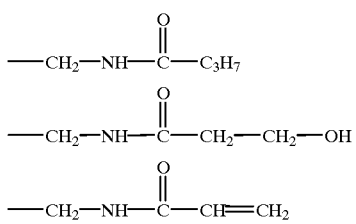

A further embodiment can be described as an amino resin adduct of the red-shifted trisaryl-1,3,5-triazines of the present invention. These adducts are produced by reacting an amino resin with a red-shifted trisaryl-1,3,5-triazines of the present invention to produce an amino resin with trisaryl-1,3,5-triazine chemically bound thereto. Such adducts are desirable because, for example, the gain in molecular weight imparted by bonding makes the adduct less volatile in polymeric compositions, thereby minimizing loss and toxicity. Related materials, known as aminoplast-anchored UV light stabilizers, have been described in U.S. Pat. No. 5,547,753.

The said amino resin adducts are formed from the red-shifted trisaryl-1,3,5-triazines of the present invention wherein at least one $R^6$ or $R^7$ is hydrogen; a hydrocarbyl group comprising hydroxyl, $—NH_2$, $—NHR^8$, $—C(O)NHR^8$, $—OC(O)NHR^8$, carboxyl or activated methylene; or a functional hydrocarbyl group comprising hydroxyl, $—NH_2$, $—NHR^8$, $—C(O)NHR^8$, $—OC(O)NHR^8$, carboxyl or activated methylene. The trisaryl-1,3,5-triazine may be in the form of a latent stabilizing compound as has been described above.

The amino resins are amino group-containing compounds are reacted with formaldehyde and alcohols to form aminoplast materials commonly used in coatings, moldings and adhesives, such as POWDERLINK® 1174, BEETLE® 80, CYMEL® 303, CYMEL® 1168, CYMEL® 370 and CYMEL® 1123, all available from Cytec Industries, Inc. In particular, CYMEL® 300 amino resin is preferred. The amino resin chemical group which generally reacts with said red-shifted trisaryl-1,3,5-triazine is typically an alkoxymethyl group, but other reactive groups such as hydroxy, halo, mercapto, sulfonyl, sulfonate, sulfate, phosphate, dialkylsulfonium, trialkylammonium and the like may also be used.

It should be noted that, in addition to the red-shifted trisaryl-1,3,5-triazines of the present invention, another type or types of stabilizer (viz., a mixture of stabilizers) may be bonded to the adducts of the present invention.

Methods of Preparation

The red-shifted trisaryl-1,3,5-triazines of the present invention can be prepared by a process which includes a primary amide, a secondary amine, including a Hindered Amine Light Stabilizer or HALS, and, optionally but preferably, a reagent used to provide a spacer group, for example formaldehyde, as reactants. For example, a compound corresponding to the formulas (I), (II) or (III), except where all $R^1$ groups and $R^{11}$ are hydrogen and i is 1, is reacted with an amine and formaldehyde to form a red-shifted trisaryl-1,3,5-triazine comprising a 3-position and/or a 5-position sustituent which comprises the amine or amide separated from the aryl ring by a methylene spacer group.

A preferred method for preparing a 3-position substituted monomeric red-shifted triazine with high selectivity comprises reacting a 2,4-dihydroxyphenyl substituted triazine with from about 1 to about 5 equivalents of a secondary amine or amide and from about 1 to about 5 equivalents of an aldehyde at a temperature of from about 25° C. to about 125° C. and for a time of from about 2 to about 48 hours.

For the following six preferred methods, the preferred reaction time is from about 4 to about 48 hr for all of the preferred methods described above.

A preferred method for preparing a 3,5-position disubstituted monomeric red-shifted triazine comprises reacting a 2,4-dihydroxyphenyl substituted triazine with from about 1 to about 5 equivalents of a secondary amine or amide and from about 1 to about 5 equivalents of an aldehyde at a temperature of from about 25° C. to about 125° C. and for a time of from about 2 to about 48 hours.

Another preferred method for preparing a 3,5-position disubstituted monomeric red-shifted triazine comprises reacting a 3-position substituted monomeric red-shifted triazine with from about 1 to about 5 equivalents of a secondary amine or amide and from about 1 to about 5 equivalents of an aldehyde at a temperature of from about 25° C. to about 125 ° C. and for a time of from about 2 to about 48 hours.

Another preferred method for preparing a 3,5-position disubstituted monomeric red-shifted triazine comprises reacting a 5-position substituted monomeric red-shifted triazine with from about 1 to about 5 equivalents of a secondary amine or amide and from about 1 to about 5 equivalents of an aldehyde at a temperature of from about 25° C. to about 125° C. and for a time of from about 2 to about 48 hours.

A preferred method for preparing a 3,5-position disubstituted dimeric red-shifted triazine comprises reacting a 2,4-dihydroxyphenyl substituted triazine with from about 1 to about 1.1 equivalents of a secondary amine or amide and from about 1.5 to about 5 equivalents of an aldehyde at a temperature of from about 25° C. to about 125° C. and for a time of from about 2 to about 48 hours.

Another preferred method for preparing a 3,5-position disubstituted dimeric red-shifted triazine comprises reacting a 3-position substituted monomeric red-shifted triazine of the present invention with from about 1 to about 5 equivalents of an aldehyde at a temperature of from about 25° C. to about 125° C. and for a time of from about 2 to about 48 hours.

A further preferred method for preparing a 3,5-position disubstituted dimeric red-shifted triazine comprises reacting a 5-position substituted monomeric red-shifted triazine with from about 1 to about 5 equivalents of an aldehyde at a temperature of from about 25° C. to about 125° C. and for a time of from about 2 to about 48 hours.

For all of the preferred methods described above, the reaction is preferably conducted with formaldehyde as the aldehyde. Moreover, for all of the preferred methods described above, the preferred temperature range is from about 80° C. to about 120° C.

Alternatively, an additional equivalent of formaldehyde and the same amine or a different amine can be used to form, in an optional second step, a red-shifted trisaryl-1,3,5-triazine comprising 3-position and 5-position sustituents where the amines are separated from the aryl ring by a methylene spacer group.

If the same amine is used in the optional second step, 3,5-disubstitution results. For obtaining unsymmetrically disubstituted trisaryl-1,3,5-triazines, a different amine is used in the second step than is used in the first step.

A typical general scheme for the preparation of the amino containing red-shifted trisaryl-1,3,5-triazines of the present invention is shown in equation (XVII).

Appropriate 3-position amido functionality can be imparted, for example, by performing the reaction exemplified in equation (XVII) except that the amine is replaced by a primary amide. If 3- and 5-position amido substitution is desired, the amine or amines of equation (XVII) are replaced by an amide or amides, since the amide used in the second step may be the same as or different than the amide used in the first step. If is the same, 3,5-disubstitution results.

Mixed amino and amido functionality can be imparted, for example using formaldehyde, by performing both steps of the reaction exemplified in equation (XVII) except by replacing the amine in one of the steps by an amide.

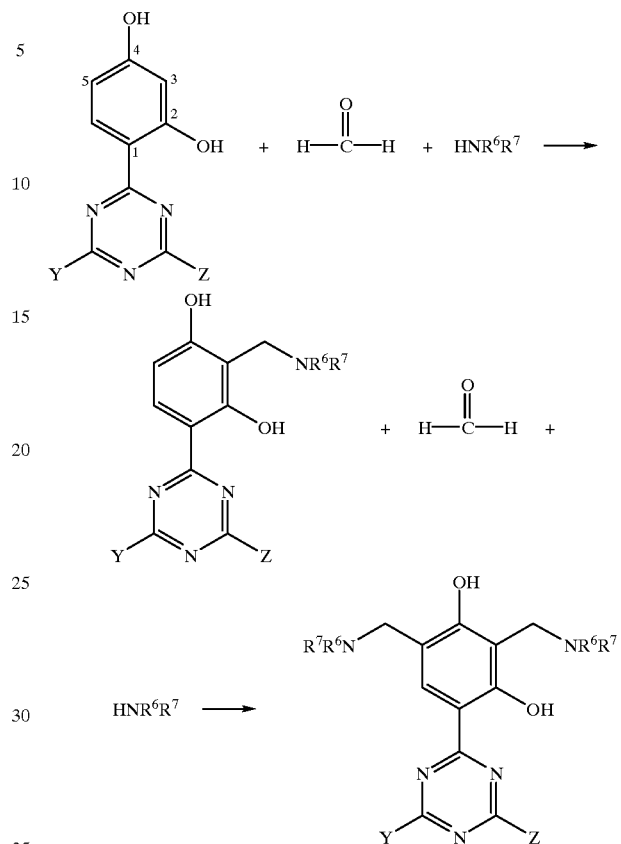

A bridged symmetrical red-shifted trisaryl-1,3,5-triazine of the present invention, i.e., a compound corresponding to the formulas (I), (II) or (III) where i is 2, can be prepared by a process which includes a primary or secondary amine and a reagent used to provide the bridging group, for example formaldehyde, as reactants. A typical general scheme for the preparation of bridged red-shifted trisaryl-1,3,5-triazines of the present invention is shown in equation (XVIII).

Optionally, at least a portion of the amine can be replaced by an amide to form a bridged red-shifted trisaryl-l,3,5-triazine of the present invention, some molecules of which will be symmetrical across the bridge and some molecules of which will be unsymmetrical.

Alternatively, the amine can be replaced by an amide to form a bridged symmetrical red-shifted trisaryl-1,3,5-triazine of the present invention.

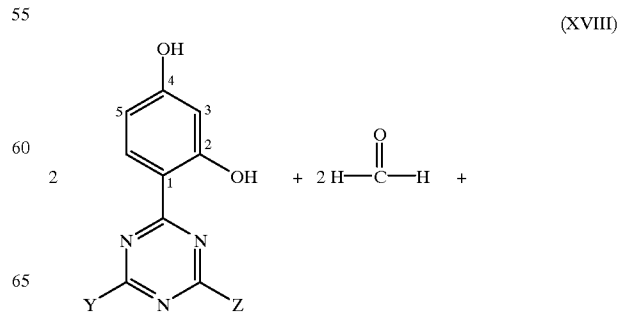

-continued

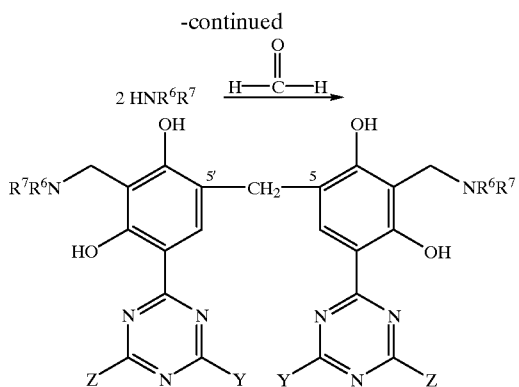

Unsymmetrical dimeric products can also be made by reacting the 3-substituted red-shifted trisaryl-1,3,5-triazines of the present invention with aqueous formaldehyde and different phenolic compounds including other classes of ultraviolet light absorbers, e.g., benzophenones and benzotriazoles.

At least one 4-hydroxyl group of any of these resorcinol-comprising triazines of the present invention must be unfunctionalized, i.e., be a free —OH group. The other hydroxyl groups may be appropriately functionalized, e.g., with a hydrocarbyl group or a functional hydrocarbyl group, by analogy to the procedures described in a number of the previously incorporated references such as U.S. Pat. No. 3,244,708 and EP-A-0434608. Functionalization of at least one 4-hydroxyl group may occur before or after the formation of any of the above-described triazines. Preferably, functionalization of the 4-hydroxyl group occurs after the formation of any of the above-described red-shifted trisaryl-1,3,5-triazines.

Uses of the Red-shifted Trisaryl-1,3,5-triazines

As indicated earlier, the novel red-shifted trisaryl-1,3,5-triazines of the present invention are particularly useful as ultraviolet light absorber agents for stabilizing a wide variety of materials including, for example, various polymers (both crosslinked and thermoplastic), photographic materials and dye solutions for textile materials, as well as in ultraviolet light screening agents (such as sunscreens). The novel red-shifted trisaryl-1,3,5-triazines of the present invention can be incorporated into such material in any one of a variety of conventional manners, including for example, physical mixing or blending, optionally, with chemical bonding to the material (typically to a polymer), as a component in a light stabilizing composition such as a coating or solution, or as a component in a UV screening composition such as a sunscreen composition.

In one embodiment of the present invention, the red-shifted trisaryl-1,3,5-triazines of the present invention can be employed to stabilize materials which are subject to degradation by ultraviolet radiation by incorporating the presently claimed compounds into polymeric materials, either chemically or physically. Non-limiting examples of polymeric materials that may be so stabilized are polyolefins; copolymers of one or more monoolefins and/or diolefins with carbon monoxide and/or with other vinyl monomers; hydrocarbon resins (such as C5–C9) including hydrogenated modifications thereof and mixtures of polyalkylenes and starch; polyesters; copolyether esters; polyethers; polyketones; polyamides and copolyamides derived from diamines, dicarboxylic acids and/or aminocarboxylic acids or the corresponding lactams; natural and synthetic rubbers and elastomers; polyurethanes; polystyrenes, poly-Δ-methylsytrenes and copolymers with other vinyl monomers; graft copolymers of styrene; high impact polystyrenes; polyacrylic acids, polymethacrylic acids, polyacrylates, polymethacrylates, polyacrylamides, polyacrylonitriles; homo- and copolymers derived from unsaturated alcohols and amines or the acyl derivatives or acetals thereof such as polyvinyl alcohol, polyvinyl acetate, polyacetals, and polybutyrals; homo- and copolymers of cyclic ethers such as alkylene glycols and alkylene oxides, as well as copolymers with bisglycidyl ethers; polybutadienes; polystyrenes; ABS (acrylate butadiene styrene); SAN (styrene acrylonitrile); ASA (acrylate styrene acrylonitrile); cellulosic acetate butyrate; cellulosic polymers; polyureas; polyimides; polyamide-imides; polyester-imides; polyether-imides; polyhydantoins; polybenzimidazoles; polyphenylsufide; PPO (polyphenylene oxide); polysulfones; polyether sulfones; polyether ketones; halogen-containing polymers; polyvinylchlorides; polycarbonates; polyester carbonates; thermoplastic TPOs; amino resin cross-linked polyacrylates and polyesters; polyisocyanate cross-linked polyesters and polyacrylates; phenol/formaldehyde, urea/formaldehyde and melamine/formaldehyde resins; drying and non-drying alkyd resins; alkyd resins; saturated and unsaturated polyester resins; cross-linkable acrylic resins derived from substituted acrylates such as epoxy acrylates, hydroxy acrylates, isocyanato acrylates, urethane acrylates or polyester acrylates; alkyd resins, polyester resins, and acrylate resins cross-linked with melamine resins, urea resins, isocyanates, isocyanurates, carbamates, or epoxy resins; cross-linked epoxy resins derived from aliphatic cycloaliphatic, heterocyclic and/or aromatic glycidyl compounds which are cross-linked with anhydrides or amines; polysiloxanes; Michael addition polymers of amines or blocked amines (e.g., ketimines) with activated unsaturated and/or methylene compounds such as acrylates and methacrylates, maleates, and acetoacetates; polyketimines in combination with unsaturated acrylic polyacetoacetate resins or with other unsaturated acrylic resins; radiation curable compositions; epoxymelamine resins; natural polymers such as cellulose, rubber, gelatin and chemically modified derivatives thereof; organic dyes and pigments; any mixture or blends of the above; cosmetic products; cellulose-based paper formulations; photographic film; paper; ink; and intraocular lenses.

Further non-limiting examples of specific polymers which may be stabilized include:

1. Homo- and copolymers of monoolefins and diolefins including but not limited to ethylene, propylene, isobutylene, butene, methylpentene, hexene, heptene, octene, isoprene, butadiene, hexadiene, dicyclopentadiene, ethylidene and cycloolefins such as cyclopentene and norbornene; for example, polyethylenes (which optionally can be crosslinked) such as high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE) and branched low density polyethylene (BLDPE).

2. Copolymers of one or more monoolefins and/or diolefins with carbon monoxide and/or with other vinyl monomers, including limited acrylic and methacrylic acid, acrylates and methacrylates, acrylamides, acrylonitriles, styrenes, vinyl acetate (such as ethylene/vinyl acetate copolymers), vinyl halides, vinylidene halides, maleic anhydride and allyl monomers such as allyl alcohol, allyl amine ally glycidyl ether and derivatives thereof.

3. Hydrocarbon resins (such as $C_5$–$C_9$) including hydrogenated modifications thereof and mixtures of polyalkylenes and starch.
4. Homo- and copolymers of styrenes such as styrene, p-methylstyrene and α-methylstyrene.
5. Copolymers of one or more styrenes with other vinyl monomers such as olefins and diolefins (e.g., ethylene, isoprene and/or butadiene), acrylic and methacrylic acid, acrylates and methacrylates, acrylamides, acrylonitriles, vinyl acetate (such as ethylene/vinyl acetate copolymers), vinyl halides, vinylidene halides, maleic anhydride and allyl compounds such as allyl alcohol, allyl amine allyl glycidyl ether and derivatives thereof.
6. Graft copolymers of styrenes on polybutadienes, polybutadiene/styrene copolymers and polybutadiene/acrylonitrile copolymers; styrene (or α-methylstyrene) and acrylonitrile (or methacrylonitrile) on polybutadiene; styrene and maleic anhydride on polybutadiene; styrene, acrylonitrile and maleic anhydride or maleimide on polybutadiene; styrene and acrylonitrile on ethylene/propylene/diene copolymers; styrene and acrylonitrile on polyalkyl acrylates or methacrylates; and styrene and acrylonitrile on acrylate/butadiene copolymers.
7. Halogen-containing polymers such as polychloroprene; chlorinated rubbers; chlorinated and brominated isobutylene/isoprene copolymers; chlorinated or sulfochlorinated polyethylene; copolymers of ethylene and chlorinated ethylene; epichlorohydrin polymers and copolymers; and polymers and copolymers of halogen-containing vinyl compounds such as vinyl chloride, vinylidene chloride, vinyl fluoride and/or vinylidene fluoride and other vinyl monomers.
8. Homo- and copolymers derived from α,β-unsaturated acids and derivatives thereof such as acrylic acid, methacrylic acid, acrylates, methacrylates, acrylamides and acrylonitriles.
9. Copolymers of the monomers mentioned in (8) with other unsaturated monomers such as olefins and diolefins (e.g., butadiene), styrenes, vinyl halides, maleic anhydride and allyl monomer such as allyl alcohol, allyl amine, allyl glycidyl ether and derivatives thereof.
10. Homo- and copolymers derived from unsaturated alcohols and amines or the acyl derivatives or acetals thereof, such as vinyl alcohol, vinyl acetate, vinyl stearate, vinyl benzoate, vinyl maleate, vinyl butyral, allyl alcohol, allyl amine, allyl glycidyl ether, allyl phthalate and allyl melamine; as well as copolymers of such monomers with other ethylenically unsaturated monomers mentioned above.
    For the preceding groups 1–10 of polymers, the present invention further encompasses these polymers as prepared by metallocene catalysts.
11. Homo- and copolymers of cyclic ethers such as alkylene glycols and alkylene oxides, as well as copolymers with bisglycidyl ethers.
12. Polyacetals such as polyoxymethylene and those polyoxymethylenes which contain ethylene oxide as a comonomer; and polyoxymethylenes modified with thermoplastic polyurethanes, acrylates and/or MBS.
13. Polyphenylene oxides and sulfides.
14. Polyurethanes derived from hydroxy-functional components such as polyhydric alcohols, polyethers, polyesters, polyacrylics and/or polybutadienes on the one hand, and aliphatic and/or aromatic isocyanates on the other, as well as precursors thereof.
15. Polyamides and copolyamides derived from diamines, dicarboxylic acids and/or aminocarboxylic acids or the corresponding lactams, such as polyamide 4, polyamide 6, polyamide 6/6, polyamide 6/10, polyamide 6/9, polyamide 6/12, polyamide 4/6, polyamide 12/12, polyamide 11 and polyamide 12; aromatic polyamides starting from m-xylene diamine and adipic acid; polyamides prepared from hexamethylene diamine and isophthalic and/or terephthalic acid and with or without an elastomer as a modifier, for example, poly-2,4,4-trimethylhexamethylene terephthalamide or poly-m-phenylene isophthalamide; block copolymers of the aforementioned polyamides with polyolefins, olefin copolymer, ionomers, chemically bonded or grafted elastomers, or polyethers such as polyethylene glycol, polypropylene glycol or polytetramethylene glycol; and polyamides condensed during processing (RIM polyamide systems).
16. Polyureas, polyimides, polyamide-imides, polyetherimides, polyesterimides, polyhydantoins and polybenzimidazoles.
17. Polyesters derived from dicarboxylic acids, diols and/or hydroxycarboxylic acids or the corresponding lactones, such as polyethylene terephthalate, polybutylene terephthalate, poly-1,4-dimethylcyclohexane terephthalate and polyhydroxybenzoates, as well as block copolyether esters derived from hydroxyl-terminated ethers; PETG; PEN; PTT; and also polyesters modified with polycarbonate or MBS.
18. Polycarbonates and polyester carbonates.
19. Polysulfones, polyether sulfones and polyether ketones.
20. Crosslinked polymers derived from aldehydes condensation resins such as phenol/formaldehyde resins, urea/formaldehyde resins and melamine/formaldehyde resins.
21. Drying and non-drying alkyd resins.
22. Unsaturated polyester resins derived from copolyesters of saturated and unsaturated dicarboxylic acids with polyhydric alcohols and vinyl compounds as crosslinking agents and also halogen-containing modifications thereof.
23. Crosslinkable acrylic resins derived from substituted acrylates such as epoxy acrylates, hydroxy acrylates, isocyanato acrylates, urethane acrylates or polyester acrylates.
24. Alkyd resins, polyester resins and acrylate resins crosslinked with melamine resins, urea resins, isocyanates, isocyanurates, carbamates or epoxy resins.
25. Crosslinked epoxy resins derived from aliphatic, cycloaliphatic, heterocyclic and/or aromatic glycidyl compounds such as bisphenol A and bisphenol F, which are crosslinked with hardeners such as anhydrides or amines.
26. Natural polymers such as cellulose, rubber, gelatin and chemically modified homologous derivatives thereof, including cellulose acetates, cellulose propionates and cellulose butyrates, or the cellulose ethers such as methyl cellulose, as well as rosins and their derivatives.
27. Polysiloxanes.
28. Michael addition polymers of amines or blocked amines (e.g., ketimines) with activated unsaturated and/or methylene compounds such as acrylates and methacrylates, maleates and acetoacetates.
29. Mixtures or blends of any of the above, such as PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylate, POM/thermoplastic PUR, PC/thermoplastic polyurethane, POM/acrylate, POM/MBS, PPO/HIPS, PPO/PA6.6 and copolymers, PATENT/HDPE, PP/HDPEF, PP/LDPE, LDPE/HDPE, LDPE/EVA, LDPE/EAA, PATENT/PP, PATENT/PPO, PBT/PC/ABS, PBT/PET/PC and the like.

30. Polyketimines in combination with unsaturated acrylic polyacetoacetate resins or with unsaturated acrylic resins including urethane acrylates, polyether acrylates, vinyl or acryl copolymers with pendant unsaturated groups and acrylated melamines.
31. Radiation curable compositions containing ethylenically unsaturated monomers or oligomers and a polyunsaturated aliphatic oligomer.
32. Epoxymelamine resins such as light-stable epoxy resins cross-linked by an epoxy functional coetherified high solids melamine resin.

Other materials which can be stabilized include, for example:

33. Naturally occurring and synthetic organic materials which may be mixtures of compounds, including mineral oils, animal and vegetable fats, oils and waxes, or oils, fats or waxes based on synthetic esters (e.g., phthalates, adipates, phosphates or trimellitates) and also mixtures of synthetic esters with mineral oils in any ratio.
34. Aqueous emulsions of natural or synthetic rubber such as natural latex or lattices of carboxylated styrene/butadiene copolymers.
35. Organic dyes such as azo dyes (diazo, triazo and polyazo), anthraquinones, benzodifuranones, polycyclic aromatic carbonyl dyes, indigoid dyes, polymethines, styryl dyes, di- and triaryl carbonium dyes, phthalocyanines, quinophthalones, sulfur dyes, nitro and nitroso dyes, stilbene dyes, formazan dyes, quinacridones, carbazoles and perylene tetracarboxylic diimides.
36. Cosmetic products, such as skin lotions, collagen creams, sunscreen, facial make-up, etc., comprising synthetic materials such as antioxidants, preservatives, lipids, solvents, surfactants, colorants, antiperspirants, skin conditioners, moisturizers etc.; as well as natural products such as collagen, proteins, mink oil, olive oil, coconut oil, carnauba wax, beeswax, lanolin, cocoa butter, xanthan gum, aloe, etc.
37. Cellulose-based paper formulations for use, e.g., in newsprint, cardboard, posters, packaging, labels, stationery, book and magazine paper, bond typing paper, multi-purpose and office paper, computer paper, xerographic paper, laser and ink-jet printer paper, offset paper, currency paper, etc.
38. Photographic film paper.
39. Ink.

Aliphatic Polyamide

The novel red-shifted trisaryl-1,3,5-triazines of the present invention can also be used with aliphatic polyamide polymers. An "aliphatic polyamide" is a polyamide characterized by the presence of recurring carbonamide groups as an integral part of the polymer chain which are separated from one another by at least two aliphatic carbon atoms. Illustrative of these polyamides are those having recurring monomeric units represented by the general formula:

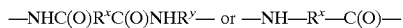

or a combination hereof in which $R^x$ and $R^y$ are the same or different and are alkylene groups of at least about two carbon atoms, preferably alkylene having from about 2 to about 12 carbon atoms. Exemplary of such polyamides are polyamides formed by the reaction of diamines and diacids such as poly (tetramethylene adipamide)(nylon 4,6); poly (hexamethylene adipamide) (nylon 6,6); poly (hexamethylene azelamide) (nylon 6,9); poly (hexamethylene sebacamide) (nylon 6,10); poly (heptamethylene pimelamide) (nylon 8,8); poly (nonamethylene azelamide) (nylon 9,9); poly (decamethylene azelamide) (nylon 10,9); and the like. Also illustrative of useful aliphatic polyamides are those formed by polymerization of amino acids and derivatives thereof, as for example lactams. Illustrative of these useful polyamides are poly(4-aminobutyric acid) (nylon 4); poly(6-aminohexanoic acid) (nylon 6); poly(7-aminoheptanoic acid) (nylon 7); poly(8-aminoocatanoic acid) (nylon 8); poly(9aminononanoic acid) (nylon 9); poly(10-aminodecanoic acid) (nylon 10); poly(11-aminoundecanoic acid) (nylon 11); poly(12-aminododecanoic acid) (nylon 12); and the like. Blends of two or more aliphatic polyamides may also be employed.

Copolymers formed from any combination of the recurring units of the above referenced aliphatic polyamides can be used. By way of illustration and not limitation, such aliphatic polyamide copolymers include caprolactam/hexamethylene adipamide copolymer (nylon 6/6,6); hexamethylene adipamide/caprolactam copolymer (nylon 6, 6/6); hexamethylene adipamide/hexamethylene-azelamide copolymer (nylon 6,6/6,9); and copolymers formed from recurring units of the above referenced aliphatic polyamides with aliphatic/aromatic polyamide recurring units may also be used. Examples of such copolyamides are nylon 6/6T; nylon 6,6/6, T; nylon 6/10T; nylon 6/12T; nylon 6,10/6, T; etc.

Preferred aliphatic polyamides for use in the practice of this invention are poly(caprolactam); poly(7-aminoheptanic acid); poly(tetramethylene adipamide); poly(hexamethylene adipamide); and mixtures thereof. The particularly preferred aliphatic polyamides are poly(caprolatam); poly (hexamethylene adipamide); poly(tetramethylene adipamide); and mixtures thereof.

Aliphatic polyamides useful in the practice of this invention may be obtained from commercial sources or prepared in accordance with known preparatory techniques. For example, polycaprolactam may be obtained from Allied Signal Inc. and poly(hexamethylene adipamide) may be obtained from DuPont Co.

The number average molecular weight of the aliphatic polyamide may vary widely. Usually, the aliphatic polyamide is of film forming molecular weight that is sufficiently high to form a free standing film and sufficiently low to allow melt processing of the blend into a film. Such number average molecular weights are well known to those of skill in the film art and are usually at least about 5,000 as determined by the formic acid viscosity method. In this method, a solution of 9.2 wt. Concentration of aliphatic polyamide in 90% formic acid at 25° C. is used. In the preferred embodiments of the invention, the number average molecular weight of the aliphatic polyamide is from about 5,000 to about 1,000,000 and in the particularly preferred embodiments is from about 10,000 to about 100,000. Amongst the particularly preferred embodiments, most preferred are those in which the molecular weight of the aliphatic polyamide is from about 20,000 to about 40,000.

Polyurethane

Polyurethane (PUR) elastomer products ("Spandex") can be stabilized against discoloration and loss of elasticity during UV light exposure with combinations of UV absorbers according to the invention and hindered amine light stabilizers. Spandex fibers is a PUR elastomer product, which requires very specific UV absorber and hindered amine light stabilizers properties in order to achieve optimum performance. UV absorbers of the triazine class of this invention can be combined with polymeric hindered amine light stabilizers (HALS) to provide outstanding performance in achieving the desired properties for the Spandex fiber applications.

The triazine UV absorber of the invention, used alone or in combination with HALS provides the following properties in the Spandex fiber application: (1) low color contribution at typical use levels in the 0.5–2.0% range; (2) sufficient MW, thermal stability and low volatility for fiber processing and thermal exposure conditions; (3) high compatibility and permanence; (4) prevent discoloration and loss of elasticity during exposure to UV light energy; (5) low extraction by water and dry cleaning solvents; (6) low color development during exposure to atmospheric pollutants, $NO_x$, $SO_x$, hydrocarbons, etc.; (7) low interaction with sea water and pool chemicals; (8) low interaction and color development with typical phenolic antioxidants used for the thermal stabilization of Spandex fibers; and (9) low interaction with copper based antioxidant systems used in nylon fibers for nylon/Spandex fabrics.

The triazine UV absorber with or without the polymeric HALS provides outstanding stabilization with minimum negative effect on secondary performance properties, such as low color development during $NO_x$ exposure and low interaction with copper based antioxidant systems using in nylon fibers.

As noted above, any of the triazine compounds disclosed herein can be used to impart one or more of the properties described above to Spandex fibers when added thereto in a stabilization effective amount.

Preferably, these triazine compounds are added in combination with polymeric HALS. The polymeric HALS is preferably poly[(6-morpholino-s-triazine-2,4-diyl)[2,2,6,6,-tetramethyl-4-piperidyl)imino]-hexamethylene [(2,2,6,6-tetramethyl-4-piperidyl)imino]]. Most preferably, the polymeric HALS is the methylated (M) version of the above HALS, which is sold by Cytec Industries, Inc. as CYASORB®UV-3529 light stabilizer. Other polymeric HALS disclosed in U.S. Pat. No. 4,331,586 are also suitable.

Spandex fibers are made from a polyurethane (PUR) prepolymer prepared from a diisocyanate and a glycol. There are four basic processes used to convert the PUR prepolymer into the fiber product. These processes are solution dry spinning, solution wet spinning, melt extrusion, and reaction spinning. The above UV stabilizer alone or in combination with HALS would be suitable for use in any or all four processes.

Spandex fibers may contain a processing antioxidant system, such as a phenolic antioxidant, or a phenolic/phosphite antioxidant combination. In addition, pigments, such as $TiO_2$ are commonly used in the fiber products.

The triazine UV absorber alone or with M-HALS can be dissolved into DMF or DMAC and added to the PUR prepolymer solution prior to solution fiber spinning processes. Also, the combination can be extrusion compounded into the PUR compound used in the melt spinning process.

Polycarbonates

Among polymeric compounds, preference is given to the polycarbonates, polyesters, polyamides, polyacetals, polyphenylene oxides and polyphenylene sulfides, but especially to the polycarbonates. Those compounds are to be understood as being especially those polymers the constitutional repeating unit of which corresponds to the formula:

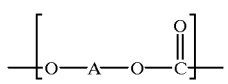

wherein A is a divalent phenolic radical. Examples of A are given inter alia in U.S. Pat. No. 4,960,863 and DE-A-3 922,496. A can be derived, for example, from hydroquinone, resorcinol, dihydroxybiphenylene or bisphenols in the broadest sense of the term, such as bis(hydroxyphenyl) alkanes, cycloalkanes, sulfides, ethers, ketones, sulfones, sulfoxides, α,α'-bis(hydroxyphenyl)-diisopropylbenzenes, for example the compounds 2,2-bis(4-hydroxyphenyl) propane, 2,2-bis(3,5-dimethyl-4-hydroxyphenyl)-propane, 2,2-bis(3,5-dichloro-4-hydroxyphenyl)propane, 1,1-bis(4-hydroxyphenyl)cyclohexane, or from the compounds of the formulae:

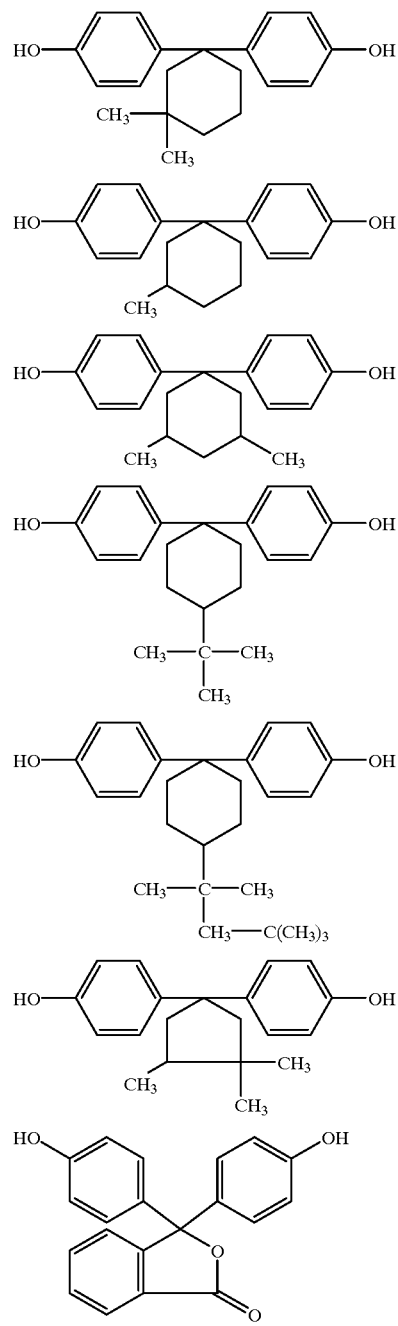

-continued

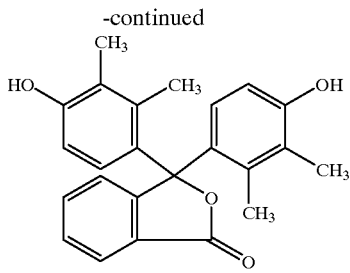

In one embodiment, the preferred resins are polycarbonates based on dihydric phenols such as 2,2-bis-(4-hydroxyphenyl)propane (bisphenol A); 2,4-bis(4-hydroxyphenyl)-2-methylbutane; 1,1-bis-(4-hydroxyphenyl)-cyclohexane; 2,2-bis-(3-chloro-4-hydroxyphenyl)propane; 4,4'-sulfonyldiphenol; and 1,1-bis-(4-hydroxyphenyl)-3,3,5-trimethylcyclohexane.

Also preferred are polycarbonate copolymers incorporating two or more phenols, branched polycarbonates wherein a polyfunctional aromatic compounds is reacted with the dihydric phenol(s) and carbonate precursor, and polymer blends of which polycarbonate comprises a significant portion of the blend.

The most preferred resins for both layers are polycarbonates based on bisphenol A.

U.S. Pat. No. 5,288,788 also describes polycarbonates and polyester carbonates, especially aromatic polycarbonates, for example those based on 2,2-bis(4-hydroxyphenyl) propane or 1,1-bis(4-hydroxyphenyl)cyclohexane.

British Patent Appn. No. 2,290,745 describes a number of methods have been developed to concentrate UV absorbers near or at the surface of polymeric materials. These include surface impregnation (see U.S. Pat. Nos. 3,309,220, 3,043,709, 4,481,664 and 4,937,026) and coating a plastic article with solutions containing thermoplastic resins and UV absorbers (see U.S. Pat. Nos. 4,668,588 and 4,353,965). Both techniques suffer from drawbacks including requiring additional processing steps (i.e. applying, drying or curing), and encounter difficulties associated with the handling of large processed articles. An additional drawback, particularly relevant to polycarbonate sheet production, is the detrimental effect such post addition treatment would have on the surface of the polymeric substrate.

As described in the U.S. Pat. No. 5,445,872, application of surface layers via coextrusion takes place in a known manner in known coextrusion equipment as taught in U.S. Pat. Nos. 3,487,505 and 3,557,265. Coextrusion is a well recognized method of producing laminated thermoplastic materials by simultaneously extruding various numbers of layers which form a single composite material. U.S. Pat. No. 4,540,623 describes coextruded materials of at least forty layers. Other methods produce as few as two or three different layers.

In one embodiment, the invention also relates to thermoplastic articles coated with a thermoplastic layer 0.1 to 10 mil (0.00254 mm to 0.254 mm), preferable 0.1 to 5 mil (0.00254 mm to 0.127 mm), thick, in which said layer contains 0.1% to 20% by weight of the red-shifted trisaryl-1,3,5-triazines of the present invention. Preferred concentrations of are 2% to 15% by weight; most preferred concentrations of 5% to 10% by weight.

The red-shifted trisaryl-1,3,5-triazines of the present invention may be incorporated into the thermoplastics of the surfaces layer by standard methods such as dry mixing the additives with granular resin prior to extruding.

The red-shifted trisaryl-1,3,5-triazine layer may be applied to one or both sides of the thermoplastic article.

Laminated thermoplastic articles which contain additional layers such as a water resistant layer as found in U.S. Pat. No. 4,992,322 are also part of the present invention.

The core layer and the coating layer may be of the same thermoplastic resin or different thermoplastic polyesters, polyester carbonates, polyphenylene oxide, polyvinyl chloride, polypropylene, polypropylene, polyethylene, polyacrylates, polymethacrylates and copolymers and blends such as styrene and acrylonitrile on polybutadiene and styrene with maleic anhydride.

Mixtures (polyblends) of such polymers with one another or with other polymers, for example with polyolefins, polyacrylates, polydienes or other elastomers in the form of impact strength modifiers.

The red-shifted trisaryl-1,3,5-triazines of the present invention can also be chemically bonded to substrates, such as polymers, thereby greatly reducing the migration of such UV absorbers, e.g., out of the substrate or away from the substrate surface. The bonding mechanism of the triazines of the present invention involves the formation of a bond (chemical and/or co-valent) between a functionality attached to the amido or carbamate group, e.g., by a pendant vinyl or hydroxyl group, and the "host" substrate, such as a polymer.

Incorporation of the red-shifted trisaryl-1,3,5-triazines of the invention can be brought about by copolymerization, copolyaddition, copolycondensation, by reaction with a polymer which carries suitable functional groups, or by grafting, in a manner as disclosed in U.S. Pat. Nos. 3,423,360 and 5,189,084 which are incorporated herein by reference as if fully set forth.

Bonding of the red-shifted trisaryl-1,3,5-triazines of the invention can occur by polymerization or copolymerization. In the case of the novel triazines of the present invention comprising pendant vinyl groups, polymerization or copolymerization with at least one vinyl monomer, e.g., (meth) acrylic acid, esters of (meth)acrylic acid such as methyl acrylate, amides of (meth)acrylic acid, hydroxyethylacrylate, olefins, vinyl chloride, styrene, butadiene, isoprene and acrylonitrile can be carried out to form homopolymers or copolymers in which the vinyl group is incorporated into the backbone of the polymer. Polymerization or copolymerization can be initiated by initiators, such as free radical, anionic and cationic types, or by actinic radiation, such as UV, electron beam, x-rays and gamma irradiation from a $Co^{60}$ source, as is well known to those in the polymerization art. Polymerization or copolymerization can be carried out in solution, in an emulsion, in a dispersion, in the melt, or in the solid state as is well known to those in the polymerization art.

Also, bonding of the presently claimed red-shifted trisaryl-1,3,5-triazine compounds of the present invention can be brought about by copolyaddition or copolycondensation. Such incorporation can be made by addition during the synthesis of an addition polymer or copolymer or by condensation during the synthesis of a condensation polymer or copolymer by methods known to those skilled in the art. For example, compounds of the formulas (I)–(III) containing the appropriate functional groups can be incorporated into polyesters, polyamides, polyurethanes, epoxy resins, melamine resins, alkyd resins, phenolic resins, polyurethanes, polycarbonates, polysiloxanes, polyacetals and polyanhydrides, to name but a few.

In addition, compounds of the formulas (I)–(III) can be bonded to a monomeric component which is then incorporated into a polymer or copolymer, e.g., by the free radical initiated addition or copolycondensation methods described above. Analogous methods are disclosed in, for example, U.S. Pat. No. 5,459,222 (incorporated by reference herein for all purposes as if fully set forth) for the bonding of benzotriazole and benzophenone stabilizers to diol precursors which are then incorporated by condensation polymerization into polyurethanes and polyesters to impart UV stabilizing properties to said polymers.

Alternately, the red-shifted trisaryl-1,3,5-triazines of the invention may also be bonded to polymers by reaction with an oligomer and/or polymer which carries suitable functional groups. For example, at least one triazine compound comprising a vinyl pendant group can be added, optionally with at least one other vinyl monomer or compound comprising a vinyl group, to unsaturated polyester resins, unsaturated polybutadiene oligomers or unsaturated rubbers and then cured by actinic radiation or by a free radical catalyst. Or, at least one triazine compound comprising a terminal functional group, such as hydroxyl or amido, may be reacted with a polymer and/or oligomer such as polyesters, polyurethanes and polydiols with reactive end-groups, partially hydrolyzed polyvinylacetate, epoxy resins, polysiloxanes and polymers comprising maleic anhydride, either in the main chain or as a side-chain, by methods analogous to those well known to those of ordinary skill in the art.

Grafting is yet another way of bonding of the presently claimed red-shifted trisaryl-1,3,5-triazines to polymers and/or oligomers. Grafting may be carried out in solution, in the melt, or in the solid state with the initiators or actinic radiation types discussed above for polymerization when, for example, the novel triazines of the present invention comprising pendant vinyl groups are used. Such red-shifted trisaryl-1,3,5-triazines may be grafted to saturated polymers, e.g., polyolefins and their copolymers such as polyethylene, polypropylene and poly(ethylene-vinyl acetate), or to polymers comprising unsaturated moieties, e.g., polybutadiene, polyisoprene, ethylene-propylene-(dienc monomer) terpolymers and polystyrene and its copolymers.

The red-shifted trisaryl-1,3,5-triazines of the present invention may be used in widely varying amounts in such applications depending upon such things as the material to be stabilized and the particular application. However, when employed as a stabilizing additive for materials such as organic polymers, the red-shifted trisaryl-1,3,5-triazines of the present invention are typically employed in amounts from about 0.01 to about 20% by weight, preferably from about 0.1 to about 10% by weight, and most preferably from about 0.1 to about 5% by weight, based on the weight of the material to be stabilized. In screening applications such as sunscreening compositions, the triazines are utilized in the same relative amounts but based on the total weight of the screening agent.

The novel stabilizers of the present invention may also be employed in a non-bondable capacity, for example, in the stabilization of thermoplastic polymers as set forth in the many of the previously incorporated references. Examples of preferred thermoplastic polymers are polyolefins and polymers comprising heteroatoms in the main chain. Preferred polymers are also thermoplastic polymers comprising nitrogen, oxygen and/or sulphur, especially nitrogen or oxygen, in the main chain. Also of interest are compositions in which the polymer is a polyolefin, for example polyethylene or polypropylene.

Incorporation into the thermoplastic polymers can be carried out by addition of the novel red-shifted trisaryl-1,3,5-triazine compound and any further additives by the methods conventional in the art. The incorporation can expediently be made before or during shaping, for example by mixing the pulverulent components or by adding the stabilizer to the melt or solution of the polymer, or by applying the dissolved or dispersed compounds to the polymer, with or without subsequent evaporation of the solvent. Elastomers can also be stabilized as lattices.

The novel mixtures can also be added to the polymers to be stabilized in the form of a masterbatch which comprises these compounds, for example, in a concentration of from about 2.5 to about 25%, preferably from about 5 to about 20% by weight of the polymer.

The novel mixtures can expediently be incorporated into the polymeric material by any number of methods, including those conventionally employed in the art, including by, for example: a) as an emulsion or dispersion (for example to lattices or emulsion polymers); (b) as a dry mix during mixing of additional components or polymer mixtures; (c) by direct addition to the processing equipment (for example extruders, internal mixers, etc.); or (d) as a solution or melt.

The stabilized polymer compositions obtained in this way can be converted into shaped articles, for example fibers, films, tapes, sheets, sandwich boards, containers, pipes and other profiles, by any number of conventional methods, for example hot pressing, spinning, extrusion, roto-molding or injection molding. Therefore, the present invention additionally relates to the use of the polymer composition according to the invention for the production of a shaped article.

Depending upon their ultimate end use, the red-shifted trisaryl-1,3,5-triazines of the present invention may be combined with a variety of additives conventionally employed in the UV stabilizing art. Examples of such additives include but are not limited to:

a. Antioxidants (i) Alkylated monophenols such as 2,6-di-tert-butyl-4-methylphenol; 2-tert-butyl-4,6-dimethylphenol; 2,6-di-tert-butyl-4-ethylphenol; 2,6-di-tert-butyl-4-n-butylphenol; 2,6-di-tert-butyl-4-isobutylphenol; 2,6-dicyclopentyl-4-methylphenol; 2-(α-methylcyclohexyl)-4,6-dimethylphenol; 2,6-dioctadecyl-4-methylphenol; 2,4,6-tricyclohexylphenol; 2,6-di-tert-butyl-4-methoxymethylphenol; nonylphenols which are liner or branched in the side chains such as 2,6-di-nonyl-4-methylphenol; 2,4-dimethyl-6-(1-methylundec-1-yl) phenol; 2,4-dimethyl-6-(1-methylheptadec-1-yl)phenol; 2,4-dimethyl-6-(I-methyltridec-1-yl)phenol; and mixtures thereof.

(ii) Alkylthiomethylphenols such as 2,4-dioctylthiomethyl-6-tert-butylphenol; 2,4-dioctylthiomethyl-6-methylphenol; 2,4-dioctylthiomethyl-6-ethylphenol; and 2,6-di-dodecylthiomethyl-4-nonylphenol.

(iii) Hydroquinones and alkylated hydroquinones such as 2,6-di-tert-butyl-4-methoxyphenol; 2,5-di-tert-butylhydroquinone; 2,5-di-tert-amylhydroquinone; 2,6-diphenyl-4-octadecyloxyphenol; 2,6-di-tert-butylhydroquinone; 2,5-di-tert-butyl-4-hydroxyanisole; 3,5-di-tert-butyl-4-hydroxyanisole; 3,5-di-tert-butyl-4-hydroxyphenyl stearate; and bis(3,5-di-tert-butyl-4-hydroxyphenyl)adipate.

(iv) Tocopherols such as α-tocopherol, β-tocopherol, γ-tocopherol, δ-tocopherol, and mixtures thereof (vitamin E).

(v) Hydroxylated thiodiphenyl ethers such as 2,2'-thiobis(6-tert-butyl-4-methylphenol); 2,2'-thiobis(4-octylphenol); 4,4'-thiobis(6-tert-butyl-3-methylphenol); 4,4'-thiobis(6-tert-butyl-2-methylphenol); 4,4'-thiobis(3,6-di-secamylphenol); and 4,4'-bis(2,6-dimethyl-4-hydroxyphenyl)disulfide.

(vi) Alkylidenebisphenols such as 2,2'-methylenebis(6-tert-butyl-4-methylphenol); 2,2'-methylenebis(6-tert-butyl-4- ethylphenol); 2,2'-methylenebis[4-methyl-6-(α-methylcyclohexyl)phenol]; 2,2'-methylenebis(4-methyl-6-cyclohexylphenol); 2,2'-methylenebis(6-nonyl-4-methylphenol); 2,2'-methylenebis(4,6-di-tert-butylphenol); 2,2'-ethylidenebis(4,6-di-tert-butylphenol); 2,2'-ethylidenebis(6-tert-butyl-4-isobutylphenol); 2,2'-methylenebis[6-(α-methylbenzyl)-4-nonylphenol]; 2,2'-methylenebis[6-(α,α-dimethylbenzyl)- 4-nonylphenol]; 4,4'-methylenebis(2,6-di-tert-butylphenol); 4,4'-methylenebis(6-tert-butyl-2-methylphenol); 1,1-bis(5-tert-butyl-4-hydroxy-2-methylphenyl)butane; 2,6-bis(3-tert-butyl-5-methyl-2-hydroxylbenzyl)-4-methylphenol; 1,1,3-tris(5-tert-butyl-4-hydroxy-2-methylphenyl)butane; 1,1-bis(5-tert-butyl-4-hydroxy-2-methylphenyl)-3-n-dodecylmercaptobutane; ethylene glycol bis[3,3-bis(3'-tert-butyl-4'-hydroxyphenyl)butyrate], bis(3 -tert-butyl-4-hydroxy-5-methylphenyl)dicyclopentadiene; bis[2-(3'-tert-butyl-2'-hydroxy-5'-methylbenzyl)-6-tert-butyl-4-methylphenyl]terephthalate; 1,1-bis(3,5-dimethyl-2-hydroxyphenyl)butane; 2,2-bis(3,5-di-tert-butyl-4-hydroxyphenyl)propane; 2,2-bis(5-tert-butyl-4-hydroxy-2-methylphenyl)-4-n-dodecylmercaptobutane; and 1,1,5,5-tetra(5-tert-butyl-4-hydroxy-2-methylphenyl)pentane.

(vii) O—, N— and S-benzyl compounds such as 3,5,3',5'-tetra-tert-butyl-4,4'-dihydroxydibenzyl ether; octadecyl-4-hydroxy-3,5-dimethylbenzylmercaptoacetate; tridecyl-4-hydroxy-3,5-di-tert-butylbenzylmercaptoacetate; tris(3,5-di-tert-butyl-4-hydroxybenzyl)amine; bis(4-tert-butyl-3-hydroxy-2,6-dimethylbenzyl)dithioterephthalate; bis(3 5-di-tert-butyl-4-hydroxybenzyl)sulfide; and isooctyl-3,5-di-tert-butyl-4-hydroxybenzylmercaptoacetate.

(viii) Hydroxybenzylate malonates such as dioctadecyl-2,2-bis(3,5-di-tert-butyl-2-hydroxybenzyl)malonate; dioctadecyl-2-(3-tert-butyl-4-hydroxy-5-methylbenzyl)malonate; didodecylmercaptoethyl-2,2-bis(3,5-di-tert-butyl-4-hydroxybenzyl)malonate; and bis[4-(1,1,3,3-tetramethylbutyl)phenyl]-2,2-bis(3,5-di-tert-butyl-4-hydroxybenzyl)malonate.

(ix) Aromatic hydroxybenzyl compounds such as 1,3,5-tris(3,5-di-tert-butyl-4-hydroxybenzyl)-2,4,6-trimethylbenzene; 1,4-bis(3,5-di-tert-butyl-4-hydroxybenzyl)-2,3,5,6-tetramethylbenzene; and 2,4,6-tris(3,5-di-tert-butyl-4-hydroxybenzyl)phenol.

(x) Triazine compounds such as 2,4-bis(octylmercapto-6-(3,5-di-tert-butyl-4-hydroxyanilino)-1,3,5-triazine; 2-octylmercapto-4,6-bis(3,5-di-tert-butyl-4-hydroxyanilino)-1,3,5-triazine; 2-octylmercapto-4,6-bis(3,5-di-tert-butyl-4-hydroxyphenoxy)-1,3,5-triazine; 2,4,6-tris(3,5-di-tert-butyl-4-hydroxyphenoxy)-1,3,5-triazine; 1,3,5-tris(3,5-di-tert-butyl-4-hydroxybenzyl)isocyanurate; 1,3,5-tris(4-tert-butyl-3-hydroxy-2,6-dimethylbenzyl)isocyanurate; 2,4,6-tris(3,5-di-tert-butyl-4-hydroxyphenylethyl)-1,3,5-triazine; 1,3,5-tris(3,5-di-tert-butyl-4-hydroxyphenylpropionyl)-hexahydro-1,3,5-triazine; and 1,3,5-tris(3 ,5-dicyclohexyl-4-hydroxybenzyl)isocyanurate.

(xi) Benzylphosphonates such as dimethyl-2,5-di-tert-butyl-4-hydroxybenzylphosphonate; diethyl-3,5-di-tert-butyl-4-hydroxybenzylphosphonate; dioctadecyl-3,5-di-tert-butyl-4-hydroxybenzylphosphonate; dioctadecyl-5-tert-butyl-4-hydroxy-3-methylbenzylphosphonate; and the calcium salt of the monoethyl ester of 3,5-di-tert-butyl-4-hydroxybenzylphosphonic acid.

(xii) Acylaminophenols such as 4-hydroxylauranilide; 4-hydroxystearanilide; and octyl N-(3,5-di-tert-butyl-4-hydroxyphenyl)carbamate.

(xiii) Esters of P-(3,5-di-tert-butyl-4-hydroxyphenyl) propionic acid with mono- or polyhydric alcohols such as methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane and 4-hydroxymethyl-1-phospha-2,6,7-trioxabicyclo[2.2.2] octane.

(xiv) Esters of β-(5-tert-butyl-4-hydroxy-3-methylphenyl) propionic acid with mono- or polyhydric alcohols such as methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane and 4-hydroxymethyl-1-phospha-2,6,7-trioxabicyclo[2.2.2] octane.

(xv) Esters of β-(3,5-dicyclohexyl-4-hydroxyphenyl) propionic acid with mono- or polyhydric alcohols such as methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)-oxamide, 3-thiaundecanol, 3-thiapentadecanol, trimethylhexanediol, trimethylolpropane and 4-hydroxymethyl-1-phospha-2,6,7-trioxabicyclo[2.2.2] octane.

(xvi) Esters of 3,5-di-tert-butyl-4-hydroxyphenyl acetic acid with mono- or polyhydric alcohols such as methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

(xvii) Amides of β-(3,5-di-tert-butyl-4-hydroxyphenyl) propionic acid such as N,N'-bis(3,5-di-tert-butyl-4-hydroxyphenylpropionyl)hexamethylenediamine; N,N'-bis(3,5-di-tert-butyl-4-hydroxyphenylpropionyl) trimethylenediamine; and N,N'-bis(3,5-di-tert-butyl-4-hydroxyphenylpropionyl)hydrazine.

(xviii) Ascorbic acid (Vitamin C).

(xix) Aminic antioxidants such as N,N'-diisopropyl-p-phenylenediamine; N,N'-di-sec-butyl-p-phenylenediamine; N,N'-bis(1,4-dimethylpentyl)-p-phenylenediamine; N,N'-bis(1 -ethyl-3-methylpentyl)-p-phenylenediamine; N,N'-bis(1-methylheptyl)-p-phenylenediamine; N,N'-dicyclohexyl-p-phenylenediamine; N,N'-diphenyl-p-phenylenediamine; N,N'-bis(2-naphthyl)-p-phenylenediamine; N-isopropyl-N'-phenyl-p-phenylenediamine; N-(1,3-dimethylbutyl)-N'-phenyl-p-phenylenediamine; N-(1-methylheptyl)-N'-phenyl-p-phenylenediamine; N-cyclohexyl-N'-phenyl-p-phenylenediamine; 4-(p-toluenesulfonamoyl) diphenylamine; N,N'-dimethyl-N,N'-di-sec-butyl-p-phenylenediamine; diphenylamine; allyldiphenylamine; 4-isopropoxydiphenylamine; -phenyl-1-naphthylamine; N-(4-tert-octylphenyl)-1-naphthylamine; N-phenyl-2-naphthylamine; octylated diphenylamine such as p,p'-di-tert-octyldiphenylamine; 4-n-butylaminophenol;

4-butyrylaminophenol; 4-nonanoylaminophenol; 4-dodecanoylaminophenol; 4-octadecanoylaminophenol; bis(4-methoxyphenyl)amine; 2,6-di-tert-butyl-4-dimethylaminomethylphenol; 2,4'-diaminophenylmethane; 4,4'-diaminodiphenylmethane; N,N,N',N'-tetramethyl-4,4'-diaminodiphenylmethane; 1,2-bis[(2-methylphenyl)amino]ethane; 1,2-bis(phenylamino)propane; (o-tolyl)biguanide; bis[4-(1',3'-dimethylbutyl)phenyl]amine; tert-octylated N-phenyl-1-naphthylamine; a mixture of mono- and dialkylated tert-butyl/tert-octyldiphenylamines, a mixture of mono- and dialkylated nonyldiphenylamines; a mixture of mono- and dialkylated dodecyldiphenylamines; a mixture of mono- and dialkylated isopropyl/isohexyldiphenylamines, a mixture of mono- and dialkylated tert-butyldiphenylamines; 2,3-dihydro-3,3-dimethyl-4HE-1, 4-benzothiazine; phenothiazine; a mixture of mono- and dialkylated tert-butyl/tert-octyl phenothiazines; a mixture of mono- and dialkylated tert-octylphenothiazines; N-allylphenothiazine; N,N,N',N'-tetraphenyl-1,4-diaminobut-2-ene; N,N-bis(2,2,6,6-tetramethylpiperid-4-yl)hexamethylenediamine; bis(2,2,6,6-tetramethylpiperid-4-yl)sebacate; 2,2,6,6-tetramethylpiperidin-4-one; and 2,2,6,6-tetramethylpiperidin-4-ol.

b. UV-absorbers and Light Stabilizers (i) 2-(2'-Hydroxyphenyl)benzotriazoles such as 2-(2'-hydroxy-5'-methylphenyl)-benzotriazole; 2-(3',5'-di-tert-butyl-2'-hydroxyphenyl)benzotriazole; 2-(5'-tert-butyl-2'-hydroxyphenyl)benzotriazole; 2-(2'-hydroxy-5'-(1,1,3,3-tetramethylbutyl)phenyl)benzotriazole; 2-(3', 5'-di-tert-butyl-2'-hydroxyphenyl)-5-chlorobenzotriazole; 2-(3'-tert-butyl-2'-hydroxy-5'-methylphenyl)-5-chloro-benzotriazole; 2-(3 '-sec-butyl-5'-tert-butyl-2'-hydroxyphenyl)-benzotriazole; 2-(2'-hydroxy-4'-octoxyphenyl)benzotriazole; 2-(3',5'-di-tert-amyl-2'-hydroxphenyl)benzotriazole; 2-(3',5'-bis($\alpha,\alpha$-dimethylbenzyl)-2'-hydroxyphenyl)-benzotriazole; a mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole and 2-(3'-tert-butyl-2'-hydroxy-5'-(2-isooctyloxycarbonylethyl)phenylbenzotriazole; 2,2-methylenebis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl]benzotriazole with polyethylene glycol 300; and [R—CH$_2$CH—COO(CH$_2$)$_3$]$_2$ B where R=3'-tert-butyl-4'-hydroxy-5'-2H-benzotriazol-2-ylphenyl.

(ii) 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimcthoxy derivative.

(iii) Esters of substituted and unsubstituted benzoic acids such as 4-tert-butyl-phenyl salicylate; phenyl salicylate; octylphenyl salicylate; dibenzoyl resorcinol; bis(4-tert-butylbenzoyl) resorcinol; benzoyl resorcinol; 2,4-di-tert-butylphenyl 3,5-di-tert-butyl-4-hydroxybenzoate; hexadecyl 3,5-di-tert-butyl-4-hydroxybenzoate; octadecyl 3,5-di-tert-butyl-4-hydroxybenzoate; and 2-methyl-4,6-di-tert-butylphenyl 3,5-di-tert-butyl-4-hydroxybenzoate.

(iv) Acrylates such as ethyl $\alpha$-cyano-$\beta,\beta$-diphenylacrylate; isooctyl $\alpha$-cyano-$\beta,\beta$-diphenylacrylate; methyl $\alpha$-carbomethoxycinnamate; methyl $\alpha$-cyano-$\beta$-methyl-p-methoxycinnamate; butyl $\alpha$-cyano-$\beta$-methyl-p-methoxycinnamate; methyl $\alpha$-carbomethoxy-p-methoxycinnamate; and N-($\beta$-carbomethoxy-$\beta$-cyanovinyl)-2-methylindoline.

(v) Nickel compounds such as nickel complexes of 2,2'-thio-bis-[4-(1,1,3,3-tetramethylbutyl)phenol], including the 1:1 or 1:2 complex, with or without additional ligands such as n-butylamine, triethanolamine or N-cyclohexyldiethanolamine; nickel dibutyldithiocarbamate; nickel salts of monoalkyl esters including the methyl or ethyl ester of 4-hydroxy-3,5-di-tert-butylbenzylphosphonic acid; nickel complexes of ketoximes including 2-hydroxy-4-methylphenyl undecyl ketoxime; and nickel complexes of 1-phenyl-4-lauroyl-5-hydroxypyrazole, with or without additional ligands.

(vi) Sterically hindered amines as well as the N derivatives thereof (e.g., N-alkyl, N-hydroxy, N-alkoxy and N-acyl), such as bis(2,2,6,6-tetramethylpiperidin-4-yl) sebacate; bis(2,2,6,6-tetramethylpiperidin-4-yl)succinate; bis(1,2,2, 6,6-pentamethylpiperidin-4-yl)sebacate; bis(1-octyloxy-2,2,6,6-tetramethylpiperidin-4-yl)sebacate; bis(1,2,2,6,6-pentamethylpiperidin-4-yl) n-butyl 3,5-di-tert-butyl-4-hydroxybenzylmalonate; the condensate of 1-(2-hydroxyethyl)-2,2,6,6-tetramethyl-4-hydroxypiperidine and succinic acid; the condensate of N,N'-bis(2,2,6,6-tetramethylpiperidin-4-yl)hexamethylenediamine and 4-tert-octylamino-2,6-dichloro-1,3,5-triazine; tris(2,2,6, 6-tetramcthylpiperidin-4-yl) nitrilotriacetate; tetrakis(2,2, 6,6-tetramethylpiperidin-4-yl)- 1,2,3,4-butanetetracarboxylate; 1,1'-(1,2-ethanediyl)bis(3,3,5,5-tetramethylpiperazinone); 4-benzoyl-2,2,6,6-tetramethylpiperidine; 4-stearyloxy-2,2,6,6-tetramethylpiperidine; bis(1,2,2,6,6-pentamethylpiperidyl)-2-n-butyl-2-(2-hydroxy-3,5-di-tert-butylbenzyl)malonate; 3-n-octyl-7,7,9,9-tetramethyl-1,3,8-triazaspiro[4.5]decan-2,4-dione; bis(1-octyloxy-2, 2,6,6-tetramethylpiperidyl)sebacate; bis(1-octyloxy-2,2, 6,6-tetramethylpiperidyl)succinate; the condensate of N,N'-bis(2,2,6,6-tetramethyl piperidin-4-yl) hexamethylenediamine and 4-morpholino-2,6-dichloro-1, 3,5-triazine; the condensate of 2-chloro-4,6-bis(4-n-butylamino-2,2,6,6-tetramethylpiperidyl)-1,3,5-triazine and 1,2-bis(3-aminopropylamino)ethane; the condensate of 2-chloro-4,6-bis(4-n-butylamino-1,2,2,6,6-pentamethylpiperidyl)-1,3,5-triazine and 1,2-bis-(3-aminopropylamino)ethane; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl) pyrrolidin-2,5-dione; 3-dodecyl-1-(1-ethanoyl-2,2,6,6-tetramethylpiperidin-4-yl)pyrrolidin-2,5-dione; 3-dodecyl-1-(1,2,2,6,6-pentamethylpiperidin-4-yl) pyrrolidine-2,5-dione; a mixture of 4-hexadecyloxy- and 4-stearyloxy-2,2,6,6-tetramethylpiperidine; the condensate of N,N'-bis(2,2,6,6-tetramethylpiperidin-4-yl) hexamethylenediamine and 4-cyclohexylamino- 2,6-dichloro-1,3,5-triazine; the condensate of 1,2-bis(3-aminopropylamino)ethane, 2,4,6-trichloro-1,3,5-triazine and 4-butylamino-2,2.6,6-tetramethylpiperidine (CAS Reg. No. [136504-96-6]); 2-undecyl-7,7,9,9-tetramethyl-1-oxa-3,8-diaza-4-oxospiro[4.5]decane; oxo-piperanzinyl-triazines or so-called PIP-T HALS, e.g., GOODRITE® 3034, 3150 and 3159 and similar materials disclosed in U.S. Pat. No. 5,071,981; photobondable HALS such as SANDUVOR® PR-31 and PR-32 (Clariant Corp.) and similar materials disclosed in GB-A-2269819; and the reaction product of 7,7,9,9-tetramethyl-2-cycloundecyl-1-oxa-3,8-diaza-4-oxospiro[4.5]decane and epichlorohydrin. See also generally U.S. Pat. No. 4,619,956, U.S. Pat. No. 5,106,891, GB-A-2269819, EP-A-0309400, EP-A-0309401, EP-A-0309402 and EP-A-0434608.

(vii) Oxamides such as 4,4'-dioctyloxyoxanilide; 2,2'-diethoxyoxanilide; 2,2'-dioctyloxy-5,5'-di-tert-butoxanilide; 2,2'-didodecyloxy-5,5'-di-tert-butyloxanilide; 2-ethoxy-2'-ethyloxanilide; N,N'-bis(3-dimethylaminopropyl)oxamide; 2-ethoxy-5-tert-butyl-2'-ethyloxanilide and its mixture with 2-ethoxy-2'-ethyl-5,4'-di-tert-butoxanilide; and mixtures of o- and p-methoxy disubstituted oxanilides and mixtures of o- and p-ethoxy disubstituted oxanilides.

(viii) 2-(2-Hydroxyphenyl)-1,3,5-triazines disclosed in the previously incorporated references, such as 2,4,6-tris(2-hydroxy-4-octyloxyphenyl)-1,3,5-triazine; 2-(2-hydroxy-4-n-octyloxyphenyl)-4,6-bis(2,4-dimethylphenyl)-1,3,5-triazine; 2-(2-hydroxy-4-(mixed iso-octyloxyphenyl)-4,6-bis(2,4-dimethylphenyl)-1,3,5-triazine; 2-(2,4-dihydroxyphenyl)-4,6-bis(2,4-dimethylphenyl)-1,3,5-triazine; 2,4-bis(2-hydroxy-4-propyloxyphenyl)-6-(2,4-dimethylphenyl)-1,3,5-triazine; 2-(2-hydroxy-4-octyloxyphenyl)-4,6-bis(4-methylphenyl)-1,3,5-triazine; 2-(2-hydroxy-4-dodecyloxyphenyl)-4,6-bis(2,4-dimethylphenyl)-1,3,5-triazine; 2-(2-hydroxy-4-tridecyloxyphenyl)-4,6-bis(2,4-dimethylphenyl)-1,3,5-triazine; 2-[2-hydroxy-4-(2-hydroxy-3-butyloxypropyloxy)phenyl]-4,6-bis(2,4-dimethylphenyl)-1,3,5-triazine; 2-[2-hydroxy-4-(2-hydroxy-3-octyloxypropyloxy)-phenyl]-4,6-bis(2,4-dimethylphenyl)-1,3,5-triazine; 2-[4-dodecyloxy/tridecyloxy-2-hydroxypropoxy)-2-hydroxyphenyl]-4,6-bis(2,4-dimethylphenyl)-1,3,5-triazine; 2-[2-hydroxy-4-(2-hydroxy-3-dodecyloxypropoxy)phenyl]-4,6-bis(2,4-dimethylphenyl)-1,3,5-triazine; 2-(2-hydroxy-4-hexyloxy)phenyl-4,6-diphenyl-1,3,5-triazine; 2-(2-hydroxy-4-methoxyphenyl)-4,6-diphenyl-1,3,5-triazine; 2,4,6-tris[2-hydroxy-4-(3-butoxy-2-hydroxypropoxy)phenyl]-1,3,5-triazine; and 2-(2-hydroxyphenyl)-4-(4-methoxyphenyl)-6-phenyl-1,3,5-triazine.

(c) Metal deactivators such as N,N'-diphenyloxamide; N-salicylal-N'-salicyloyl hydrazine; N,N'-bis(salicyloyl) hydrazine; N,N'-bis(3,5-di-tert-butyl-4-hydroxyphenylpropionyl)hydrazine; 3-salicyloylamino-1,2,4-triazole; bis(benzylidene)oxalyl dihydrazide; oxanilide; isophthaloyl dihydrazide; sebacoyl bisphenylhydrazide; N,N'-diacetyladipoyl dihydrazide; N,N'-bis(salicyloyl) oxalyl dihydrazide; and N,N'-bis(salicyloyl)thiopropionyl dihydrazide.

(d) Phosphites and phosphonites, such as triphenyl phosphite; diphenyl alkyl phosphites; phenyl dialkyl phosphites; tris(nonylphenyl) phosphite; trilauryl phosphite; trioctadecyl phosphite; distearyl pentaerythritol diphosphite; tris(2,4-di-tert-butylphenyl)phosphite; diisodecyl pentaerythritol diphosphite; bis(2,4,-di-tert-butylphenyl)pentaerythritol diphosphite; bis(2,6-di-tert-butyl-4-methylphenyl) pentaerythritol diphosphite; bis(isodecyloxy)pentaerythritol diphosphite; bis(2,4-di-tert-butyl-6-methylphenyl) pentaerythritol diphosphite; bis(2,4,6-tris(tert-butyl)phenyl) pentaerythritol diphosphite; tristearyl sorbitol triphosphite; tetrakis(2,4-di-tert-butylphenyl)-4,4'-biphenylene diphosphonite; 6-isooctyloxy-2,4,8,10-tetra-tert-butyl-12H-dibenzo[d,g]-1,3,2-dioxaphosphocin; 6-fluoro-2,4,8,10-tetra-tert-butyl-12-methyl-dibenzo[d,g]-1,3,2-dioxaphosphocin; bis(2,4-di-tert-butyl-6-methylphenyl) methylphosphite; and bis(2,4-di-tert-butyl-6-methylphenyl) ethylphosphite.

(e) Hydroxylamines such as N,N-dibenzylhydroxylamine; N,N-diethylhydroxylamine; N,N-dioctylhydroxylamine; N,N-dilaurylhydroxylamine; N,N-ditetradecylhydroxylamine; N,N-dihexadecylhydroxylamine; N,N-dioctadecylhydroxylamine; N-hexadecyl-N-octadecylhydroxylamine; N-heptadecyl-N-octadecylhydroxylamine; and N,N-dialkylhydroxylamine derived from hydrogenated tallow fatty amines.

(f) Nitrones such as N-benzyl-alpha-phenyl nitrone; N-ethyl-alpha-methyl nitrone; N-octyl-alpha-heptyl nitrone; N-lauryl-alpha-undecyl nitrone; N-tetradecyl-alpha-tridecyl nitrone; N-hexadecyl-alpha-pentadecyl nitrone; N-octadecyl-alpha-heptadecyl nitrone; N-hexadecyl-alpha-heptadecyl nitrone; N-octadecyl-alpha-pentadecyl nitrone; N-heptadecyl-alpha-heptadecyl nitrone; N-octadecyl-alpha-hexadecyl nitrone; and nitrones derived from N,N-dialkylhydroxylamines prepared from hydrogenated tallow fatty amines.

(g) Thiosynergists such as dilauryl thiodipropionate and distearyl thiodipropionate.

(h) Peroxide scavengers such as esters of P-thiodipropionic acid, for example the lauryl, stearyl, myristyl or tridecyl esters; mercaptobenzimidazole or the zinc salt of 2-mercaptobenzimidazole; zinc dibutyldithiocarbamate; dioctadecyl disulfide; and pentaerythritol tetrakis(β-dodecylmercapto)propionate.

(i) Polyamide stabilizers such as copper salts in combination with iodides and/or phosphorus compounds and salts of divalent manganese.

(j) Basic co-stabilizers such as melamine; polyvinylpyrrolidone; dicyandiamide; triallyl cyanurate; urea derivatives; hydrazine derivatives; amines; polyamides; polyurethanes; alkali metal salts and alkaline earth metal salts of higher fatty acids, for example calcium stearate, zinc stearate, magnesium behenate, magnesium stearate, sodium ricinoleate and potassium palmitate; antimony pyrocatecholate; and tin pyrocatecholate.

(k) Nucleating agents including inorganic substances such as talc and metal oxides (e.g. titanium oxide or magnesium oxide) and phosphates, carbonates and sulfates of, preferably, alkaline earth metals; organic compounds such as mono- or polycarboxylic acids and salts thereof, for example 4-tert-butylbenzoic acid, adipic acid, diphenylacetic acid, sodium succinate and sodium benzoate; and polymeric compounds such as ionic copolymers (e.g., ionomers).

(l) Fillers and reinforcing agents such as calcium carbonate; silicates; glass fibers; asbestos; talc; kaolin; mica; barium sulfate; metal oxides and hydroxides; carbon black; graphite; wood flour and flours or fibers from other natural products; and synthetic fibers.

(m) Other additives such as plasticizers, lubricants, emulsifiers, pigments, rheological additives, catalysts, levelling assistants, optical brighteners, flameproofing agents, antistatic agents and blowing agents.

(n) Benzofuranones and indolinones such as those disclosed in U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4316611, DE-A-4316622, DE-A-43 16876, EP-A-0589839 and EP-A-0591102; 3-[4-(2-acetoxyethoxy)phenyl]-5,7-di-tert-butyl-benzofuran-2-one; 5,7-di-tert-butyl-3-[4-(2-stearoyloxyethoxy)-phenyl]benzofuran-2- one; 3,3'-bis[5,7-di-tert-butyl-3-(4-[2-hydroxyethoxy] phenyl)benzofuran-2-one]; 5,7-di-tert-butyl-3-(4-ethoxyphenyl)benzofuran-2-one; 3-(4-acetoxy-3,5-dimethylphenyl)-5,7-di-tert-butyl-benzofuran-2-one; 3-(3,5-dimethyl-4-pivaloyloxyphenyl)-5,7-di-tert-butyl-benzofuran-2-one; and 5,7-di-tert-butyl-3-(3,4-dimethylphenyl)-3H-benzofuran-2-one.

The novel red-shifted trisaryl-1,3,5-triazines of the present invention can also be employed in multilayer systems. In such systems, a polymer composition having from about 0.1 to about 20% by weight and preferably a relatively high content of novel stabilizer, for example, about 5–15% by weight, is applied in a thin film (e.g., about 5–500 μm thick and, preferably, about 10–100 μm thick) to a shaped article made from a polymer containing little or no ultraviolet stabilizers. Such composition may be applied at the same time as the shaping of the base structure, for example by coextrusion in a manner analogous to that described in U.S. Pat. No. 4,948,666 (incorporated by reference herein for all purposes as if fully set forth). Alternatively, application can also be made to the ready-formed base structure, for example by lamination with a film or by coating with a solution. The outer layer or layers of the finished article have the function of a UV filter, which protects the interior of the article from UV light. The outer layer preferably contains about 0.1 to about 20%, preferably about 1 to about 15%, and most preferably about 2 to about 10% by weight of the outer layer composition, of at least one of the red-shifted trisaryl-1,3,5-triazine compounds of the present invention.

The polymers stabilized in this way are notable for high weathering resistance, especially for high resistance to UV light. This enables them to retain their mechanical properties, and their color surface properties such as gloss and distinctness of image, for a long time even when used outside. Moreover, due to the bondable nature of the presently claimed triazine compounds, migration of these UV absorbers between the layers of the multi-layer coatings can, under the appropriate circumstances, be minimized.

In another embodiment of the present invention, the novel mixtures comprising compounds of the formulas (I)–(III) can be used as stabilizers for coatings, for example for paints such as disclosed in numerous references (see, e.g., U.S. Pat. No. 4,619,956, U.S. Pat. No. 4,740,542, U.S. Pat. No. 4,826,978, U.S. Pat. No. 4,962,142, U.S. Pat. No. 5,106,891, U.S. Pat. No. 5,198,498, U.S. Pat. No. 5,298,067, U.S. Pat. No. 5,322,868, U.S. Pat. No. 5,354,794, U.S. Pat. No. 5,369,140, U.S. Pat. No. 5,420,204, U.S. Pat. No. 5,461,151, U.S. Pat. No. 5,476,937, EP-0434608 and EP-A-0444323). Of particular interest are coatings and paints for the automobile industry. The invention therefore also relates to those compositions or mixtures comprising the instant inventive compound which are film-forming binders for coatings. Film forming binders are discussed at length infra.

These novel film-forming binders may be used, for example, in coating compositions. In these coating compositions, the amount of the presently claimed red-shifted trisaryl-1,3,5-triazines may be about 0.01 to about 20%, preferably about 0.02 to about 5% by of the film-forming binder by weight.

Multilayer coating systems are possible here as well (such as electrocoat/basecoat/clearcoat systems), where the concentration of the novel stabilizer in one or more of the layers, and typically the outer layer such as the clearcoat, can be relatively high, for example from about 0.01 to about 20%, preferably about 0.01 to about 10%, and more preferably about 0.02 to about 5% by weight of binder.

The use of the novel stabilizer in coatings is accompanied by the additional advantage that it prevents delamination, i.e. the flaking-off of the coating from the substrate. This advantage is particularly important in the case of metallic substrates, including multilayer systems on metallic substrates, and particularly epoxy e-coated metallic substrates.

The binder can in principle be any binder which is customary in industry, for example those described in Ullmann's Encyclopedia of Industrial Chemistry, 5th Edition, Vol. A18, pp. 368–426, VCH, Weinheim 1991 which is incorporated herein by reference. In general, it is a film-forming binder based on a thermoplastic or curable resin, predominantly on a curable resin. Examples of thermoplastic binders include acrylics, polyesters, polyurethanes and PVC plastisols. Examples of curable binders include functional alkyd, acrylic, polyester, phenolic, melamine, epoxy and polyurethane resins and mixtures thereof.

Such curable binders can be an ambient curable or a thermosetting binder. Further, in some systems it may be advantageous to add a curing catalyst to such systems. Suitable catalysts which accelerate curing of the binder are described, for example, in Ullmann's Encyclopedia of Industrial Chemistry, Vol. A18, p. 469, VCH Verlagsgesellschaft, Weinheim 1991. Preferred binders include those which comprise a functional acrylate resin and a crosslinking agent.

A wide variety of binders may be employed in such coating systems. Examples of suitable coating compositions containing specific binders include but are not limited to:

1. paints based on ambient curable or thermosetting alkyd, acrylate, polyester, epoxy or melamine resins or mixtures of such resins, if desired with addition of a curing catalyst;
2. two-component polyurethane paints based on hydroxyl-containing acrylate, polyester or polyether resins and aliphatic or aromatic isocyanates, isocyanurates or polyisocyanates;
3. one-component polyurethane paints based on blocked isocyanates, isocyanurates or polyisocyanates which are deblocked during baking;
4. two-component paints based on (poly)ketimines and aliphatic or aromatic isocyanates, isocyanurates or polyisocyanates;
5. two-component paints based on (poly)ketimines and an unsaturated acrylate resin or a polyacetoacetate resin or a methacrylamidoglycolate methyl ester;
6. two-component paints based on carboxyl- or amino-containing polyacrylates and polyepoxides;
7. two-component paints based on acrylate resins containing anhydride groups and on a polyhydroxy or polyamino component;
8. two-component paints based on (poly)oxazolines and acrylate resins containing anhydride groups, or unsaturated acrylate resins, or aliphatic or aromatic isocyanates, isocyanurates or polyisocyanates;
9. two-component paints based on unsaturated polyacrylates and polymalonates;
10. thermoplastic polyacrylate paints based on thermoplastic acrylate resins or externally crosslinking acrylate resins in combination with etherified melamine resins;

11. paint systems based on siloxane-modified or fluorine-modified acrylate resins.

In addition to the binder and novel red-shifted trisaryl-1,3,5-triazine of the present invention, the coating composition according to the invention preferably further comprise one or more additional ultraviolet light absorbers, including but not limited to those specifically listed above in section b. The additional UV absorbers may be, for example, another tris-aryl-1,3,5-triazine, a 2-hydroxyphenyl-2H-benzotriazole, a 2-hydroxybenzophenone, an ester of an unsubstituted benzoic acid, an acrylate, an oxamide (oxanilide), or any combination of the above. Preferably, the additional UV absorber is a 2-hydroxyphenyl-2H-benzotriazole and the weight ratio of benzotriazole to amido or carbamate triazine is 4:1 to 1:4. More preferably, the weight ratio of benzotriazole to amido or carbamate triazine is 2:1 to 1:2.

To achieve maximum light stability, it is of particular interest to add sterically hindered amines, examples of which are set out in the above-mentioned section b(vi). The invention therefore also relates to a coating composition which, in addition to the binder, the novel red-shifted trisaryl-1,3,5-triazine and, optionally, additional UV absorbers, comprises a light stabilizer of the sterically hindered amine type. The sterically hindered amine is employed in an amount of about 0.01 to 5% by weight based on the weight of the solid binder, preferably about 0.02 to 2% by weight.

One specific example of such a sterically hindered amine is a 2,2,6,6-tetramethyl piperazinone containing at least one group of the formula:

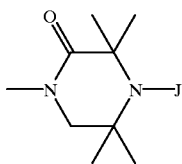

in which J is, for example, hydrogen, hydroxyl, alkyl (such as methyl), alkoxy (such as methoxy) or acyl.

More preferably the stabilizer is a 2,2,6,6-tetraalkylpiperidine derivative containing at least one group of the formula:

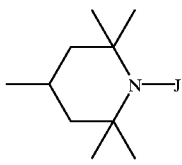

in which J is, for example, hydrogen, hydroxyl, alkyl (such as methyl), alkoxy (such as methoxy) or acyl.

Examples of tetraalkylpiperidine derivatives which can be used in combination with the present trisaryl-1,3,5-triazine compounds are given in U.S. Pat. Nos. 4,314,933, 4,344,876, 4,426,471, 4,426,472, 4,619,956, 5,004,770, 5,006,577, 5,064,883, 5,112,890, 5,124,378, 5,106,891, 5,204,473, and 5,461,151, which are incorporated by reference herein for all purposes as if fully set forth. It is particularly expedient to employ the following tetraalkylpiperidine derivatives, as well as their N-alkyl, N-acyl, N-hydroxyl and N-alkoxy analogs (where not already included in the following list):

bis(2,2,6,6-tetramethylpiperid-4-yl)succinate,
bis(2,2,6,6-tetramethylpiperid-4-yl)sebacate,
bis(1,2,2,6,6-pentamethylpiperid-4-yl)sebacate,
di(1,2,2,6,6-pentamethylpiperid-4-yl)butyl-(3,5-di-tert-butyl-4-hydroxybenzyl)malonate,
bis(1-octyloxy-2,2,6,6-tetramethylpiperid-4-yl)sebacate,
tetra(2,2,6,6-tetramethylpiperid-4-yl)butane-1,2,3,4-tetracarboxylate, tetra(1,2,2,6,6-pentamethylpiperid-4-yl)butane-1,2,3,4-tetracarboxylate, 2,2,4,4-tetramethyl-7-oxa-3,20-diaza-21-oxo-dispiro[5.1.11.2]heneicosane, and 8-acetyl-3-dodecyl-1,3,8-triaza-7,7,9,9-tetramethylspiro[4.5]decane-2,4-dione.

Commercially available examples of these and other tetraalkylpipieridine derivatives include SANDUVOR® 3050, 3052, 3055, 3056, 3058, PR-31 and PR-32 (Clariant Corp.); TINUVIN® 079L, 123, 144, 292, 440L and 622LD (Ciba Specialty Chemicals); CHIMASORB® 119 and 944 (Ciba Specialty Chemicals); and CYASORB® UV-3346, UV 3529, UV-3853, UV-500 and UV-516 (Cytec Industries Inc.).

Apart from the binder, the red-shifted trisaryl-1,3,5-triazine, and, if used, the additional ultraviolet light absorber or stabilizer, the coating composition can also comprise further components, examples being solvents, pigments, dyes, plasticizers, stabilizers, thixotropic agents, drying catalysts and/or leveling agents. Examples of possible components are those described in many of the previously incorporated references as well as Ullmann's Encyclopedia of Industrial Chemistry, 5th Edition, Vol. A18, pp. 429–471, VCH, Weinheim 1991; and Calbo, Leonard J., ed., Handbook of Coatings Additives, New York:Marcel Dekker (1987).

Possible drying catalysts or curing catalysts are, for example, organometallic compounds, amines, acids, amino-containing resins and/or phosphines.

Examples of acid catalysts are mineral acids, aliphatic and aromatic sulfonic acids (e.g. p-toluene sulfonic acid, dinonylnaphthalene disulfonic acid, dodecylbenzene sulfonic acid), oxalic acid, maleic acid, hexamic acid, phosphoric acid, alkyl phosphate esters, phthalic acid and acrylic acid copolymers.

Examples of organometallic compounds are metal carboxylates, especially those of the metals Pb, Mn, Co, Zn, Zr or Cu, or metal chelates, especially those of the metal Al, It or Zr, or organometallic compounds such as organotin compounds, for example. Examples of metal carboxylates are the stearates of Pb. Mn or Zn, the octoates of Co, Zn or Cu, the naphthenates of Mn and Co or the corresponding linoleates, resinates or tallates. Examples of metal chelates are the aluminum, titanium or zirconium chelates of acetylacetone, ethyl acetylacetate, salicylaldehyde, salicylaldoxime, o-hydroxyacetophenone or ethyl trifluoroacetylacetate and the alkoxides of these metals. Examples of organotin compounds are dibutyltin oxide, dibutyltin dilaurate or dibutyltin dioctoate.

Examples of amine drying or curing catalysts are, in particular, tertiary amines, for example tributylamine, triethanolamine, N-methyldiethanolamine, N-dimethylethanolamine, N-ethylmorpholine, N-methylmorpholine or diazabicyclooctane (triethylenediamine) and salts thereof. Further examples are quaternary ammonium salts, for example trimethylbenzylammonium chloride. Amino-containing resins are simultaneously binder and curing catalyst. Examples thereof are amino-containing acrylate copolymers.

The curing catalyst used can also be a phosphine, for example triphenylphosphine.

Another type of curing catalyst is a peroxide which can be used, for example, to cure a gel coating for a fiberglass article.

The novel coating compositions can also be radiation-curable coating compositions. In this case, the binder essentially comprises monomeric or oligomeric compounds containing ethylenically unsaturated bonds, which after application are cured by actinic radiation, i.e. converted into a crosslinked, high molecular weight form. Where the system is UV-curing, it generally contains a photoinitiator as well. Corresponding systems are described in the above-mentioned publication Ullmann's Encyclopedia of Industrial Chemistry, 5th Edition, Vol. A18, pages 451–453. In radiation-curable coating compositions, the novel stabilizers can also be employed without the addition of sterically hindered amines.

The novel coating compositions according to the invention can be applied to any desired substrates, for example to metal, wood, plastic, fiberglass or ceramic materials. The coating compositions can be pigmented mono-coats or multi-layer (primer/basecoat/clearcoat) systems typical of automotive finishes. In the latter case, the novel coating composition can be used for either the base coat, or clear coat, or for both layers. If the topcoat of an automotive finish comprises two layers, of which the lower layer is pigmented and the upper layer is not pigmented, the novel coating composition can be used for either the upper or the lower layer or for both layers, but preferably for the upper topcoat layer.

The novel coating compositions can be applied to the substrates by the customary methods, for example by brushing, spraying, pouring, dipping or electrophoresis; see also Ullmann's Encyclopedia of Industrial Chemistry, 5th Edition. Vol. A18, pp. 491–500.

Depending on the binder system, the coatings can be cured at room temperature or by heating. Thermosetting coatings are preferably cured at 50–150° C. and, in the case of powder coatings, even at higher temperatures.

The coatings obtained in accordance with the invention have excellent resistance to the damaging effects of light, oxygen and heat; particular mention should be made of the good light stability and weathering resistance of the coatings thus obtained, for example paints.

The invention therefore also relates to a coating, in particular a paint, which has been stabilized against the damaging effects of light, oxygen and heat by a content of the compound of the formulas (I)–(III), according to the invention. The paint can be a pigmented mono-coat which comprises a film-forming binder and an organic pigment or dye, an inorganic pigment, a metallic pigment, or a mixture thereof. The paint may also be a composition which comprises a primer in adhesion to a metal or plastic substrate; a pigmented basecoat that is in adhesion to the primer and which comprises a film-forming binder and an organic pigment or dye, an inorganic pigment, a metallic pigment, or a mixture thereof, and a clear coat that is in adhesion to the base coat and which comprises a film-forming binder and optionally a transparent pigment. One especially preferred use is a paint which is a clear topcoat for automobile original equipment manufacture (OEM) and/or refinish applications.

The invention furthermore relates to a process for stabilizing a coating based on polymers against damage by light, oxygen and/or heat, which comprises mixing with the coating composition a mixture comprising a compound of a red-shifted trisaryl-1,3,5-triazine and to the use of mixtures comprising a red-shifted trisaryl-1,3,5-triazine compound in coating compositions as stabilizers against damage by light, oxygen and/or heat.

The coating compositions can comprise an organic solvent or solvent mixture in which the binder is soluble. The coating composition can otherwise be an aqueous solution or dispersion. The vehicle can also be a mixture of organic solvent and water. The coating composition maybe a high-solids paint or can be solvent-free (e.g. a powder coating material).

The pigments can be inorganic, organic or metallic pigments. The novel coating compositions preferably contain no pigments and are used as a clearcoat.

Likewise preferred is the use of the coating composition as a topcoat for applications in the automobile industry, especially as a pigmented or unpigmented topcoat of the paint finish. Its use for underlying coats, however, is also possible.

The red-shifted trisaryl-1,3,5-triazines of this invention may be applied topically by polishing a surface with a composition comprising the red-shifted trisaryl-1,3,5-triazine and an inert carrier such as solvent, petroleum jelly, silicone oil in water emulsions, or automotive paint wax, e.g. Carnauba wax. These topical treatment compositions may be used to stabilize coating films, fabrics, leather, vinyl and other plastics and wood.

Preference is also given to the use of the novel red-shifted trisaryl-1,3,5-triazine compounds in photographic materials as stabilizer against damage by light, especially by UV light. The invention therefore also relates to a photographic material comprising an red-shifted trisaryl-1,3,5-triazine compound.

The compounds according to the invention can be used for photosensitive materials of all kinds. For example, they can be employed for color paper, color reversal paper, direct-positive color material, color negative film, color positive film, color reversal film and other materials. They are preferably used, inter alia, for photosensitive color material which comprises a reversal substrate or which forms positives.

Furthermore, the novel compounds can be combined with other UV absorbers, especially those which are dispersible in aqueous gelatin, for example with hydroxyphenylbenzotriazoles (cf. for example U.S. Pat. Nos. 4,853,471, 4,973, 702, 4,921,966 and 4,973,701), benzophenones, oxanilides, cyanoacrylates, salicylates, or acrylonitriles or thiazolines. In this context it is advantageous to employ these further, oil-dissolved UV absorbers in the photographic material in layers other than those comprising the novel UV absorbers.

The present invention also encompasses compositions containing one or more binders. In particular, the binder may comprise an alkyd, acrylic, polyester, phenolic, melamine, epoxy or polyurethane resin, or blends thereof. Examples of such binders include, but are not limited to:

(a) cold- or hot-crosslinkable alkyd, acrylate, polyester, epoxy or melamine resins or mixtures of such resins;

(b) a two-component polyurethane system comprising hydroxyl-containing acrylate, polyester or polyether resins and aliphatic or aromatic isocyanates, isocyanurates or polyisocyanates;

(c) a one-component polyurethane system comprising blocked isocyanates, isocyanurates or polyisocyanates which are deblocked during baking;

(d) a two-component system comprising (poly)ketimines and aliphatic or aromatic isocyanates, isocyanurates or polyisocyanates;

(e) a two-component system comprising (poly)ketimines and an unsaturated acrylate resin or a polyacetoacetate resin or a methacrylamidoglycolate methyl ester;

(f) a two-component system comprising carboxyl- or amino-containing polyacrylates and polyepoxides;

(g) a two-component system comprising acrylate resins containing anhydride groups and on a polyhydroxy or polyamino component;

(h) a two-component system comprising (poly)oxazolines and acrylate resins containing anhydride groups, or unsaturated acrylate resins, or aliphatic or aromatic isocyanates, isocyanurates or polyisocyanates;

(i) a two-component system comprising unsaturated polyacrylates and polymalonates;

(j) a thermoplastic polyacrylate system comprising thermoplastic acrylate resins or externally crosslinking acrylate resins in combination with etherified melamine resins; and (k) a system comprising siloxane-modified or fluorine-modified acrylate resins.

Such binder-containing compositions may further comprise a curing catalyst, or an organic solvent, and may be radiation-curable. In particular, such compositions may serve as coating compositions.

In particular, it is possible successfully to stabilize photographic materials similar to those described in U.S. Pat. No. 4,518,686.

The invention therefore additionally relates to a photographic material comprising, on support, a blue-sensitive, a green-sensitive and/or a red-sensitive silver-halide emulsion layer and, if desired, a protective layer, with a layer comprising a UV absorber being arranged above the uppermost silver-halide emulsion layer, wherein the UV absorber is a red-shifted trisaryl-1,3,5-triazine compound.

Preference is additionally given to photographic materials which have a layer comprising a compound of the formula (I)–(III) above the uppermost silver-halide emulsion layer and/or between the green- and red-sensitive silver-halide emulsion layers.

Furthermore, it may be advantageous for all or some of the said layers which can comprise a UV absorber to have a UV absorber mixture and/or a further UV absorber which is dispersible in aqueous gelatin, but a compound of the formula (I)–(III) must be present at least in one layer.

The novel material preferably has gelatin interlayers between the silver-halide emulsion layers.

Preference is given to photographic materials in which the silver halide in the blue-sensitive, green-sensitive and/or red-sensitive layer is silver chloride bromide comprising at least 90 mol % of silver chloride.

The compounds of the formula (I)–(III), which are used in accordance with the invention, can be incorporated, alone or together with the color coupler and, if used, further additives, into the color photographic materials by dissolving the compounds beforehand in high-boiling organic solvents. It is preferred to use solvents which boil at higher than 160° C. Typical examples of such solvents are the esters of phthalic acid, phosphoric acid, citric acid, benzoic acid or of fatty acids, or alkylamides and phenols.

Preferred color couplers for use in the compositions of the invention, examples of such compounds, further additives such as color cast inhibitors, DIR couplers and further light stabilizers, such as UV absorbers, phenols, phosphorus (III) compounds, organometallic complexes, hydroquinones and hydroquinone ethers, and more precise details on the structure of various photographic materials, can be found, for example, in the publications EP-A-0531258 and EP-A-0520938 and in the literature cited therein.

Film

The invention also relates to a process for the stabilization of polyolefin or polyolefin copolymer films for agricultural applications, especially greenhouse applications, this polyolefin or polyolefin copolymer film having improved light stability and pesticide resistance, comprising incorporation of the triazines of the present invention combined with a sterically hindered amine and a metal oxide or hydroxide selected from oxides of zinc, aluminum, calcium and magnesium, and hydroxides of zinc, aluminum and calcium, into the polyolefin or polyolefin copolymer.

Another subject of the invention is a greenhouse, characterized in that it is covered by a polyolefin or polyolefin copolymer film having improved light stability and pesticide resistance and stabilized with the triazines of the present invention combined with a sterically hindered amine and a metal oxide or hydroxide selected from oxides of zinc, aluminum, calcium and magnesium, and hydroxides of zinc, aluminum and calcium, and a process for stabilizing a polyolefin or polyolefin copolymer greenhouse film against detrimental effects of pesticides and light, oxygen and/or heat, which process comprises incorporation of the triazines of the present invention with a sterically hindered amine and a metal oxide or hydroxide selected from oxides of zinc, aluminum, calcium and magnesium, and hydroxides of zinc, aluminum and calcium, into said greenhouse film.

Further subjects of the invention are the use of a polyolefin copolymer film stabilized with the triazines of the present invention combined with a sterically hindered amine and a metal oxide or hydroxide selected from oxides of zinc, aluminum, calcium and magnesium, and hydroxides of zinc, aluminum and calcium for agricultural applications involving pesticides, especially greenhouse applications, and the use of the triazines of the present invention with a sterically hindered amine in combination with a metal oxide or hydroxide selected from oxides of zinc, aluminum, calcium and magnesium, and hydroxides of zinc, aluminum, calcium and magnesium and hydroxides of zinc, aluminum and calcium for the stabilization of polyolefin or polyolefin copolymer films in contact with pesticides against photodegradation and damage by pesticides.

To form a film, forcing a quantity of the said melted composition through a film die, such as a flat film die or a circular blown film die, and forming a film therefrom. In the case where the composition is used to form a film therefrom, it is contemplated that the films may be unoriented, or may be subjected to a conventional operation to impart a degree of orientation on the film. Such a film may be oriented in one direction, such as in the machine direction, such as in the "machine direction" and/or the "transverse direction", or may be oriented in both directions, or "biaxially" oriented.

The present invention is also suitable for sheet applications.

The red-shifted trisaryl-1,3,5-triazine compounds of the formula (I)–(III) are suitable for the photochemical stabilization of undyed, dyed or printed fiber materials comprising for example, silk, leather, wool, polyamide or polyurethanes and especially cellulose-containing fiber materials of all kinds. Examples of such fiber materials are the natural cellulose fibers, such as cotton, linen, jute and hemp and also viscose staple fiber and regenerated cellulose. Preferred textile fiber materials are those of cotton. The triazine and pyrimidine compounds of the present invention are also suitable for the photochemical stabilization of hydroxyl-containing fibers in blend fabrics, for example blends of cotton with polyester fibers or polyamide fibers. A further preferred area of application relates to the blocking or reduction of the UV radiation which passes through the above-mentioned textile materials (UV cutting) and the heightened sun protection which textile materials finished with a novel compound offer to the human skin.

To this end, one or a number of different compounds of the formula (I)–(III) are applied to the textile fiber material by one of the customary dyeing methods, advantageously in a quantity of 0.01 to 5% by weight, preferably 0.1 to 3% by weight and, in particular, from 0.25 to 2% by weight, based on the weight of the fiber material.

The red-shifted trisaryl-1,3,5-triazine compounds can be applied to the fiber material in various ways and fixed on the fiber, especially in the form of aqueous dispersions or printing pastes.

The textile fiber materials finished with the novel compounds of the formula (I)–(III) possess improved protection against photochemical breakdowm of the fiber and yellowing phenomena and, in the case of dyed fibre material, are of enhanced (hot) light fastness. Particular emphasis should be drawn to the greatly improved photoprotective effect of the treated textile fiber material and, in particular, the good protective effect with respect to short-wave UV-B rays. This is manifested by the fact that the textile fiber material finished with an red-shifted trisaryl-1,3,5-triazine compound has, relative to untreated fabric, a greatly increased sun protection factor (SPF).

The sun protection factor is defined as the quotient of the dose of UV radiation which damages protected skin to that which damages unprotected skin. Accordingly, a sun protection factor is also a measure of the extent to which untreated fiber materials and fiber materials treated with a novel compound of the formulas (I)–(III) are permeable to UV radiation. The determination of the sun protection factor of textile fiber materials is explained, for example, in WO94/04515 or in J. Soc. Cosmet. Chem. 40 127–133 (1989) and can be carried out analogously thereto.

Yet another use of the UV absorbers according to the invention is in the stabilization of intra-ocular and contact lenses.

The inventive UV absorbers are suitable as photoprotective agents in cosmetic preparations. The invention additionally relates, therefore, to a cosmetic preparation comprising at least one red-shifted trisaryl-1,3,5-triazine compound and cosmetically acceptable carriers or auxiliaries.

The novel cosmetic composition contains from 0.1 to 15% by weight, preferably from 0.5 to 10% by weight, based on the overall weight of the composition, of a red-shifted trisaryl-1,3,5-triazine UV absorber and a cosmetically acceptable auxiliary.

The cosmetic composition can be prepared by physically mixing the novel UV absorber with the auxiliary by means of customary methods, for example by simply stirring together the two materials.

The cosmetic preparation according to the invention can be formulated as a water-in-oil or oil-in-water emulsion, as an oil-in-oil alcohol lotion, as a vesicular dispersion of an ionic or nonionic amphiphilic lipid, as a gel, solid stick or as an aerosol formulation.

As a water-in-oil or oil-in-water emulsion, the cosmetically acceptable auxiliary preferably contains from 5 to 50% of an oily phase, from 5 to 20% of an emulsifier and from 30 to 90% water. The oil phase can comprise any oil which is suitable for cosmetic formulations, e.g., one or more hydrocarbon oils, a wax, a natural oil, a silicone oil, a fatty acid ester or a fatty alcohol. Preferred mono- or polyols are ethanol, isopropanol, propylene glycol, hexylene glycol, glycerol and sorbitol.

For these cosmetic formulations, it is possible to use any conventionally employed emulsifier, e.g., one or more ethoxylated esters of naturally occurring derivatives, i.e., polyethoxylated esters of hydrogenated castor oil; or a silicone oil emulsifier such as silicone polyol; an unmodified or ethoxylated fatty acid soap; an ethoxylated fatty alcohol; an unmodified or ethoxylated sorbitan ester; an ethoxylated fatty acid; or an ethoxylated glyceride.

The cosmetic formulation can also comprise further components, for example emollients, emulsion stabilizers, skin moisteners, tanning accelerators, thickeners such as xanthan, moisture retention agents such as glycerol, preservatives, or fragrances and colorants.

The novel cosmetic formulations are notable for good protection of human skin against the damaging effect of sunlight while at the same time providing for reliable tanning of the skin.

The invention will now be illustrated by the following examples. The examples are not intended to be limiting of the scope of the present invention. In conjunction with the general and detailed descriptions above, the examples provide further understanding of the present invention.

EXAMPLES

Example 1

Reaction of a 2,4-Dihydroxy Triazine with Diallylamine and Excess Aqueous Formaldehyde

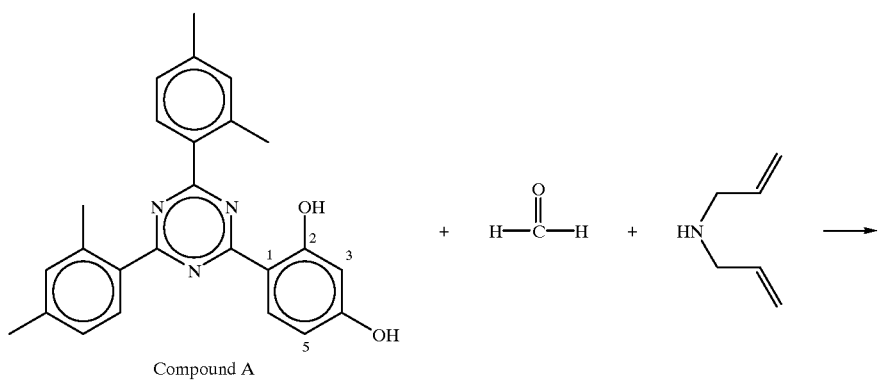
Compound A
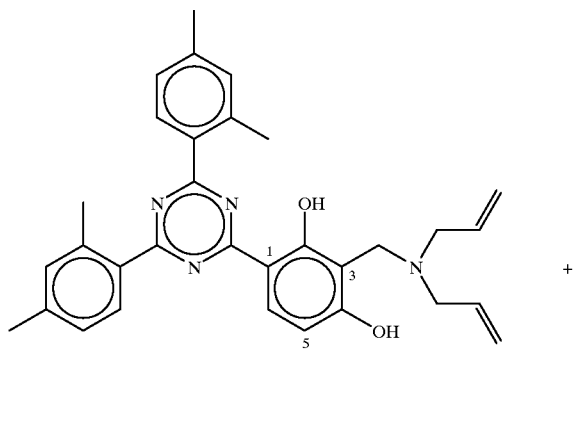
Compound B
(major)
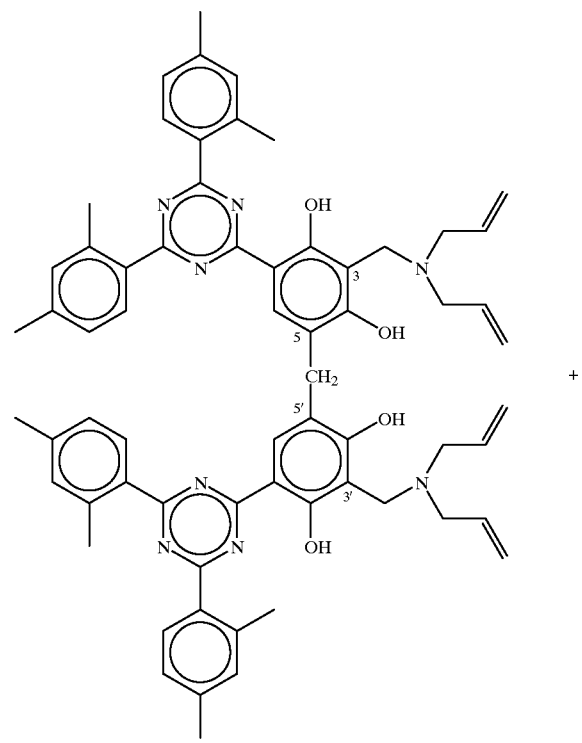
Compound C
(minor)

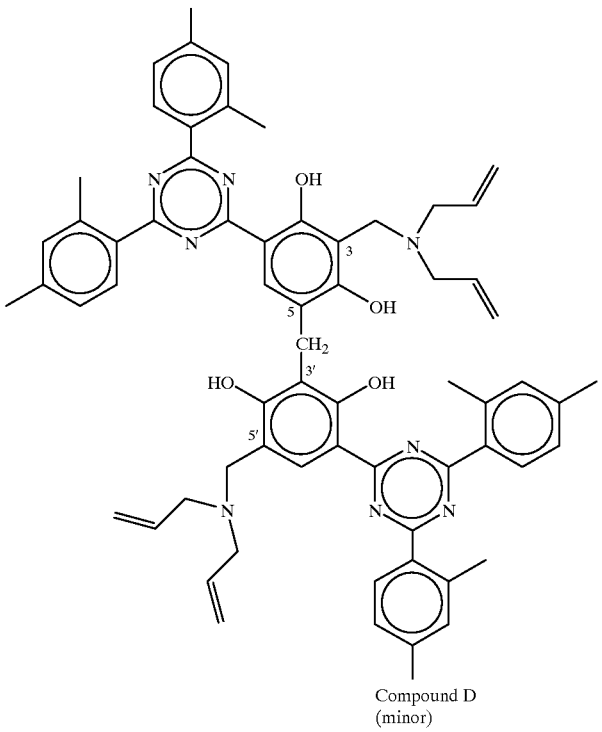

Compound D
(minor)

To a 2-neck flask equipped with a reflux condenser, an argon inlet, a magnetic stirring bar and a glass stopper was introduced 3.97 g of Compound A, 20 mL toluene, 1.3 mL diallylamine and 2.4 mL of 36% aqueous formaldehyde solution. The reaction mixture was allowed to react at reflux temperature for 2 days. The heating was discontinued and the mixture concentrated under reduced pressure. The crude product was purified by column chromatography (silica gel) to give 2.2 g of Compound B as the major product. The structure of Compound B was confirmed by NMR and mass spectra. The minor products were identified to be Compound C and Compound D, dimeric compounds, based on the NMR and mass spectra.

Comparative Example 1

Reaction of a 2-Hydroxy-4-alkoxyphenyl-containing Triazine with Diallylamine and Excess Aqueous Formaldehyde

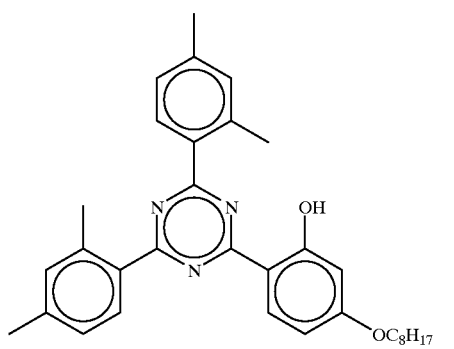

+

-continued

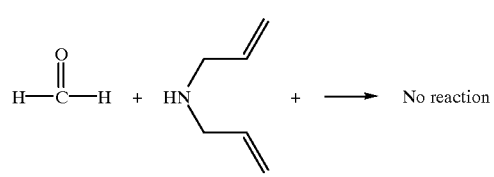

To a 2-neck flask equipped with a reflux condenser, an argon inlet, a magnetic stirring bar and a glass stopper was introduced 5.09 g of the 2-hydroxy-4-octyloxyphenyl-containing triazine as depicted above, UV-1164, 20 mL toluene, 1.3 mL diallylamine and 2.4 mL of 36% aqueous formaldehyde solution. The reaction mixture was allowed to react at reflux temperature for 2 days. The heating was discontinued and the reaction mixture analyzed by TLC (thin layer chromatography) which showed only unreacted 2-hydroxy-4-octyloxyphenyl-containing triazine and no new product spots, indicating that almost no reaction took place.

This example demonstrates that, for the reactions of the present invention, 2-hydroxy-4-alkoxyphenyl-containing triazines are not a suitable reactant. Thus, it is important to have 2,4-dihydroxyphenyl-substituted triazines as a reactant.

Example 2

Reaction of a 2,4-Dihydroxy Triazine with Excess Diallylamine and Excess Aqueous Formaldehyde

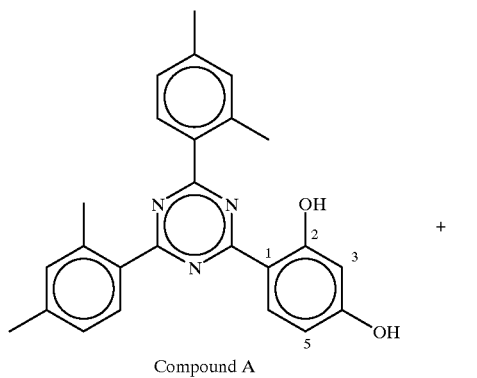

Example 3
Reaction of a 2,4-Dihydroxy Triazine with Excess Diallylamine and Excess Aqueous Formaldehyde

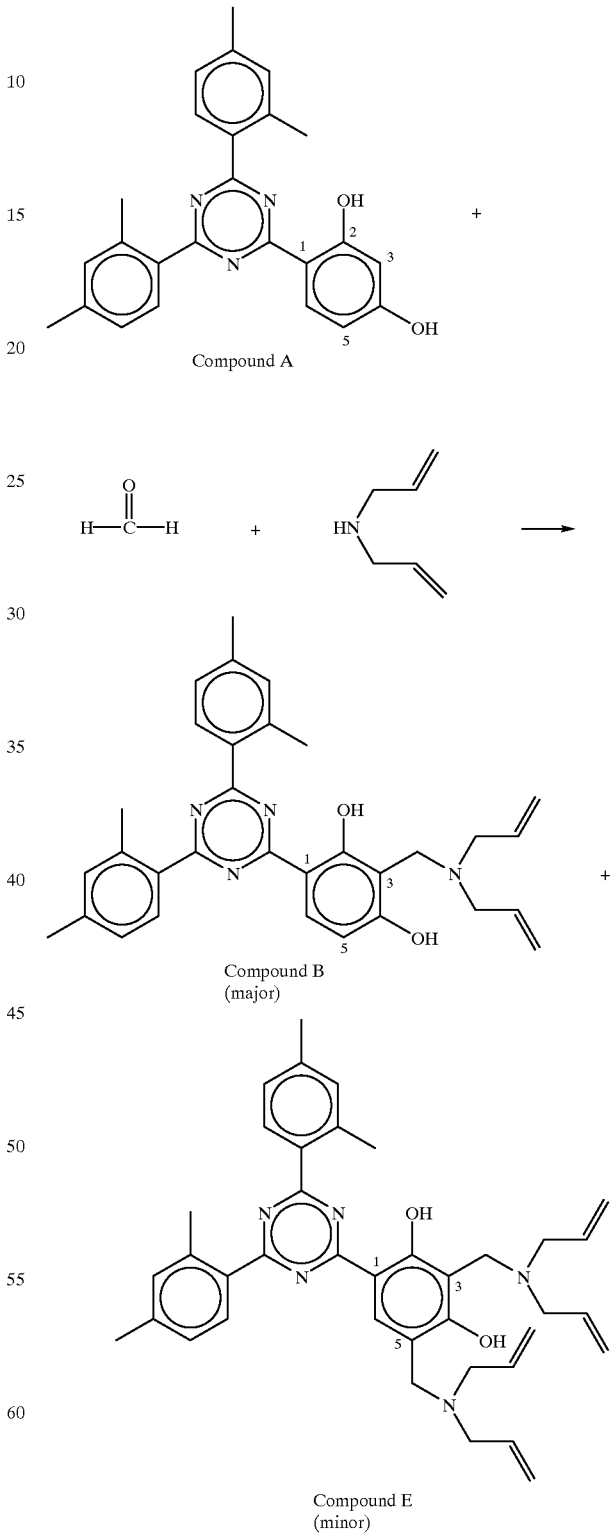

To a magnetically stirred mixture of 7.94 g of Compound A, 12.3 mL of diallylamine and 200 mL of toluene was added 10 mL of 36% aqueous formaldehyde solution. The reaction mixture was heated to reflux for 2 hrs. A TLC analysis at this stage showed the absence of Compound A and formation of only one product, which was identical to the Compound B made in Example 1.

The reaction of Example 2 was continued by heating for an additional hour. TLC analysis then showed formation of a small amount of a second product which moved faster than the starting acid on a TLC plate. Compound B was still present as the major product. The mixture was allowed to cool to room temperature. It was then concentrated under reduced pressure, and the residue was purified by column chromatography (silica gel) to give 8.1 g of a major product which was identical with the Compound B made in Example 1 as determined by NMR and TLC. The minor product (0.6 g) was also isolated and characterized as Compound E on the basis of NMR and mass spectra.

Example 4

Reaction of Compound B with 1-Iodooctane: Derivatization of the 4-Hydroxyl Group

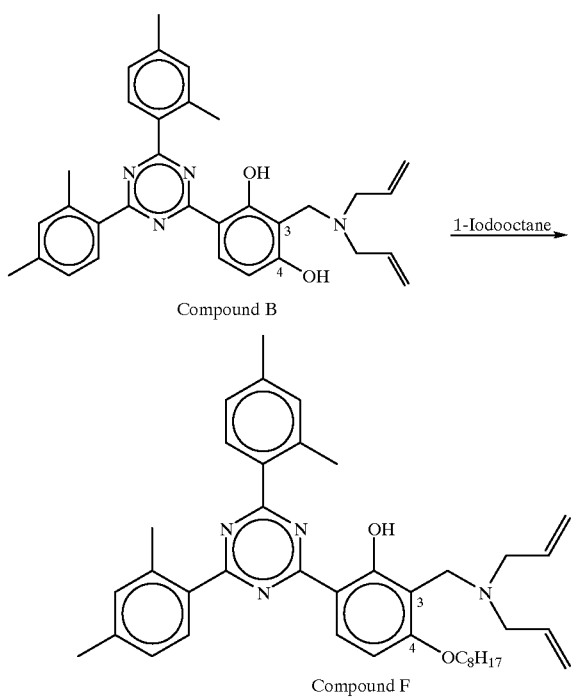

A mixture of 2.45 g of Compound B, 0.9 mL of 1-iodooctane, 2.77 g of anhydrous potassium carbonate in 20 mL of acetone was heated to reflux for 8 hours. At this time TLC showed the absence of Compound B and formation of a slower moving product. The mixture was cooled to room temperature, diluted with methylene chloride, and filtered through Celite. The filtrate was concentrated under reduced pressure to dryness to give 3.0 g of a crude product which was identified as Compound F on the basis of NMR and mass spectra.

Example 5

Effect of Red-Shifted Triazines on Cure of Coatings

The presently claimed red-shifted trisaryl-1,3,5-triazine compounds of the formula (I), (II) or (III) were tested for their effect upon curing of a coating as follows. Compound B or UV-1164 (a non-red-shifted triazine UV absorber used as a control), each present at 2% based on total resin solids, or SANDUVOR® 3055 (S-3055), a HALS-type stabilizer present at 1.6% based on total resin solids, were predissolved in mixed xylenes before addition to the clear coat formulation. Cold roll steel panels measuring 4"×12" and precoated with an electro-coat primer ED5050A and a white polyester acrylic melamine base-coat #542AB839, obtained from ACT Laboratories, Inc. (Hillsdale, Mich.), were coated with the clear coat formulation of Table 1 including the appropriate UV absorber and/or HALS. The draw-down technique, using WC-52 WIRE CATORS® (Leneta Co., Ho-Ho-Kus, N.J.) was used to apply the clear coat to the pre-coated panels. The clear coats were allowed to flash for 10 min at ambient temperature and cured for 30 min at 250° F. (120° C.). Methyl ethyl ketone (hereafter "MEK") rubs were measured to assess cure; results from multiple determinations are reported for one sample. Knoop hardness values were also measured; results from multiple determinations are reported for one sample. The results are given in Table 2.

TABLE 1

Thermoset Acrylic Melamine Clear Coat Formulation

| Component | Amount |
| --- | --- |
| JONCRYL ® 500 Acrylic Resin (80% Solids) | 81.25 parts |
| CYMEL ® 303 | 35 parts |
| CYCAT ® 4040 | 1 parts |
| n-Butanol | 20 parts |
| Xylenes | 16 parts |
| Compound B or UV-1164 | 2 parts (when present) |
| S-3055 | 1.6 parts (when present) |

TABLE 2

Effect of Compound B on Curing of Acrylic Melamine Coating

| Stabilizer | MEK Rubs | Knoop Hardness |
| --- | --- | --- |
| None | >200 | 7.4 |
|  |  | 7.5 |
| UV-1164 | >200 | 7.5 |
|  |  | 6.8 |
| Compound B | >200 | 6.5 |
|  |  | 6.5 |
| S-3055 | 1, <50 | Off-scale, Tacky |

As can be seen from Table 2, Compound B has no detrimental effect on cure since the coating comprising Compound B is able to withstand over 200 MEK rubs. In contrast, S-3055, which was added in an equimolar amount (equivalent aliphatic nitrogen content), completely inhibits the coating's cure. Compound B has a slight effect on Knoop Hardness of the coating, with a 9% lower value than UV-1164 (average for two panels of each formulation). In contrast, the panels containing S-3055 were undesirably tacky, therefore, Knoop Hardness could not be measured on them.

Example 6

Formation of Clear Coatings

A red-shifted triazine UV absorber of the present invention (2% based on the total resin solids) and/or SANDU- VOR® 3055 (1% based on total resin solids) were predissolved in the solvent mixture (5–10% solids) and added to the clear acrylic urethane formulation given in Table 3. Components I and II were mixed just before use. Cold roll steel panels measuring 4"×12" and precoated with an electro-coat primer ED5050A and a white polyester acrylic melamine base-coat #542AB839, obtained from ACT Laboratories, Inc. (Hillsdale, Mich.), were coated with the clear coating formulations of Table 3. The draw-down technique, using WC-60 WIRE CATORS® (Leneta Co., Ho-Ho-Kus, N.J.) was used to apply the clear coating to the pre-coated panels. The clear coatings were allowed to flash for 10 min at ambient temperature and cured for 30 min at 135° C.

TABLE 3

Acrylic Urethane Clear Coat Formulation

| Raw Material | Supplier | Amount |
|---|---|---|
| Component 1 Composition: | | |
| Acrylic Resin: JONCRYL® CDX-588 (70% Solids) | S. C. Johnson & Son, Inc., Racine, WI | 100 parts |
| Catalyst Solution | | 5 parts |
| Solvent Mixture | | 45 parts |
| Triazine UV Absorber | | 2 parts[a] |
| SANDUVOR S-3055 (HALS type stabilizer) | Clariant Corp., Charlotte, NC | 1 part[b] |
| Component II Composition: | | |
| Isocyanate: DESMODUR® N-3390 (90% Solids) | Miles Inc., Pittsburgh, PA | 33 parts |
| Solvent Mixture | | 17 parts |
| Catalyst Solution Composition: | | |
| (2% Solids in Catalyst Solution) | | |
| Dibutyltin Dilaurate: T-12 | Air Products, Allentown, PA | 1 part |
| Acetic Acid | | 4 parts |
| Propylene Glycol Methyl Ether Acetate (PM Acetate) | | 45 parts |
| Solvent Mixture: | | |
| Xylenes | | 1 part |
| PM Acetate | | 1 part |
| Methyl Amyl Ketone (MAK) | | 1 part |

[a]When present, amount for 2% based on total resin solids.
[b]When present, amount for 1% based on total resin solids.

Example 7

QUV Weathering Testing of Clear Coatings

Accelerated weathering was carried out on the clear coating formulations described in Example 6 using a QUV device equipped with UVB-313 fluorescent bulbs. Specular properties (gloss and distinctness of image, hereafter "DOI") and yellowing (hereafter "delta b") were measured as a function of weathering time. The effect of new stabilizer compound B alone, and in combination with S-3055, on yellowing under QUV exposure is given in Table 4. The effects of new stabilizer Compound B on gloss retention and DOI retention under QUV exposure are given in Tables 5 and 6.

TABLE 4

QUV Weathering (UVB-313 Bulbs) of an Acrylic Urethane Clear Coat Stabilized with Compound B: Effect on Yellowing (delta b)

| Stabilizer | Hours QUV Exposure | | | | | |
|---|---|---|---|---|---|---|
| | 544 | 1047 | 1984 | 2989 | 3967 | 5216 |
| None | 5.93 | 8.81 | 11.01 | a | — | — |
| 2% Compound B | 4.68 | 5.36 | 6.38 | 7.03 | 7.00 | 6.88 |
| 2% Compound B + 1% S-3055 | 2.39 | 3.15 | 3.88 | 4.36 | 4.33 | 4.29 | a) Severe chalking and gloss loss; Coating failed.

TABLE 5

QUV Weathering (UVB-313 Bulbs) of an Acrylic Urethane Clear Coat Stabilized with Compound B: Effect on Percent Gloss Retention

| Stabilizer | Hours QUV Exposure | | | | |
|---|---|---|---|---|---|
| | 1984 | 2486 | 2989 | 3467 | 3967 |
| None | 98.4 | 29.1 | 1.4[a] | — | — |
| 2% Compound B | 99.2 | 97.3 | 89.5 | 57.8 | 41.2 |
| 2% Compound B + 1% S-3055 | 100.4 | 98.2 | 95.2 | 97.4 | 93.6 |

[a]Severe chalking and gloss loss; Coating failed.

TABLE 6

QUV Weathering (UVB-313 Bulbs) of an Acrylic Urethane Clear Coat Stabilized with Compound B: Effect on Percent DOI Retention

| Stabilizer | Hours QUV Exposure | | | | |
|---|---|---|---|---|---|
| | 1984 | 2486 | 2989 | 3467 | 3967 |
| None | 101.4 | 13.1 | 0.0[a] | — | — |
| 2% Compound B | 102.8 | 103.3 | 99.3 | 60.9 | 55.3 |
| 2% Compound B + 1% S-3055 | 100.4 | 100.6 | 100.6 | 100.1 | 99.2 |

[a]Severe chalking and gloss loss; Coating failed.

As indicated in Table 4, the yellowing of the stabilized compositions was less than the unstabilized control. Furthermore, within experimental error, the yellowness of the stabilized compositions remained constant after 3000 hr.

As shown in Tables 5 and 6, the stabilized compositions show improved gloss retention compared to the control, and the addition of a HALS (S-3055) further enhances gloss and DOI retention.

Example 8

Xenon Arc Weathering Testing of Clear Coatings

Accelerated weathering was carried out on the clear coat compositions of Example 6 with an Atlas Ci65 WeatherOmeter equipped with xenon arc lamps and following the SAE J1960 automotive exterior test protocol. Specular properties (gloss and distinctness of image, or DOI) and yellowing (delta b) were measured as a function of weathering time. The effect of new stabilizer Compound B alone, and in combination with S-3055, on yellowing under QUV exposure is given in Table 7. The effects of new stabilizer Compound B on gloss retention and DOI retention under Xenon arc exposure are given in Tables 8 and 9.

TABLE 7

Xenon Arc Weathering (SAE J1960 Automotive Exterior) of a Polyurethane Acrylic Urethane Coating Stabilized with Compound B: Effect on Yellowing (delta b)

| Stabilizer | Hours Xenon Arc Exposure | | | | | | | |
|---|---|---|---|---|---|---|---|---|
| | 2988 | 3998 | 5000 | 5526 | 6997 | 7497 | 7998 | 9000 |
| None | 1.60 | 1.98 | 1.97 | 2.34 | 2.90 | 4.13 | 6.50[a] | — |
| 2% Compound B | 1.73 | 1.81 | 1.59 | 1.67 | 1.49 | 1.86 | 1.61 | 1.55 |
| 2% Compound B + 1% S-3055 | 0.90 | 0.76 | 0.10 | 0.17 | −0.20 | 0.47 | −0.05 | 0.27 |

[a]Severe chalking and gloss loss; Coating failed.

TABLE 8

Xenon Arc Weathering (SAE J1960 Automotive Exterior) of a Polyurethane Acrylic Urethane Coating Stabilized with Compound B: Effect on Percent Gloss Retention

| Stabilizer | Hours Xenon Arc Exposure | | | | | | | |
|---|---|---|---|---|---|---|---|---|
| | 2988 | 3998 | 5000 | 5526 | 6997 | 7497 | 7998 | 9000 |
| None | 96.7 | 79.9 | 63.1 | 50.6 | 34.7 | 21.4 | 13.5[a] | — |
| 2% Compound B | 95.5 | 102.8 | 81.1 | 78.8 | 73.8 | 67.9 | 59.3 | 47.9 |
| 2% Compound B + 1% S-3055 | 99.1 | 98.1 | 93.4 | 94.4 | 101.1 | 96.7 | 91.7 | 90.2 |

[a]Severe chalking and gloss loss; Coating failed.

TABLE 9

Xenon Weathering (SAE J1960 Automotive Exterior) of a Polyurethane Acrylic Coating Stabilized with Compound B: Effect on Percent DOI Retention

| Stabilizer | Hours Xenon Arc Exposure | | | | | | | |
|---|---|---|---|---|---|---|---|---|
| | 2988 | 3998 | 5000 | 5526 | 6997 | 7497 | 7998 | 9000 |
| None | 94.2 | 74.8 | 69.8 | 62.8 | 33.4 | 21.5 | 17.2[a] | — |
| 2% Compound B | 101.2 | 102.8 | 96.4 | 94.2 | 85.7 | 84.8 | 77.0 | 64.0 |
| 2% Compound B + 1% S-3055 | 102.4 | 98.1 | 102.8 | 103.7 | 102.3 | 102.8 | 103.2 | 98.9 |

[a]Severe chalking and gloss loss; Coating failed.

As shown by Table 7, while the unstabilized control yellowed up to the point of coating failure, the yellowness of the composition containing Compound B was relatively constant. The composition containing HALS S-3055 in addition to Compound B showed negligible yellowing.

As indicated in Tables 8 and 9, gloss and DOI loss for the composition containing compound B is much less than that for the unstabilized control coating, which fails at 8000 hr. The composition containing both Compound B and HALS shows little change in gloss and DOI throughout the duration of the test.

Although the above examples describe certain preferred embodiments of the present invention, it is apparent that modifications and variations thereof may be made by those skilled in the art without departing from the scope of this invention as defined by the appended claims.

Preferably the sterically hindered amine used with a red-shifted triazine of the present invention comprises at least one member of the group consisting of: bis(2,2,6,6-tetramethylpiperidin-4-yl)sebacate; bis(2,2,6,6-tetramethylpiperidin-4-yl)succinate; bis(1,2,2,6,6-pentamethylpiperidin-4-yl)sebacate; bis(1-octyloxy-2,2,6,6-tetramethylpiperidin-4-yl)sebacate; bis(1,2,2,6,6-pentamethylpiperidin-4-yl) n-butyl 3,5-di-tert-butyl-4-hydroxybenzylmalonate; the condensate of 1-(2-hydroxyethyl)-2,2,6,6-tetramethyl-4-hydroxypiperidine and succinic acid; the condensate of N,N'-bis(2,2,6,6-tetramethylpiperidin-4-yl)hexamethylenediamine and 4-tert-octylamino-2,6-dichloro-1,3,5-triazine; tris(2,2,6,6-tetramethylpiperidin-4-yl)nitrilotriacetate; tetrakis(2,2,6,6-tetramethylpiperidin-4-yl)-1,2,3,4-butanetetracarboxylate; 1,1'-(1,2-ethanediyl)bis(3,3,5,5-tetramethylpiperazinone); 4-benzoyl-2,2,6,6-tetramethylpiperidine; 4-stearyloxy-2,2,6,6-tetramethylpiperidine; bis(1,2,2,6,6-pentamethylpiperidyl)-2-n-butyl-2-(2-hydroxy-3,5-di-tert-butylbenzyl)malonate; 3-n-octyl-7,7,9,9-tetramethyl-1,3,8-triazaspiro[4.5]decan-2,4-dione; bis(1-octyloxy-2,2,6,6-tetramethylpiperidyl)sebacate; bis(1-octyloxy-2,2,6,6-tetramethylpiperidyl)succinate; the condensate of N,N'-bis(2,2,6,6-tetramethylpiperidin-4-yl)hexamethylenediamine and 4-morpholino-2,6-dichloro-1,3,5-triazine; the condensate of 2-chloro-4,6-bis(4-n-butylamino-2,2,6,6-tetramethylpiperidyl)-1,3,5-triazine and 1,2-bis(3-aminopropylamino)ethane; the condensate of 2-chloro-4,6-bis(4-n-butylamino-1,2,2,6,6-pentamethylpiperidyl)-1,3,5-triazine and 1,2-bis-(3- aminopropylamino)ethane; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl)pyrrolidin-2,5-dione; 3-dodecyl-1-(1-acetyl-2,2,6,6-tetramethylpiperidin-4-yl)pyrrolidin-2,5-dione; 3-dodecyl-1-(1,2,2,6,6-pentamethylpiperidin-4-yl)pyrrolidine-2,5-dione; a mixture of 4-hexadecyloxy- and 4-stearyloxy-2,2,6,6-tetramethylpiperidine; the condensate of N,N'-bis(2,2,6,6-tetramethylpiperidin-4-yl)hexamethylenediamine and 4-cyclohexylamino-2,6-dichloro-1,3,5-triazine; the condensate of 1,2-bis(3-aminopropylamino)ethane, 2,4,6-trichloro-1,3,5-triazine and 4-butylamino-2,2,6,6-tetramethylpiperidine; N-(2,2,6,6-tetramethyl piperidin-4-yl)-n-dodecylsuccinimide; N-(1,2,2,6.6-pentamethylpiperidin-4-yl)-n-dodecylsuccinimide; 2-undecyl-7,7,9,9-tetramethyl-1-oxa-3,8-diaza-4-oxospiro[4.5]decane; the reaction product of 7,7,9,9-tetramethyl-2-cycloundecyl-1-oxa-3,8-diaza-4-oxospiro[4.5]decane and epichlorohydrin; derivatives thereof, and mixtures thereof.

More preferably, sterically hindered amine used with a red-shifted triazine of the present invention comprises at least one member of the group consisting of: bis(2,2,6,6-tetramethylpiperidin-4-yl)sebacate; bis(1,2,2,6,6-pentamethylpiperidin-4-yl)sebacate; bis(1-octyloxy-2,2,6,6-tetramethylpiperidin-4-yl)sebacate; the condensate of N,N'-bis(2,2,6,6-tetramethylpiperidin-4-yl) hexamethylenediamine and 4-tert-octylamino-2,6-dichloro-1,3,5-triazine; the condensate of N,N'-bis(2,2,6,6-tetramethylpiperidin-4-yl)hexamethylenediamine and 4-morpholino-2,6-dichloro-1,3,5-triazine; 3-dodecyl-1-(2,2,6,6-tetramethylpiperidin-4-yl)pyrrolidin-2,5-dione; 3-dodecyl-1-(1-acetyl-2,2,6,6-tetramethylpiperidin-4-yl)pyrrolidin-2,5-dione; a mixture of 4-hexadecyloxy- and 4-stearyloxy-2,2,6,6-tetramethylpiperidine, and mixtures thereof.

Preferably, the benzotriazole used with a red-shifted triazine of the present invention comprises at least one member of the group consisting of: 2-(2'-hydroxy-5'-methylphenyl)-benzotriazole; 2-(3',5'-di-tert-butyl-2'-hydroxyphenyl) benzotriazole; 2-(5'-tert-butyl-2'-hydroxyphenyl) benzotriazole; 2-(2'-hydroxy-5'-(1,1,3,3-tetramethylbutyl) phenyl)benzotriazole; 2-(3',5'-di-tert-butyl-2'-hydroxyphenyl)-5-chlorobenzotriazole; 2-(3'-tert-butyl-2'-hydroxy-5'-methylphenyl)-5-chloro-benzotriazole; 2-(3'-sec-butyl-5'-tert-butyl-2'-hydroxyphenyl)-benzotriazole; 2-(2'-hydroxy-4'-octoxyphenyl)benzotriazole; 2-(3',5'-di-tert-amyl-2'-hydroxphenyl)benzotriazole; 2-(3',5'-bis(α,α-dimethylbenzyl)-2'-hydroxyphenyl)-benzotriazole; a mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'- [2-(2-ethylhexyloxy) carbonylethyl]-2'-hydroxyphenyl)benzotriazole, 2-(3'-dodecyl-2'-hydroxy-5'-methylphenyl)benzotriazole and 2-(3'-tert-butyl-2'-hydroxy-5'-(2-isooctyloxycarbonylethyl) phenylbenzotriazole; 2,2-methylenebis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl]benzotriazole with polyethylene glycol 300; [R—CH$_2$CH—COO(CH$_2$)$_3$]$_2$— where R=3'-tert-butyl-4'-hydroxy-5'-2H-benzotriazol-2-ylphenyl; and derivatives thereof.

More preferably, the benzotriazole used with a red-shifted triazine of the present invention comprises at least one member of the group consisting of: 2-(2'-hydroxy-5'-(1,1,3,3-tetramethylbutyl)phenyl)benzotriazole; 2-(3',5'-di-tert-amyl-2'-hydroxphenyl)benzotriazole; 2-(3',5'-bis(α,α-dimethylbenzyl)-2'-hydroxyphenyl)-benzotriazole; 2-(3'-tert-butyl-2'-hydroxy-5'-(2-octyloxycarbonylethyl)phenyl) benzotriazole, the transesterification product of 2-[3'-tert-butyl-5'-(2-methoxycarbonylethyl)-2'-hydroxyphenyl] benzotriazole with polyethylene glycol 300 and mixtures thereof.

What is claimed is:

1. A triazine compound of formula (I), (II) or (III), as follows:

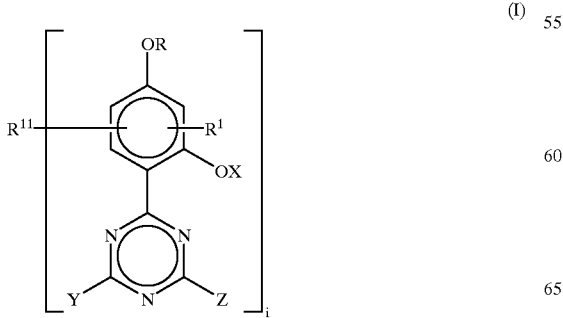

(I)

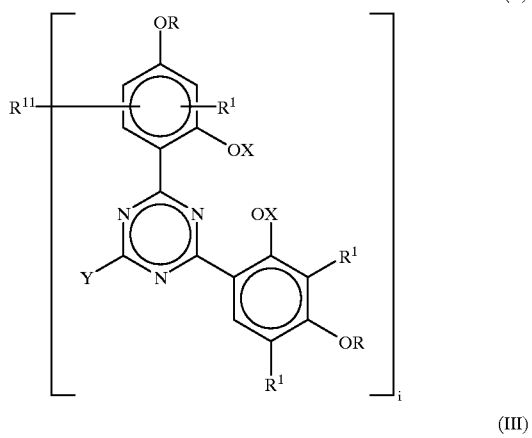

(II)

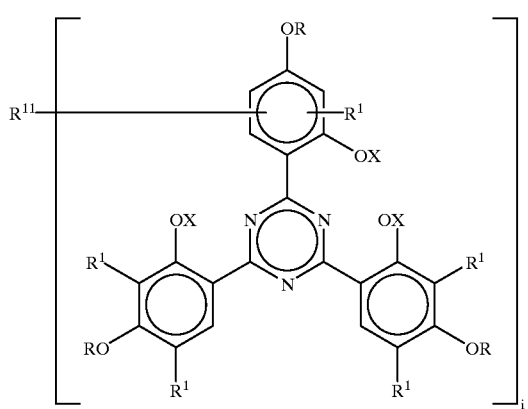

(III)

wherein i is 1 or 2;

each X is independently selected from hydrogen, C$_1$–C$_8$ alkyl, halogen-substituted C$_1$–C$_8$ alkyl, allyl, —COR$^a$, —SO$_2$R$^b$, —SiR$^c$R$^d$R$^e$, —PR$^f$R$^g$ and —POR$^f$R$^g$;

each of Y and Z is independently selected from an aryl ring of the formula (IV)

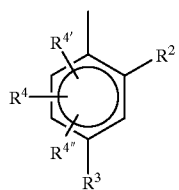

(IV)

each R is independently selected from a hydrogen, a hydrocarbyl group and a functional hydrocarbyl group;

each R$^a$ is independently selected from C$_1$–C$_8$ alkyl, halogen-substituted C$_1$–C$_8$ alkyl, C$_5$–C$_{12}$ cycloalkyl, C$_2$–C$_8$ alkenyl, —CH$_2$—CO—CH$_3$, C$_7$–C$_{12}$ aralkyl, C$_1$–C$_{12}$ alkoxy, or phenyl which is unsubstituted or substituted by C$_1$–C$_{12}$ alkyl, C$_1$–C$_4$ alkoxy, halogen and benzyl;

each $R^b$ is independently selected from $C_1$–$C_{12}$ alkyl, $C_6$–$C_{10}$ aryl and $C_7$–$C_{18}$ alkylaryl;

each $R^c$, $R^d$ and $R^e$ is independently selected from $C_1$–$C_{18}$ alkyl, cyclohexyl, phenyl and $C_1$–$C_{18}$ alkoxy;

each $R^f$ and $R^g$ is independently selected from $C_1$–$C_{12}$ alkoxy, phenoxy, $C_1$–$C_{12}$ alkyl, $C_5$–$C_{12}$ cycloalkyl, benzyl, tolyl and phenyl;

when i is 1, $R^1$ is bonded to the 3-position of the ring bearing the —OX group, $R^{11}$ is bonded to the 5-position of the ring bearing the —OX group, and $R^{11}$ is $R^1$ and, when i is 2, $R^1$ is bonded, independently, to either the 3-position or the 5-position of a first ring and a second ring bearing the —OX group and $R^{11}$ is bonded, at a first end, to the position of the first ring bearing —OX not bonded to $R^1$ and at a second end, to the position of the second ring bearing —OX not bonded to $R^1$, and $R^{11}$ is a hydrocarbylene group of 1 to 24 carbon atoms;

each $R^1$, $R^2$, $R^4$, $R^{4'}$ and $R^{4''}$ is independently selected from hydrogen, hydrocarbyl, functional hydrocarbyl, —O(hydrocarbyl), —O(functional hydrocarbyl), —SR, halogen, —SO$_2$R, —SO$_3$R, —COOR, —COR, —OCOR, —NRR and cyano; and each $R^3$ is independently selected from R, —OR, —SR, halogen, —SO$_2$R, —SO$_3$R, —COOR, —COR, —NRR and cyano; and further wherein at least one 3-position $R^1$ group is independently selected from a group of the formulae (V) and (VI)

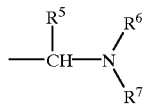

(V)

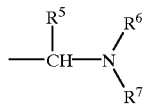

(VI)

wherein $R^5$ is independently selected from hydrogen, linear or branched hydrocarbyl group of 1 to 24 carbon atoms, phenyl, and aralkyl of 7 to 24 carbon atoms; and each $R^6$ and $R^7$ is independently selected from hydrogen, a hydrocarbyl group and a functional hydrocarbyl group.

2. The compound of claim 1 selected from the group consisting of the compounds of formula (VII), (VIII), (IX), (XA), (XB), (XC), (XIA), (XIB), (XIC), (XIIA), (XIIB) or (XIIC)

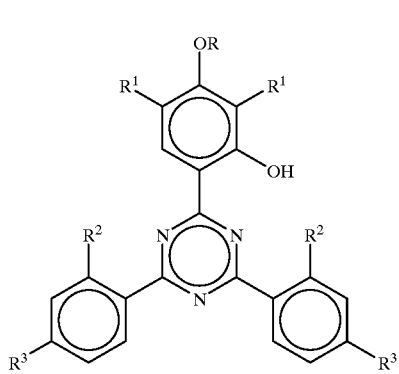

(VII)

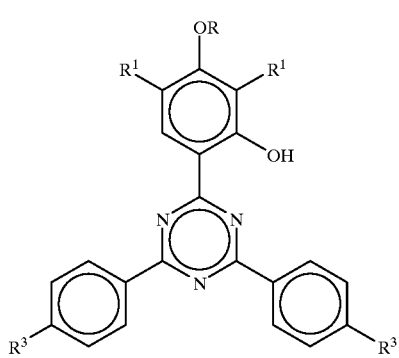

(VIII)

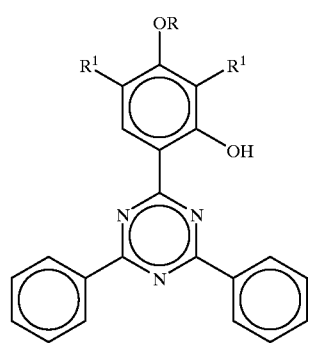

(IX)

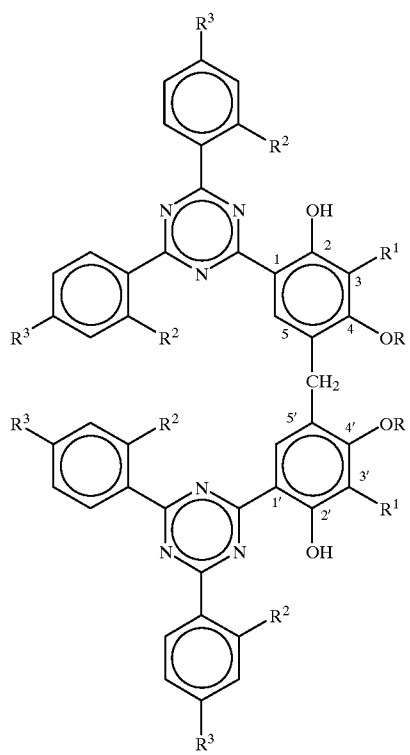
(XA)
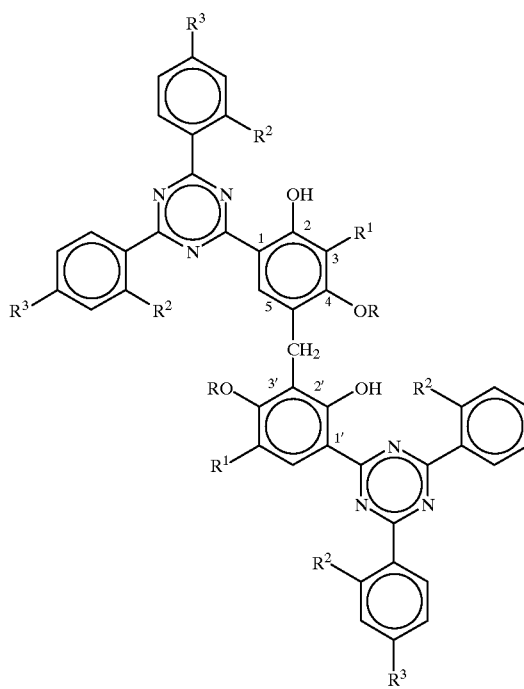
(XB)
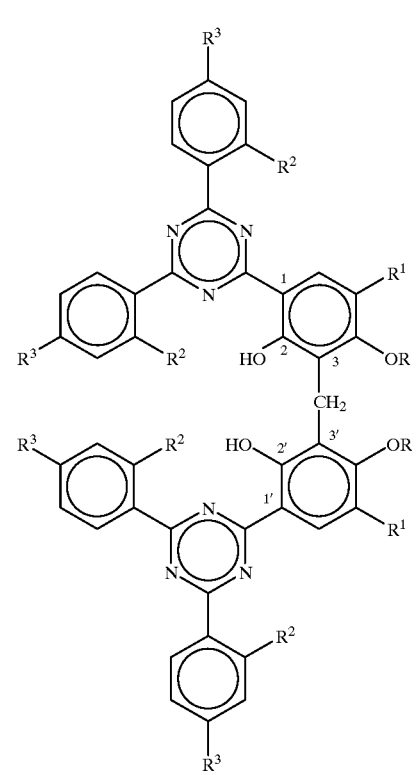
(XC)
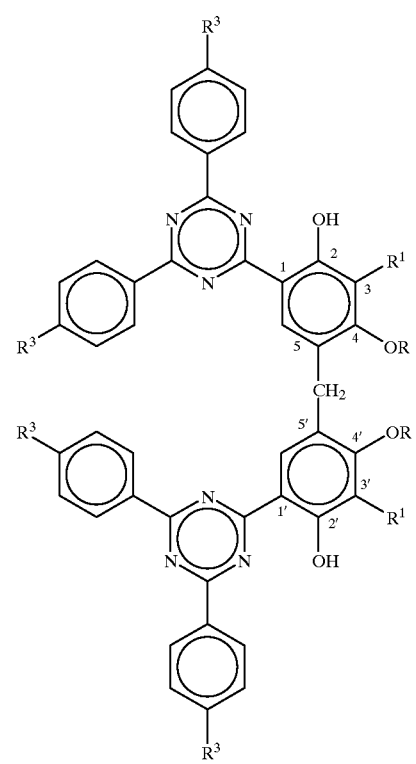
(XIA)

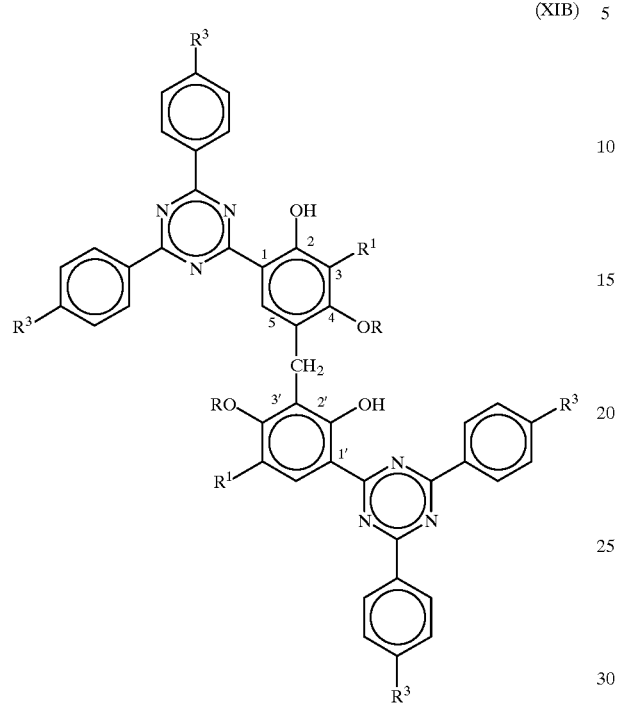
(XIB)
(XIC)
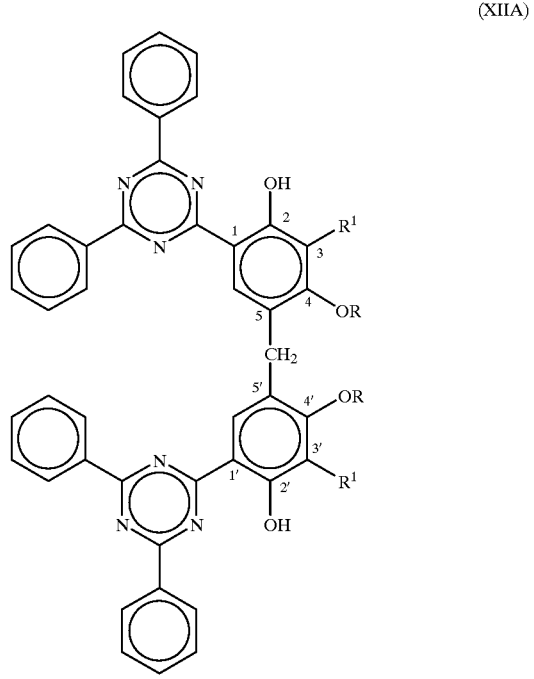
(XIIA)
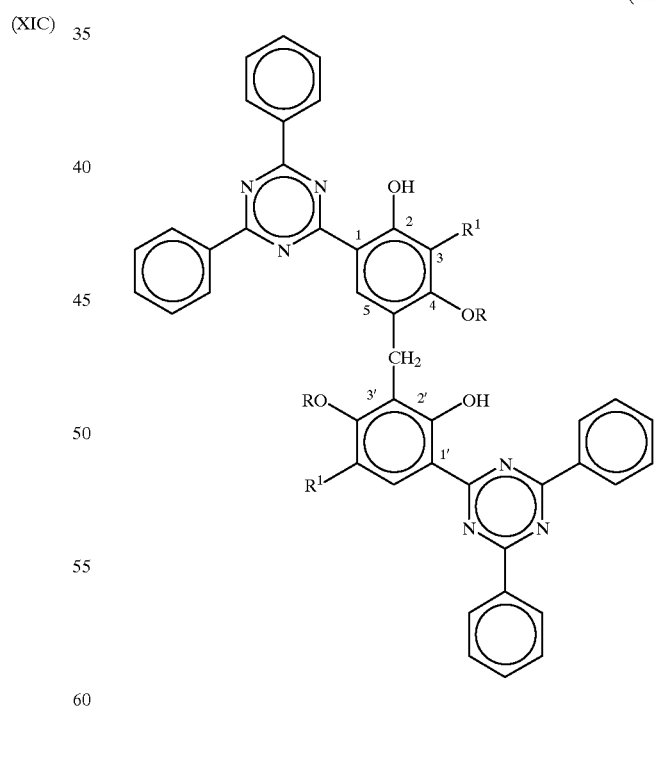
(XIIB)

-continued

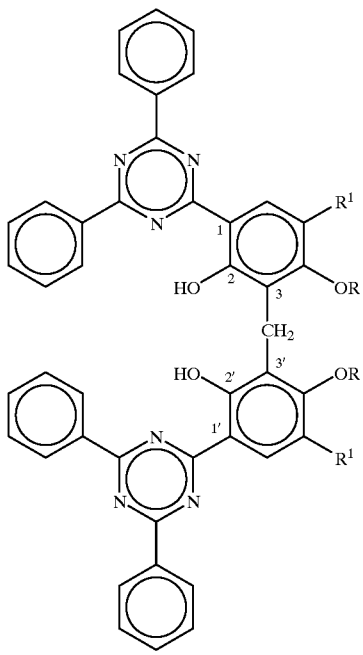
(XIIC)

wherein
each R is independently selected from a hydrogen, a hydrocarbyl group and a functional hydrocarbyl group;
each $R^1$ and $R^2$ is independently selected from hydrogen, hydrocarbyl, functional hydrocarbyl, —O(hydrocarbyl), —O(functional hydrocarbyl), —SR, halogen, —$SO_2R$, —$SO_3R$, —COOR, —COR, —OCOR, —NRR and cyano; and
each $R^3$ is independently selected from R, —OR, —SR, halogen, —$SO_2R$, —$SO_3R$, —COOR, —COR, —NRR and cyano; and further wherein at least one 3-position $R^1$ group is independently selected from a group of the formulae (V) and (VI)

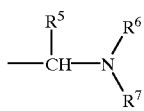
(V)

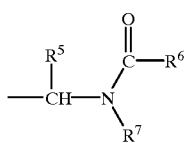
(VI)

wherein
$R^5$ is independently selected from hydrogen, linear or branched hydrocarbyl group of 1 to 24 carbon atoms, phenyl, and aralkyl of 7 to 24 carbon atoms; and
each $R^6$ and $R^7$ is independently selected from hydrogen, a hydrocarbyl group and a functional hydrocarbyl group.

3. The compound of claim 1 selected from the group consisting of the compounds of formula (XIII), (XIV) or (XV)

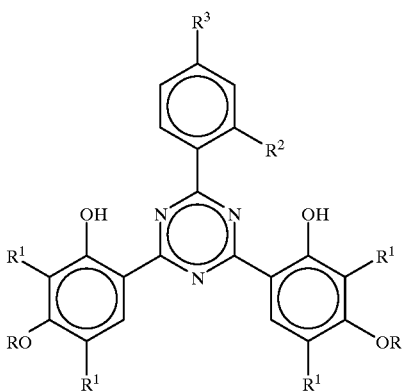
(XIII)

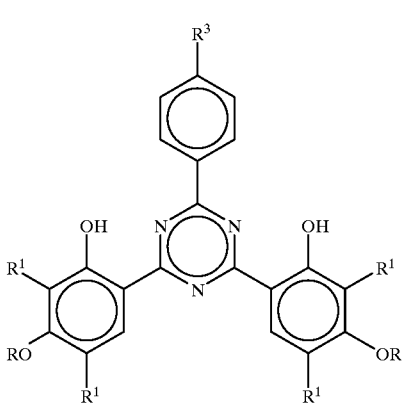
(XIV)

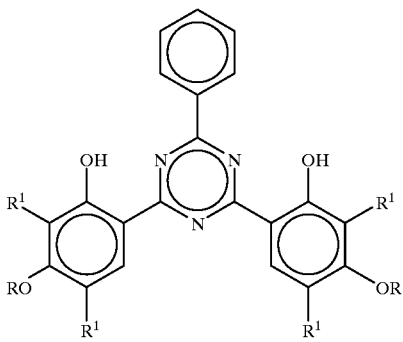
(XV)

wherein each R is independently selected from a hydrogen, a hydrocarbyl group and a functional hydrocarbyl group;

each $R^1$ and $R^2$ is independently selected from hydrogen, hydrocarbyl, functional hydrocarbyl, —O(hydrocarbyl), —O(functional hydrocarbyl), —SR, halogen, —$SO_2R$, —$SO_3R$, —COOR, —COR, —OCOR, —NRR and cyano; and each $R^3$ is independently selected from R, —OR, —SR, halogen, —$SO_2R$, —$SO_3R$, —COOR, —COR, —NRR and cyano; and further wherein at least one 3-position $R^1$ group is independently selected from a group of the formulae (V) and (VI)

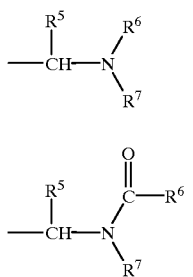

wherein
R⁵ is independently selected from hydrogen, linear or branched hydrocarbyl group of 1 to 24 carbon atoms, phenyl, and aralkyl of 7 to 24 carbon atoms; and
each R⁶ and R⁷ is independently selected from hydrogen, a hydrocarbyl group and a functional hydrocarbyl group.

4. The compound of claim 1 of the following formula

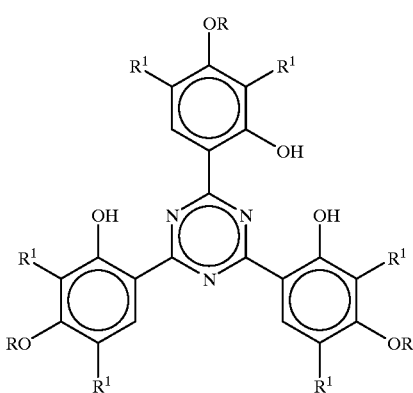

wherein
each R is independently selected from a hydrogen, a hydrocarbyl group and a functional hydrocarbyl group;
each R¹ is independently selected from hydrogen, hydrocarbyl, functional hydrocarbyl, —O(hydrocarbyl), —O(functional hydrocarbyl), —SR, halogen, —SO₂R, —SO₃R, —COOR, —COR, —OCOR, —NRR and cyano; and further wherein at least one 3-position R¹ group is independently selected from a group of the formulae (V) and (VI)

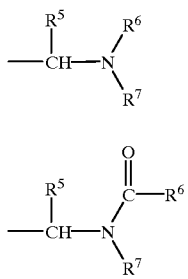

wherein
R⁵ is independently selected from hydrogen, linear or branched hydrocarbyl group of 1 to 24 carbon atoms, phenyl, and aralkyl of 7 to 24 carbon atoms; and each R⁶ and R⁷ is independently selected from hydrogen, a hydrocarbyl group and a functional hydrocarbyl group.

5. The compound of claims 2, 3 or 4, wherein each R² is independently selected from hydrogen, an alkyl of 1 to 8 carbon atoms, an alkyloxy of 1 to 8 carbon atoms optionally containing an oxygen atom in the chain, a hydroxyalkyl of 1 to 8 carbon atoms group optionally containing an oxygen atom in the chain, a hydroxyalkyloxy of 1 to 8 carbon atoms group optionally containing an oxygen atom in the chain and an acyloxy of 2 to 12 carbon atoms; each R³ is independently selected from hydrogen, an alkyl of 1 to 24 carbon atoms optionally containing an oxygen atom in the chain, a hydroxyalkyl of 1 to 24 carbon atoms group optionally containing an oxygen atom in the chain and —OR; each R⁵ is independently selected from hydrogen and linear or branched alkyl groups of 1 to 24 carbon atoms; and each of R⁶ and R⁷ is independently selected from hydrogen, an alkyl group of 1 to 24 carbon atoms which may optionally contain carbonyl and/or one or more oxygen atoms in the chain, and an aralkyl group of 7 to 24 carbon atoms, and at least one of which is substituted by a hydroxyl, —CR⁹=CHR¹⁰ or —CO—CR⁹=CHR¹⁰, wherein R⁹ is independently selected from hydrogen and an alkyl of 1 to 4 carbon atoms and R¹⁰ is independently selected from hydrogen, a hydrocarbyl group of 1 to 8 carbon atoms, and phenyl.

6. The compound of claims 1, 2, 3 or 4, wherein the group of formula (V) contains at least one of the following structures

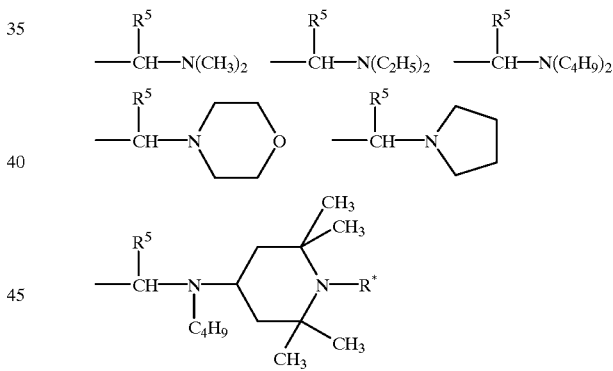

wherein R* is H, CH₃,

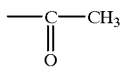

or

—OC₈H₁₇

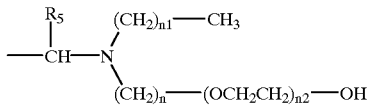

-continued

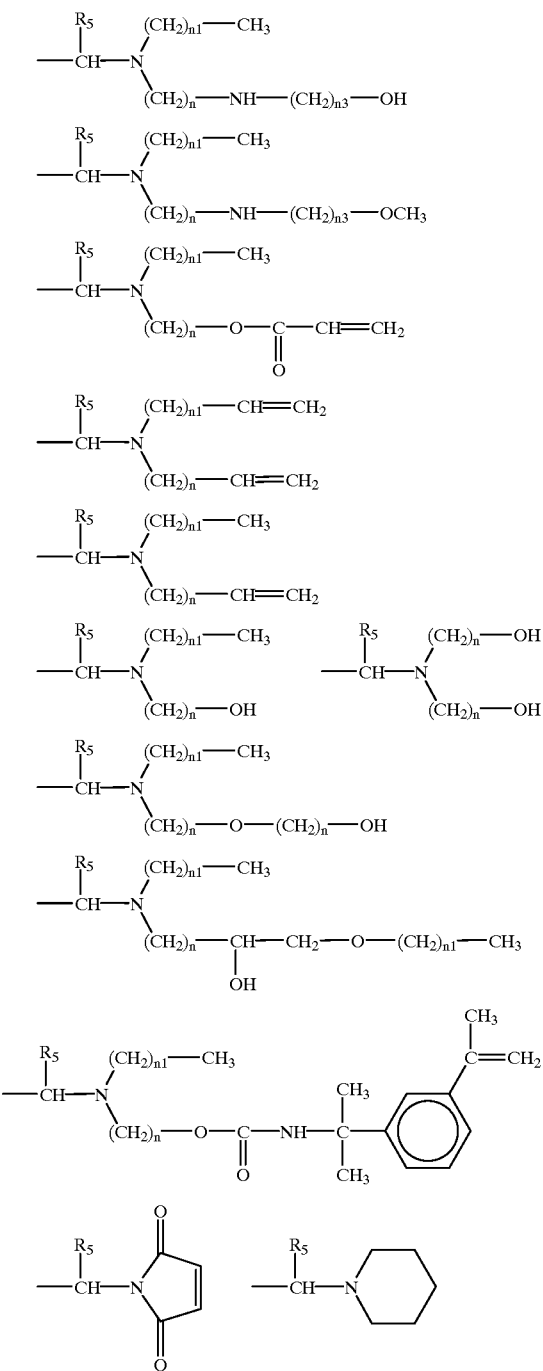

wherein n is 1–24, n1 is 0–23, n2 is 1–50 and n3 is 1–24;

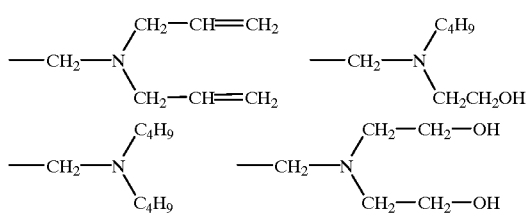

-continued

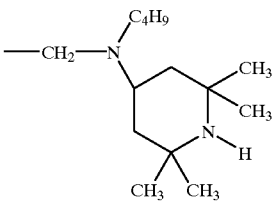

7. The compound of claims 1, 2, 3 or 4, wherein the group of formula (VI) contains at least one of the following structures

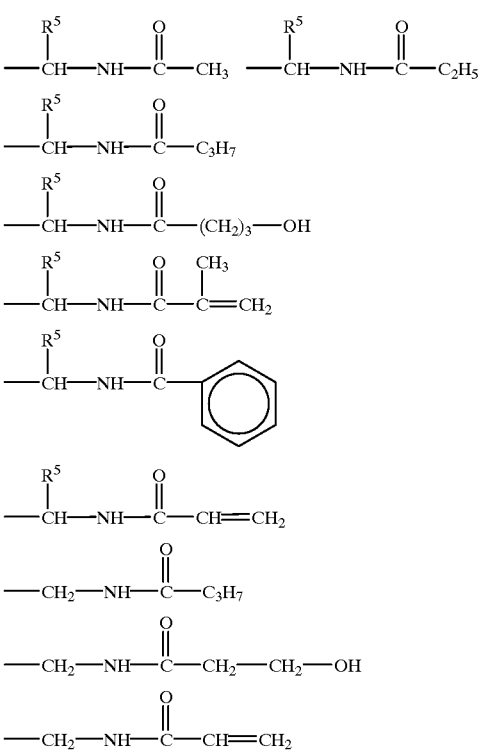

8. The compound of claim 2 of formula (VII) wherein the 5-position $R^1$ group is hydrogen; each $R^2$ group is independently selected from hydrogen, an alkoxy of 1 to 4 carbon atoms and an alkyl of 1 to 4 carbon atoms; each $R^3$ group is independently selected from hydrogen, an alkyl of 1 to 4 carbon atoms, and —OR; each R group is independently selected from hydrogen, an alkyl of 1 to 24 carbon atoms optionally containing an oxygen atom in the chain, and a hydroxyalkyl of 1 to 24 carbon atoms group optionally containing an oxygen atom in the chain; and the 3-position $R^1$ group is a group of formula (V) where $R^5$ is selected from hydrogen and an alkyl of 1 to 24 carbon atoms and $R^6$ and $R^7$ are allyl.

9. The compound of claim 2 of formula (VII) wherein R is hydrogen; the 5-position $R^1$ group is hydrogen; each $R^2$ group and each $R^3$ group is methyl; and the 3-position $R^1$ group is a group of formula (V) where $R^5$ is hydrogen and $R^6$ and $R^7$ are allyl.

10. The compound of claim 2 of formula (VII) wherein the 5-position $R^1$ group is hydrogen; each $R^2$ group is independently selected from hydrogen, an alkoxy of 1 to 4 carbon atoms and an alkyl of 1 to 4 carbon atoms; each $R^3$ group is independently selected from hydrogen, an alkyl of 1 to 4 carbon atoms, and —OR; each R group is independently selected from hydrogen, an alkyl of 1 to 24 carbon atoms optionally containing an oxygen atom in the chain, and a hydroxyalkyl of 1 to 24 carbon atoms group optionally containing an oxygen atom in the chain; and the 3-position $R^1$ group is a group of formula (V) where $R^5$ is selected from hydrogen and an alkyl of 1 to 24 carbon atoms and $R^6$ and $R^7$ are allyl.

11. The compound of claim 2 of formula (VII) wherein the 5-position $R^1$ group is hydrogen; each $R^2$ group and each $R^3$ group is methyl; R is octyl; and the 3-position $R^1$ group is a group of formula (V) where $R^5$ is hydrogen and $R^6$ and $R^7$ are allyl.

12. The compound of claim 2 of formula (VII) wherein each $R^2$ group is independently selected from hydrogen, an alkoxy of 1 to 4 carbon atoms and an alkyl of 1 to 4 carbon atoms; each $R^3$ group is independently selected from hydrogen, an alkyl of 1 to 4 carbon atoms, and —OR; each R group is independently selected from hydrogen, an alkyl of 1 to 24 carbon atoms optionally containing an oxygen atom in the chain, and a hydroxyalkyl of 1 to 24 carbon atoms group optionally containing an oxygen atom in the chain; and the 3-position and 5-position $R^1$ groups are a group of formula (V) where $R^5$ is selected from hydrogen and an alkyl of 1 to 24 carbon atoms and $R^6$ and $R^7$ are allyl.

13. The compound of claim 2 of formula (VII) wherein each $R^2$ group and each $R^3$ group is methyl; R is hydrogen; and the 3-position and 5-position $R^1$ groups are a group of formula (V) where $R^5$ is hydrogen and $R^6$ and $R^7$ are allyl.

14. The compound of claim 2 of formula (XA) wherein each $R^2$ group is independently selected from hydrogen, an alkoxy of 1 to 4 carbon atoms and an alkyl of 1 to 4 carbon atoms; each $R^3$ group is independently selected from hydrogen, an alkyl of 1 to 4 carbon atoms, and —OR; each R group is independently selected from hydrogen, an alkyl of 1 to 24 carbon atoms optionally containing an oxygen atom in the chain, and a hydroxyalkyl of 1 to 24 carbon atoms group optionally containing an oxygen atom in the chain; and the 3-position and 3'-position $R^1$ groups are a group of formula (V) where $R^5$ is selected from hydrogen and an alkyl of 1 to 24 carbon atoms and $R^6$ and $R^7$ are allyl.

15. The compound of claim 2 of formula (XA) wherein each $R^2$ group and each $R^3$ group is methyl; each R is hydrogen; and the 3-position and 3'-position $R^1$ groups are a group of formula (V) where $R^5$ is hydrogen and $R^6$ and $R^7$ are allyl.

16. The compound of claim 2 of formula (XB) wherein each $R^2$ group is independently selected from hydrogen, an alkoxy of 1 to 4 carbon atoms and an alkyl of 1 to 4 carbon atoms; each $R^3$ group is independently selected from hydrogen, an alkyl of 1 to 4 carbon atoms, and —OR; each R group is independently selected from hydrogen, an alkyl of 1 to 24 carbon atoms optionally containing an oxygen atom in the chain, and a hydroxyalkyl of 1 to 24 carbon atoms group optionally containing an oxygen atom in the chain; and the 3-position and 5'-position $R^1$ groups are a group of formula (V) where $R^5$ is selected from hydrogen and an alkyl of 1 to 24 carbon atoms and $R^6$ and $R^7$ are allyl.

17. The compound of claim 2 of formula (XB) wherein each $R^2$ group and each $R^3$ group is methyl; each R is hydrogen; and the 3-position and 5'-position $R^1$ groups are a group of formula (V) where $R^5$ is hydrogen and $R^6$ and $R^7$ are allyl.

18. A triazine compound of formula (I), (II) or (III), as follows:

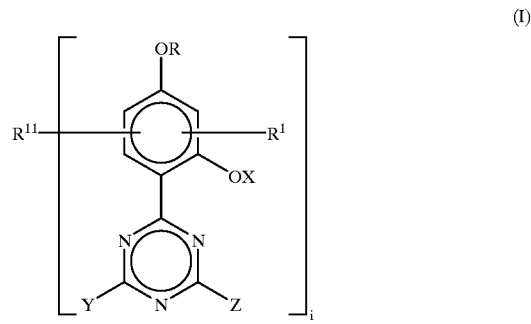

(I)

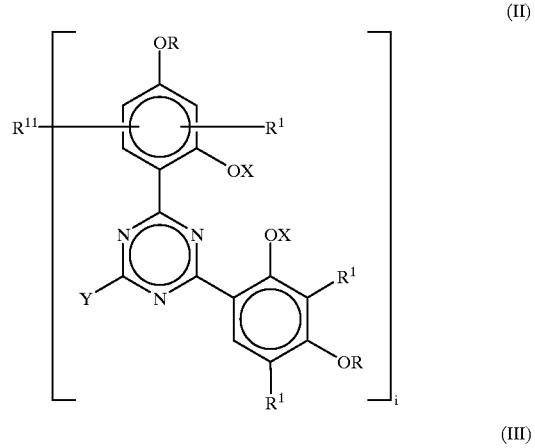

(II)

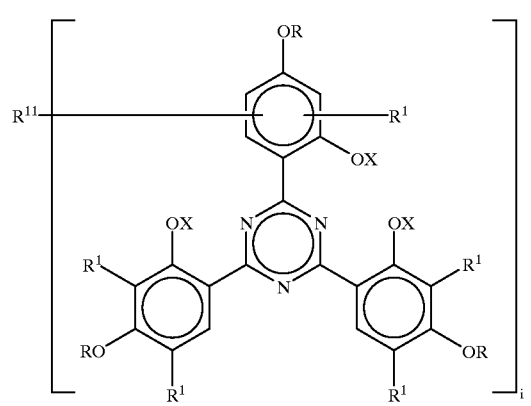

(III)

wherein i is 1 or 2;

each X is independently selected from hydrogen, $C_1$–$C_8$ alkyl, halogen-substituted $C_1$–$C_8$ alkyl, allyl, —$COR^a$, —$SO_2R^b$, —$SiR^cR^dR^e$, —$PR^fR^g$ and —$POR^fR^g$;

each of Y and Z is independently selected from an aryl ring of the formula (IV)

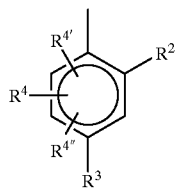
(IV)

each R is independently selected from a hydrogen, a hydrocarbyl group and a functional hydrocarbyl group;

each $R^a$ is independently selected from $C_1$–$C_8$ alkyl, halogen-substituted $C_1$–$C_8$ alkyl, $C_5$–$C_{12}$ cycloalkyl, $C_2$–$C_8$ alkenyl, —$CH_2$—CO—$CH_3$, $C_7$–$C_{12}$ aralkyl, $C_1$–$C_{12}$ alkoxy, or phenyl which is unsubstituted or substituted by $C_1$–$C_{12}$ alkyl, $C_1$–$C_4$ alkoxy, halogen and benzyl;

each $R^b$ is independently selected from $C_1$–$C_{12}$ alkyl, $C_6$–$C_{10}$ aryl and $C_7$–$C_{18}$ alkylaryl;

each $R^c$, $R^d$ and $R^e$ is independently selected from $C_1$–$C_{18}$ alkyl, cyclohexyl, phenyl and $C_1$–$C_{18}$ alkoxy;

each $R^f$ and $R^g$ is independently selected from $C_1$–$C_{12}$ alkoxy, phenoxy, $C_1$–$C_{12}$ alkyl, $C_5$–$C_{12}$ cycloalkyl, benzyl, tolyl and phenyl;

when i is 1, $R^1$ is bonded to the 3-position of the ring bearing the —OX group, $R^{11}$ is bonded to the 5-position of the ring bearing the —OX group, and $R^{11}$ is $R^1$ and, when i is 2, $R^1$ is bonded, independently, to either the 3-position or the 5-position of a first ring and a second ring bearing the —OX group and $R^{11}$ is bonded, at a first end, to the position of the first ring bearing —OX not bonded to $R^1$ and at a second end, to the position of the second ring bearing —OX not bonded to $R^1$, and $R^{11}$ is a hydrocarbylene group of 1 to 24 carbon atoms;

each $R^1$, $R^2$, $R^4$, $R^{4'}$ and $R^{4"}$ is independently selected from hydrogen, hydrocarbyl, functional hydrocarbyl, —O(hydrocarbyl), —O(functional hydrocarbyl), —SR, halogen, —$SO_2R$, —$SO_3R$, —COOR, —COR, —OCOR, —NRR and cyano; and each $R^3$ is independently selected from R, —OR, —SR, halogen, —SO2R, —$SO_3R$, —COOR, —COR, —NRR and cyano; and further wherein at least one 3-position or 5-position $R^1$ group is independently selected from a group of the formula (VI)

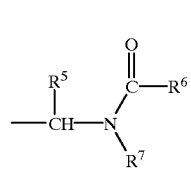
(VI)

wherein $R^5$ is independently selected from hydrogen, linear or branched hydrocarbyl group of 1 to 24 carbon atoms, phenyl, and aralkyl of 7 to 24 carbon atoms; and each $R^6$ and $R^7$ is independently selected from hydrogen, a hydrocarbyl group and a functional hydrocarbyl group.

* * * * *